US010849867B2

(12) United States Patent
Glick et al.

(10) Patent No.: US 10,849,867 B2
(45) Date of Patent: *Dec. 1, 2020

(54) METHODS AND COMPOSITIONS FOR TREATING CONDITIONS ASSOCIATED WITH AN ABNORMAL INFLAMMATORY RESPONSE

(71) Applicant: First Wave Bio, Inc., Ann Arbor, MI (US)

(72) Inventors: Gary D. Glick, Ann Arbor, MI (US); Luigi Franchi, Ann Arbor, MI (US)

(73) Assignee: First Wave Bio, Inc., Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/871,717

(22) Filed: May 11, 2020

(65) Prior Publication Data

US 2020/0268694 A1 Aug. 27, 2020

Related U.S. Application Data

(63) Continuation of application No. 16/173,667, filed on Oct. 29, 2018, which is a continuation of application
(Continued)

(51) Int. Cl.
*A61K 31/167* (2006.01)
*A61K 9/00* (2006.01)
(Continued)

(52) U.S. Cl.
CPC .......... *A61K 31/167* (2013.01); *A61K 9/0031* (2013.01); *A61K 9/10* (2013.01);
(Continued)

(58) Field of Classification Search
CPC .................................................. A61K 31/167
See application file for complete search history.

(56) References Cited

U.S. PATENT DOCUMENTS

| | | | |
|---|---|---|---|
| 3,079,297 | A | 2/1963 | Schraufstatter et al. |
| 4,496,086 | A | 1/1985 | Duchadeau |
| (Continued) | | | |

FOREIGN PATENT DOCUMENTS

| | | |
|---|---|---|
| CN | 101601670 | 12/2009 |
| CN | 102861014 | 1/2013 |
| (Continued) | | |

OTHER PUBLICATIONS

Kahler et al., "Treatment and side effect management of CTLA-4 antibody therapy in metastatic melanoma," JDDG, 2011, 9:277-285.
(Continued)

*Primary Examiner* — Benjamin J Packard
(74) *Attorney, Agent, or Firm* — Fish & Richardson P.C.

(57) ABSTRACT

This disclosure features chemical entities (e.g., a compound exhibiting activity as a mitochondrial uncoupling agent or a pharmaceutically acceptable salt and/or hydrate and/or cocrystal thereof; e.g., a compound, such as niclosamide or a pharmaceutically acceptable salt and/or hydrate and/or cocrystal thereof; e.g., a compound, such as a niclosamide analog, or a pharmaceutically acceptable salt and/or hydrate and/or cocrystal thereof) that are useful, e.g., for treating one or more symptoms of a pathology characterized by an abnormal inflammatory response (e.g., inflammatory bowel diseases) in a subject (e.g., a human). This disclosure also features compositions as well as other methods of using and making the same.

28 Claims, 7 Drawing Sheets

Effect of Niclosamide on Lamina Propria T Cells Isolated from Inflamed Colon Tissue (biopsy from Crohn's patients)

Apoptosis of T cells (CD45+CD3+) was detected 7ADD uptake and Annexin V staining

Related U.S. Application Data

No. 15/255,102, filed on Sep. 1, 2016, now Pat. No. 10,292,951.

(60) Provisional application No. 62/241,508, filed on Oct. 14, 2015, provisional application No. 62/213,016, filed on Sep. 1, 2015.

(51) Int. Cl.
| | |
|---|---|
| *A61K 45/06* | (2006.01) |
| *A61K 9/10* | (2006.01) |
| *A61K 9/16* | (2006.01) |
| *A61K 47/32* | (2006.01) |
| *A61K 47/38* | (2006.01) |

(52) U.S. Cl.
CPC ............ *A61K 45/06* (2013.01); *A61K 9/1635* (2013.01); *A61K 47/32* (2013.01); *A61K 47/38* (2013.01)

(56) References Cited

U.S. PATENT DOCUMENTS

| | | |
|---|---|---|
| 5,280,784 A | 1/1994 | Kohler |
| 5,309,900 A | 5/1994 | Knoch et al. |
| 5,312,046 A | 5/1994 | Knoch et al. |
| 5,458,136 A | 10/1995 | Jaser et al. |
| 5,461,695 A | 10/1995 | Knoch |
| 5,549,102 A | 8/1996 | Lintl et al. |
| 5,663,155 A | 9/1997 | McCaffrey |
| 5,740,966 A | 4/1998 | Blaha-Schnabel |
| 5,905,090 A | 5/1999 | Bertolini |
| 5,914,132 A | 6/1999 | Kelm et al. |
| 5,957,389 A | 9/1999 | Wunderlich et al. |
| 6,000,394 A | 12/1999 | Blaha-Schnabel et al. |
| 6,085,741 A | 7/2000 | Becker |
| 6,176,237 B1 | 1/2001 | Wunderlich et al. |
| 6,224,910 B1 | 5/2001 | Ullah et al. |
| 6,228,396 B1 | 5/2001 | Watts |
| 6,513,519 B2 | 2/2003 | Gallern |
| 6,513,727 B1 | 2/2003 | Jaser et al. |
| 6,862,890 B2 | 3/2005 | Williams, III et al. |
| 7,132,546 B2 | 11/2006 | Kato et al. |
| 7,544,712 B1 | 6/2009 | Hsu et al. |
| 7,635,722 B1 | 12/2009 | Bachynsky et al. |
| 7,691,578 B2 | 4/2010 | Spiegelman |
| 7,927,613 B2 | 4/2011 | Almarsson et al. |
| 7,989,498 B2 | 8/2011 | Saunders |
| 8,097,759 B2 | 1/2012 | Muto et al. |
| 8,148,328 B2 | 4/2012 | Fogelman |
| 8,262,657 B2 | 9/2012 | Muto et al. |
| 8,968,786 B2 | 3/2015 | Johnston et al. |
| 9,023,368 B2 | 5/2015 | Basit et al. |
| 9,044,391 B2 | 6/2015 | Willaims et al. |
| 9,061,027 B2 | 6/2015 | Hitt et al. |
| 9,175,906 B2 | 11/2015 | Scherzer et al. |
| 9,192,583 B2 | 11/2015 | Shah et al. |
| 9,237,760 B2 | 1/2016 | Ravishankar et al. |
| 9,308,213 B2 | 4/2016 | Bannister et al. |
| 9,546,211 B2 | 1/2017 | Singh |
| 9,566,399 B1 | 2/2017 | Bono et al. |
| 9,598,422 B2 | 3/2017 | Beck et al. |
| 9,622,974 B2 | 4/2017 | Johnston et al. |
| 9,669,036 B2 | 6/2017 | Roizman et al. |
| 9,724,344 B2 | 8/2017 | Hitt et al. |
| 10,092,512 B2 | 10/2018 | Johnston et al. |
| 10,189,797 B2 | 1/2019 | Chen et al. |
| 10,231,955 B2 | 3/2019 | Williams, III et al. |
| 10,285,945 B2 | 5/2019 | Johnston et al. |
| 10,434,062 B2 | 10/2019 | Johnston et al. |
| 10,463,680 B2 | 11/2019 | Sommer et al. |
| 10,562,864 B2 | 2/2020 | Chen et al. |
| 10,588,864 B2 | 3/2020 | Linanli |
| 2004/0022861 A1 | 2/2004 | Williams, III et al. |
| 2004/0091523 A1 | 5/2004 | Weibel |
| 2005/0123571 A1 | 6/2005 | Rossini et al. |
| 2009/0062396 A1 | 3/2009 | Olesen et al. |
| 2009/0163408 A1 | 6/2009 | Fogelman et al. |
| 2009/0208582 A1 | 8/2009 | Johnston et al. |
| 2012/0035106 A1 | 2/2012 | Betancourt et al. |
| 2013/0078226 A1 | 3/2013 | Nakauchi et al. |
| 2013/0231312 A1 | 9/2013 | Jin |
| 2013/0243886 A1 | 9/2013 | Hu et al. |
| 2014/0256661 A1 | 9/2014 | Armstrong |
| 2015/0056160 A1 | 2/2015 | Bachynsky et al. |
| 2015/0133405 A1 | 5/2015 | Pelletier et al. |
| 2016/0074328 A1 | 3/2016 | Scherzer et al. |
| 2016/0243117 A1 | 8/2016 | Menon et al. |
| 2017/0165238 A1 | 6/2017 | Williams, III et al. |
| 2018/0015153 A1 | 1/2018 | Tang et al. |
| 2018/0147161 A1 | 5/2018 | Williams, III et al. |
| 2018/0243333 A1 | 8/2018 | Brown et al. |
| 2019/0060289 A1 | 2/2019 | Deretic et al. |
| 2019/0160028 A1 | 5/2019 | Li et al. |
| 2019/0269661 A1 | 9/2019 | Williams, III et al. |
| 2019/0343783 A1 | 11/2019 | Yook et al. |
| 2019/0274958 A1 | 12/2019 | Johnston et al. |
| 2020/0022931 A1 | 1/2020 | Deshpande et al. |
| 2020/0046659 A1 | 2/2020 | Melnyk et al. |
| 2020/0069572 A1 | 3/2020 | Johnston et al. |

FOREIGN PATENT DOCUMENTS

| | | |
|---|---|---|
| CN | 105063018 A | 11/2015 |
| EP | 0938338 B1 | 9/2009 |
| EP | 3168211 | 5/2017 |
| WO | WO 1991/13281 | 9/1991 |
| WO | WO 2002/060411 | 8/2002 |
| WO | WO 2004/006906 | 1/2004 |
| WO | WO 2004/064808 | 8/2004 |
| WO | WO 2006/026502 | 3/2006 |
| WO | WO 2006/120178 | 11/2006 |
| WO | WO 2008/127746 | 10/2008 |
| WO | WO 2009/002874 | 12/2008 |
| WO | WO 2009/103035 | 8/2009 |
| WO | WO 2010/048114 | 4/2010 |
| WO | WO 2011/035321 | 3/2011 |
| WO | WO 2012/068274 | 5/2012 |
| WO | WO 2012/143377 | 10/2012 |
| WO | WO 2012/154944 | 11/2012 |
| WO | WO 2014/108571 | 7/2014 |
| WO | WO 2014/185973 | 11/2014 |
| WO | WO 2005/017755 | 2/2015 |
| WO | WO 2014/023329 | 2/2015 |
| WO | WO 2015/017755 | 5/2015 |
| WO | WO 2015/106150 | 7/2015 |
| WO | WO 2016/178704 | 11/2016 |
| WO | WO2016/193136 | 12/2016 |
| WO | WO 2017/223491 | 12/2017 |
| WO | WO 2018/017426 | 1/2018 |
| WO | WO 2018/136559 | 7/2018 |
| WO | WO 2018/141063 | 8/2018 |
| WO | WO 2018/173069 | 9/2018 |
| WO | WO 2018/191776 | 10/2018 |
| WO | WO 2018/205016 | 11/2018 |
| WO | WO 2018/213834 | 11/2018 |
| WO | WO 2018/128515 | 12/2018 |
| WO | WO 2019/051437 | 3/2019 |
| WO | WO 2019/051440 | 3/2019 |
| WO | WO 2019/126283 | 6/2019 |
| WO | WO 2019/147626 | 8/2019 |
| WO | WO 2019/217164 | 11/2019 |

OTHER PUBLICATIONS

Nytimes.com [online], "South Korea's Daewoong Pharmaceutical Says Anti-Parasitic Drug Effective Against Coronavirus in Animal Tests," Jun. 2020, [retrieved on Jun. 10, 2020] retrieved from: URL <https://www.nytimes.com/reuters/2020/06/09/world/asia/09reuters-health-coronavirus-pharmaceuticals.html>, 2 pages.

Thejakartapost.com [online] "Daewoong Pharmaceutical says anti-parasitic drug effective against coronavirus in animal tests," Jun.

(56) References Cited

OTHER PUBLICATIONS

2020, [retrieved on Jun. 10, 2020], retrieved from: URL<https://www.thejakartapost.com/news/2020/06/09/s-koreas-daewoong-pharmaceutical-says-anti-parasitic-drug-effective-against-coronavirus-.html, 4 pages.
Amidon et al., "Colon-Targeted Oral Drug Delivery Systems: Design Trends and Approaches," AAPS PharmSciTech, 2015, 16(4):731-741.
Anatherapeutics.com [online], "Niclosamide & COVID-19: Let's Keep This Simple," available on or before Apr. 2020, [retrieved on May 19, 2020], retrieved from: URL<https://anatherapeutics.com/home/niclosamine-and-covid19-keep-it-simple>, 4 pages.
Anatherapeutics.com [online], "Our Plan," available on or before Apr. 2020, [retrieved on May 19, 2020], retrieved from: URL<https://anatherapeutics.com/home/our-plan>, 5 pages.
Anonymous, "New Delivery Method Could Make Niclosamide an Effective Antiviral to Treat COVID-19," UTexas PressRelease, Apr. 6, 2020, [retrieved on May 19, 2020], retrieved from URL<https://news.utexas.edu/2020/04/06/new-delivery-method-could-make-niclosamide-an-effective-antiviral-to-treat-covid-19/> 6 pages.
Auriemma et al., "Prilling for the development of multi-particulate colon drug delivery systems: Pectin vs. pectin-alginate beads," Carbohydrate Polymers, 2013, 92(1):367-373.
Bewtra et al., "Update on the risk of lymphoma following immunosuppressive therapy for inflammatory bowel disease," Expert Rev Clin Immunol., 2010,6(4): 559-566.
Bouman-Boyer et al., "An International Guideline for the Preparation, Care and Use of Medicinal Products," Practical Pharmaceutics, Aug. 24, 2015, 11.9.5.2 p. 220.
Casadevall et al., "The convalescent sera option for containing COVID-19." The Journal of Clinical Investigation, 2020 130(4):1545-1548.
Cen.acs.org [online], "Can old drugs take down a new coronavirus?," Mar. 20, 2020, [retrieved on May 19, 2020], retrieved from: URL<https://cen.acs.org/sections/coronavirus/biological-chemistry/infectious-disease/coronavirus-drug-repurposing.html>, 4 pages.
Chang et al. "Potential therapeutic agents for COVID-19 based on the analysis of protease and RNA polymerase docking." Preprints 2020, 11 pages.
Chang et al., "Pharmacokinetics of Anti-SARS-CoV Agent Niclosamide and Its Analogs in Rats," Journal of Food and Drug Analysis, 2006, 14(4):329-333.
Cho et al., [kxan.com] "Can an existing drug be re-purposed to treat COVID-19 patients? UT researchers working to find out," Apr. 6, 2020, [retrieved on May 19, 2020, retrieved from URL<https://www.kxan.com/news/coronavirus/can-an-existing-drug-be-re-purposed-to-treat-covid-19-patients-ut-researchers-working-to-find-out/>.
Corman et al. "Detection of 2019 Novel Coronavirus (2019-nCoV) by Real-Time RT-PCR," Eurosurveillance, 25(3):2000045, 8 pages.
Costabile et al. "Toward Repositioning Niclosamide for Antivirulence Therapy of Pseudomonas aeruginosa Lung Infections: Development of Inhalable Formulations through Nanosuspension Technology," Mol Pharm., 2015, 12(8):2604-2617.
CureZone.org, dated Feb. 2, 2014, retrieved on May 15, 2017, retrieved from http://www.curezone.org/forums/fm.asp?i=2146880#i, 2 pages.
Defendants Answer to Complaint, Counterclaim ("The Counterclaim"), filed on Jun. 16, 2017., Case IFM Therapeutics, *First Wave Bio, Inc., Gary D. Glick, and Luigi Franchi* v. *Lycera Corporation* (17-cv-608) (D. Del.).
Dhama et al., "Coronavirus Disease 2019—COVID-19," Preprint 2020, 2020030001.
Dubald et al. "Ophthalmic Drug Delivery Systems for Antibiotherapy—A Review," Pharmaceutics., 2018; 10(1):10, 31 pages.
Filipski et al., "Intestinal targeting of drugs: rational design approaches and challenges," *Current Topics in Medicinal Chemistry*., 13(7):776-802, 2013.

Frizelle et al., "Hyponatremia and Seizures After Bowel Preparation: Report of Three Cases," Dis Colon Rectum, 2005, 48(2):393-396.
Gautret et al., "Hydroxychloroquine and azithromycin as a treatment of COVID-19: results of an openlabel non-randomized clinical trial," International Journal of Antimicrobial Agents, 2020, 24 pages.
Gautret et al., "Clinical and microbiological effect of a combination of hydroxychloroquine and azithromycin in 80 COVID-19 patients with at least a six-day follow up: A pilot observational study," Travel Medicine and Infectious Disease, 2020, 34:101663.
Gassen et al., "Analysis of SARS-CoV-2-controlled autophagy reveals spermidine, MK-2206, and niclosamide as 1 putative antiviral therapeutics," bioRxiv, 2020, 13 pages.
Grifasi et al., "Using Salt Cosrystals to Improve the Solubility of Niclosamide," Cryst. Growth Des. 2015, 15:1939-1948.
Imramovsky et al., "Crystal Structure of the 5-Chloro Salicylamides: Three Different Types of the H-bonding Influenced Linear Chain Formation in the Solid State," *Crystals*., 2012, 2:349-361.
International Search Report and Written Opinion in International Application No. PCT/US2016/050012, dated Jan. 23, 2017, 22 pages.
Ir.tffpharma.com [online], "TFF Pharmaceuticals' Inventor Dr. Robert O. Williams III Presents Session on Repurposing Niclosamide for COVID-19 Treatment at AAPS Meeting," Apr. 30, 2020 [retrieved on May 19, 2020], retrieved from URL<https://ir.tffpharma.com/news-releases/news-release-details/tff-pharmaceuticals-inventor-dr-robert-o-williams-iii-presents>, 2 pages.
Jeon et al., "Identification of antiviral drug candidates against SARS-CoV-2 from FDA-approved drugs," bioRxiv, 2020, 20 pages.
Jeon et al., "Identification of antiviral drug candidates against SARS-CoV-2 from FDA-approved drugs," bioRxiv, 2020, 21 pages.
Jin et al., "Epidemiological, clinical and virological characteristics of 74 cases of coronavirus-infected disease 2019 (COVID-19) with gastrointestinal symptoms," Gut 2020, 1-8.
Ko et al., "Arguments in favor of remdesivir for treating SARS-CoV-2 infections," Int J Antimicrob Agents, 2020,105933, 15 pages.
Koreabiomed.com [online], "Pasteur, Daewoong to co-develop COVID-19 drug from parasiticide," Apr. 14, 2020, [retrieved on May 19, 2020], retrieved from: URL<http://www.koreabiomed.com/news/articleView.html?idxno=8003>, 4 pages.
Koreabiomed.com [online], "Parasiticide showed antiviral effect as potential Covid-19 drug," Apr. 24, 2020, [retrieved on May 19, 2020], retrieved from: URL<http://www.koreabiomed.com/news/articleView.html?idxno=8078>, 7 pages.
Kratky et al., "Antiviral Activity of Substituted Salicylanilides—A Review," Mini-Review in Medicinal Chemistry, 2011, 11:956-967.
Labiris et al., "Pulmonary drug delivery. Part II: The role of inhalant delivery devices and drug formulations in therapeutic effectiveness of aerosolized medications," Br J Clin Pharmacol., 2003, 56(6): 600-612.
Lai et al., "Severe acute respiratory syndrome coronavirus 2 (SARS-CoV-2) and corona virus disease-2019 (COVID-19): the epidemic and the challenges." International journal of antimicrobial agents, 2020, 55(3):105924.
Latimes.com [online], "Drugs for heartburn, gout and depression now being tested as coronavirus treatments," May 2, 2020, [retrieved on May 19, 2020], retrived from: URL<https://www.latimes.com/science/story/2020-05-02/researchers-testing-pepcid-as-coronavirus-treatment>, 7 pages.
Lawrance et al., "A murine model of chronic inflammation-induced intestinal fibrosis down-regulated by antisense NF-kappa B," *Gastroenterology*., 125(6): 1750-1761, Dec. 2003.
Liu et al., "Research and development on therapeutic agents and vaccines for COVID-19 and related human coronavirus diseases," ACS Central Science, Mar. 9, 2020, 17 pages.
Liu et al., "Viral dynamics in mild and severe cases of COVID-19," The Lancet, 2020,1-4 pages.
Luedeker et al., "Crystal Engineering of Pharameutical Co-crystals: "NMR Crystallography" of Niclosamide Co-crystals," Cryst. Growth Des. 2016 16:3087-3100.
Medscape.com [Online], "Role of Fecal Excretion in Spread of SARS-CoV-2 'Cannot Be Ignored'," May 1, 2020, [retrieved on

(56) References Cited

OTHER PUBLICATIONS

May 19, 2020], retrieved from: URL<https://www.medscape.com/viewarticle/929731?nlid=135353_5402&src=wnl_dne_200504_mscpedit&uac=155533FK&impID=2369009&faf=1>, 9 pages.

Memorandum Opinion, *IFM Therapeutics, INC., First Wave Bio, INC., Gary D. Glick, and Luigi Franchi*, Plantiff, v., *Lycera Corporation*, Defendant, C.A. No. 17-608-LPS, Aug. 31, 2018, 25 pages.

Memorandum Order signed by the Honorable Leonard P. Stark on Jun. 12, 2017 ("The Order") Case *IFM Therapeutics, First Wave Bio, Inc., Gary D. Glick, and Luigi Franchi v. Lycem Corporation* (17-cv-608) (D. Del.).

Milojevic et al., "Amylose as a coating for drug delivery to the colon: Preparation and in vitro evaluation using 5-aminosalicylic acid pellets." Journal of controlled release, 1996, 38:75-84.

Milojevic et al., "Amylose as a coating for drug delivery to the colon: Preparation and in vitro evaluation using glucose pellets." Journal of controlled release, 1996, 38:85-94.

Mook et al., "Structure—activity studies of Wnt/β-catenin inhibition in the Niclosamide chemotype: Identification of derivatives with improved drug exposure," Bioorg. Med Chem, 2015, 23,(17): 5829-5838.

Morin et al., "Niclosamide Prevents Systemic Sclerosis in a Reactive Oxygen Species-Induced Mouse Model," J Immunol, 2016, 197:3018-3028.

Nelson et al., "Azithromycin has anti-viral properties that are critical to consider in the treatment regimen for COVID-19," MindImmune, 2017, 6 pages.

Newswire.com [online], "UNION therapeutics Launches COVID-19 Program in Collaboration With Institut Pasteur Korea," Apr. 14, 2020, [retrieved on May 19, 2020], retrieved from: URL<https://www.newswire.com/news/union-therapeutics-launches-covid-19-program-in-collaboration-with-21127619>, 7 pages.

Newton et al., "Pectin-HPMC E15LV Vs pH sensitive polymer coating films for delayed drug delivery to colon: a comparison of two dissolution models to assess colonic targeting performance in-vitro," International Journal of Applied Research in Natural Products, 2012;5(3), 16 pages.

Pan et al., "Clinical characteristics of COVID-19 patients with digestive symptoms in Hubei, China: a descriptive, cross-sectional, multicenter study," American Journal of Gastroenterol, 2020, 25 pages.

Patel et al., "Ocular drug delivery systems: an overview," World Journal of Pharmacology, Jun. 9, 2013, 2(2), 35 pages.

Postow et al., "Immune Checkpoint Blockade in Cancer Therapy," J Clin Oncol., 2015, 33(17):1974-1982.

Raoult et al., "Clinical and microbiological effect of a combination of hydroxychloroquine and azithromycin in 80 COVID-19 patients with at least a six-day follow up: an observational study," 2020, 28 pages.

Sanphui et al., "Pharmaceutical Cocrystals of Niclosamide," *Cryst. Growth Des*. Jul. 24, 2012, 12(9):4588-4599.

Scheiffele et al., "Induction of TNBS Colitis in Mice," Current Protocols in Immunology, 2001, 49(1):15.19.1-15.19.14.

Shanmugaraj et al., "Perspectives on monoclonal antibody therapy as potential therapeutic intervention for Coronavirus disease-19 (COVID-19)," Asian Pacific Journal of Allergy and Immunology, Mar. 1, 2020, 38(1):10-8, 9 pages.

Stebbing et al., "COVID-19: combining antiviral and anti-inflammatory treatments," The Lancet Infectious Diseases, Feb. 27, 2020.

Transcript of telephone conference with Honorable Leonard P. Stark, Jun. 9, 2017, ("The TRO transcript") Case *IFM Therapeutics, First Wave Bio, Inc., Gary D. Glick, and Luigi Franchi v. Lycera Corporation* (17-cv-608) (D. Del.).

TFF Pharmaceuticals, "Advanced Technology for Better Drug Delivery Options," Present at Proceeding of the May 2020 Corporate Investor Presentation, Power Point, TFF Pharmaceuticals, May 2020, Retrieved from URL<(https://ir.tffpharma.com/static-files/065981d2-3d22-4348-a4be-e3dfle4f96d6)>, 29 pages.

Uniontherapeutics.com [online], "UNION therapeutics launches COVID-19 program in collaboration with Institut Pasteur Korea," Apr. 2, 2020, [retrieved on May 19, 2020], retrieved from: URL<https://www.uniontherapeutics.com/news-events/news/union-therapeutics-launches-covid-19-program-in-collaboration-with-institut-pasteur-korea>, 5 pages.

U.S. Food and Drug Administration, "Emergency Use Authorizations," retrieved from <https://www.fda.gov/medical-devices/emergency-situations-medical-devices/emergency-use-authorizations#covid19ivd>, Retrieved on Apr. 3, 2020, 12 pages.

World Health Organization, "Protocol: Real-time RT-PCR assays for the detection of SARS-CoV-2," Institut Pasteur, Paris, retrieved from <https://www.who.int/docs/default-source/coronaviruse/real-time-rt-per-assays-for-the-detection-of-sars-cov-2-institut-pasteur-paris.pdf>, 3 pages.

Wu et al., "Inhibition of Severe Acute Respiratory Syndrome Coronavirus Replication by Niclosamide," Mini-Reviews in Medicinal Chemistry, 2011, 11:956-967.

Xu et al., "Broad Spectrum Antiviral Agent Niclosamide and Its Therapeutic Potential," ACS Infectious Diseases, Mar. 3, 2020, 25 pages.

Yang et al., "Targeting the Endocytic Pathway and Autophagy Process as a Novel Therapeutic Strategy in COVID-19," International Journal of Biological Sciences, Mar. 15, 2020, 16(10):1724-31.

U.S. Appl. No. 15/255,102 (now U.S. Pat. No. 10,292,951, filed Sep. 1, 2016.
U.S. Appl. No. 16/173,667, filed Oct. 29, 2018.
U.S. Appl. No. 16/738,618, filed Jan. 9, 2020.
U.S. Appl. No. 16/738,695, filed Jan. 9, 2020.
U.S. Appl. No. 16/805,245, filed Feb. 28, 2020.
U.S. Appl. No. 16/805,393, filed Feb. 28, 2020.
U.S. Appl. No. 15/931,320, filed May 13, 2020.
U.S. Appl. No. 16/842,695, filed Apr. 7, 2020.
U.S. Appl. No. 16/835,307, filed Mar. 31, 2020.

| Rectal Cannula | TP-1130/A |
|---|---|
| Raw Material | MP 400 – LDPE PHARMALENE MP20PH |
|  |  |
| Single flow pack | MV-0139/B |
| Raw Material | Sealable polypropylene film |

US 10,849,867 B2

METHODS AND COMPOSITIONS FOR TREATING CONDITIONS ASSOCIATED WITH AN ABNORMAL INFLAMMATORY RESPONSE

CROSS REFERENCE TO RELATED APPLICATIONS

This application is a continuation of U.S. application Ser. No. 16/173,667, filed Oct. 29, 2018, which is a continuation of U.S. application Ser. No. 15/255,102, filed Sep. 1, 2016, which claims the benefit of United States Provisional Application No. 62/213,016, filed on Sep. 1, 2015 and U.S. Provisional Application No. 62/241,508, filed on Oct. 14, 2015; each of these prior applications is incorporated herein by reference in its entirety.

TECHNICAL FIELD

This disclosure features chemical entities (e.g., a compound exhibiting activity as a mitochondrial uncoupling agent or a pharmaceutically acceptable salt, and/or hydrate, and/or cocrystal, and/or drug combination thereof; e.g., a compound, such as niclosamide or a pharmaceutically acceptable salt, and/or hydrate, and/or cocrystal, and/or drug combination thereof; e.g., a compound, such as a niclosamide analog, or a pharmaceutically acceptable salt, and/or hydrate, and/or drug combination, and/or cocrystal thereof) that are useful, e.g., for treating one or more symptoms of a pathology characterized by an abnormal inflammatory response (e.g., inflammatory bowel diseases) in a subject (e.g., a human). This disclosure also features compositions as well as other methods of using and making the same.

BACKGROUND

Ulcerative colitis (UC) and Crohn's disease (CD) are the predominant chronic, inflammatory bowel diseases (IBD) in humans. These disorders are autoimmune in nature and occur in the absence of infection. IBD effects up to 2,000,000 Americans (increasing ~15% annually) and it is associated with unacceptably high rates of morbidity and mortality. IBD is also a significant burden on the U.S. health care system as the most effective treatments are biological drugs that are quite costly.

IBD occurs as the result of inappropriate immune responses in genetically susceptible individuals mediated by complex interactions between environmental stimuli, microbial factors, and the intestinal immune system. The hallmark of IBD is represented by excessive immune responses that mediate gastrointestinal tissue damage, either directly or through the release of soluble, pro-inflammatory mediators.

T cells are a type of immune cell that infiltrate the intestinal mucosa and are key drivers of gastrointestinal tissue damage in IBD. These cells persist and accumulate in the intestinal mucosa because normal physiologic mechanisms designed to censor or eliminate activated T cells are inoperative in the context of IBD. While the exact basis for T cell accumulation in IBD is not fully elucidated, chronic activation by microbial stimuli along with the cytokine milieu at the sites of inflammation within gastrointestinal tissue are thought to be important. Regardless of how these cells persist, enhancing T cell death in the intestinal mucosa is linked with resolution of IBD and drugs that are most effective in managing IBD function (in part), by killing pathogenic T cells resident in the gut.

Although different forms of IBD show pathophysiological and clinical differences, the therapeutic approach to managing IBD shares many common elements. Medical management of IBD is largely empirical, employing anti-inflammatory or immunosuppressive drugs. Salicylazosulfapyridine and 5-aminosalicylic acid are used to treat mild IBD and as maintenance therapy if disease remission can be achieved. Corticosteroids are used in patients with moderate to severe disease. However, clinical remission can only be obtained in ~60% of patients, and just about half of these stay in remission after treatment is discontinued. This last point is significant because long-term use of corticosteroids carries a significant risk of serious side effects.

Immunosuppressive drugs can also be used to treat moderate to severe cases of IBD, often as a replacement for steroid therapy. However, immunosuppressive drugs (e.g., azathioprine) usually cannot ensure control of symptoms, and treatment is accompanied by numerous contraindications and severe side effects.

Drugs that often show the best efficacy in treating IBD are systemically administered (via injection or infusion) monoclonal antibodies that block TNF-alpha, a pro-inflammatory cytokine overproduced during all forms of IBD (e.g., UC, CD, graft-versus-host disease, celiac disease, iatrogenic colitis such as that induced by checkpoint inhibitors, etc.). Reducing levels of TNF-alpha in the context of IBD has two consequences. First, as an inflammatory cytokine, TNF-alpha mediates tissue damage. Second, high levels of TNF-alpha help disease causing T cells to survive and blocking TNF-alpha activity eventually leads to T cell death. Indeed, the induction of cell death by anti-TNF-alpha drugs like infliximab can predict clinical improvement in patients.

Although effective, use of anti-TNF-alpha drugs is associated with severe, systemic side effects including, re-activation of latent pathogens, hypersensitivity phenomena, cancer, and the formation of autoantibodies. Some patients are inherently resistant to anti-TNF-alpha drugs and over time, almost half of all patients that do show a response, develop resistance.

From the foregoing it is clear that there is need for new drugs to treat IBD that are more effective, less toxic, less expensive, and more convenient to administer versus standard of care.

Niclosamide (5-chloro-N-(2-chloro-4-nitrophenyl)-2-hydrobenzamide) is a halogenated salicylanilide that belongs to a group of medicines known as anthelmintics. Anthelmintics are medicines used in the treatment of worm infections. Niclosamide, which has low systemic bioavailabilty and an excellent safety profile, is used to treat broad or fish tapeworm, dwarf tapeworm, and beef tapeworm infections. It is believed that Niclosamide inhibits oxidative phosphorylation and stimulates adenosine triphosphatase activity in the mitochondria of cestodes (e.g., tapeworm), killing the scolex and proximal segments of the tapeworm both in vitro and in vivo (see, Li, Y., et al., Cancer Lett. 2014 349, 8-14).

Recent studies have also identified other potential uses of niclosamide; e.g., as a potential anti cancer agent (Id.); and as an agent for treating, preventing and/or alleviating the symptoms of type II diabetes and diabetes-related disorders or complications (see, e.g., WO 2012/068274). U.S. Pat. No. 8,148,328 discloses that niclosamide enhances the oral bioavailability of certain peptides.

SUMMARY

This disclosure features chemical entities (e.g., a compound exhibiting activity as a mitochondrial uncoupling agent or a pharmaceutically acceptable salt, and/or hydrate, and/or cocrystal, and/or drug combination thereof; e.g., a compound, such as niclosamide or a pharmaceutically acceptable salt, and/or hydrate, and/or cocrystal, and/or drug combination thereof; e.g., a compound, such as a niclosamide analog, or a pharmaceutically acceptable salt, and/or hydrate, and/or drug combination, and/or cocrystal thereof) that are useful, e.g., for treating one or more symptoms of a pathology characterized by an abnormal inflammatory response (e.g., inflammatory bowel diseases) in a subject (e.g., a human). This disclosure also features compositions as well as other methods of using and making the same.

This disclosure is based, in part, on the finding that niclosamide kills pathogenic T cells isolated from IBD patients and is effective in murine models of IBD. While not wishing to be bound by theory, it is believed that the chemical entities described herein (e.g., niclosamide or a pharmaceutically acceptable salt and/or hydrate and/or cocrystal thereof) uncouple mitochondrial respiration from oxidative phosphorylation in one or more T cells, thereby disrupting the mitochondrial energy cycle in the one or more T cells and inducing cell death of the one or more T cells (e.g., activated T cells). It has been surprisingly found that the chemical entities described herein selectively target and kill T cells associated with pathologies characterized by an abnormal inflammatory response (e.g., pathogenic T cells in the intestinal mucosa).

The chemical entities, methods, and compositions described herein not only provide treatment options that are highly efficient and effective at killing T cells, but also ones that address the toxicity, cost, and convenience issues associated with some standard methods of treatment.

In certain embodiments, the methods described herein can be carried out using niclosamide, a small molecule that has an established and good safety profile and is an FDA approved anthelmintic drug.

Additionally, the chemical entities described herein can be readily and efficiently administered locally, such that the resultant systemic bioavailability of the administered chemical entity is relatively low, and the resultant local bioavailability of the administered chemical entity is relatively high. Local (non-systemic) administration of the chemical entity at a desired area of treatment (e.g., gastrointestinal tract) significantly reduces the likelihood that a patient will experience systemic toxicities associated with some current standards of care. The foregoing can be achieved, for example, by selecting chemical entities having a relatively low oral bioavailability (F) and/or by employing formulations that are chemically and/or structurally predisposed to minimize systemic exposure of the chemical entity (e.g., the formulations can be designed to release the chemical entity at a pH that is present in the target area of the GI tract).

In view of the foregoing advantages and features delineated above, the chemical entities, methods, and compositions described herein are also expected to be functional in diverse patient populations and/or less sensitive to blocks in cell death mechanisms. Further, the ability to utilize traditional small molecules, such as niclosamide, can help reduce cost and facilitate patient administration.

In some embodiments, the methods and compositions described herein are suitable for use in combination therapy with various other therapeutic regimens (e.g., chemotherapy and/or radiation). In certain embodiments, the chemical entities and methods described herein can be used to treat side effects produced by such therapeutic regimens, e.g., inflammatory bowel diseases induced by chemotherapeutic immunomodulators, e.g., checkpoint inhibitors, which in some cases can be prohibitively severe. Additionally, the chemical entities, methods, and compositions described herein are also expected to be useful in certain treatment-resistant patient populations, e.g., one that is nonresponsive or resistant to treatment an anti-TNFalpha therapy (e.g., Humira, Enbrel, Remicade).

In one aspect, methods for inducing cell death of one or more T cells (e.g., in the digestive and/or gastrointestinal tract (GI), skin, eyes, or joints), of a subject are provided. The methods include contacting the one or more T cells with an effective amount of a chemical entity (e.g., a compound exhibiting activity as a mitochondrial uncoupling agent or a pharmaceutically acceptable salt and/or hydrate and/or cocrystal thereof; e.g., a compound, such as niclosamide or a pharmaceutically acceptable salt and/or hydrate and/or cocrystal thereof; e.g., a compound, such as a niclosamide analog, or a pharmaceutically acceptable salt and/or hydrate and/or cocrystal thereof) as defined anywhere herein.

In another aspect, methods for treating a subject having a condition associated with unregulated (abnormal, elevated) recruitment and/or retention of one or more T cells (e.g., at the digestive and/or gastrointestinal tract (GI), skin, eyes, or joints) of the subject are provided. The methods include contacting the one or more T cells with an effective amount of a chemical entity (e.g., a compound exhibiting activity as a mitochondrial uncoupling agent or a pharmaceutically acceptable salt and/or hydrate and/or cocrystal thereof; e.g., a compound, such as niclosamide or a pharmaceutically acceptable salt and/or hydrate and/or cocrystal thereof; e.g., a compound, such as a niclosamide analog, or a pharmaceutically acceptable salt and/or hydrate and/or cocrystal thereof) as defined anywhere herein.

In a further aspect, methods for treating a subject having a condition associated with unregulated (abnormal, elevated) activation of one or more T cells (e.g., in the digestive and/or gastrointestinal tract (GI), skin, eyes, or joints) of the subject are provided. The methods include contacting the one or more activated T cells with an effective amount of a cocrystal comprising (i) a mitochondrial uncoupling agent or a pharmaceutically acceptable salt and/or hydrate thereof; and (ii) one or more pharmaceutically acceptable coformers as defined anywhere herein.

In aspect, methods for treating a condition (or one or more symptoms thereof) characterized by an abnormal inflammatory response in a subject in need thereof are provided (e.g., an autoimmune disorder, e.g., an inflammatory bowel disease). The methods include administering to the subject an effective amount of a chemical entity (e.g., a compound exhibiting activity as a mitochondrial uncoupling agent or a pharmaceutically acceptable salt and/or hydrate and/or cocrystal thereof; e.g., a compound, such as niclosamide or a pharmaceutically acceptable salt and/or hydrate and/or cocrystal thereof; e.g., a compound, such as a niclosamide analog, or a pharmaceutically acceptable salt and/or hydrate and/or cocrystal thereof) as defined anywhere herein.

In another aspect, methods for treating a condition (or one or more symptoms thereof) characterized by an abnormal inflammatory response in a subject in need thereof are provided (e.g., an autoimmune disorder, e.g., an inflammatory bowel disease). The methods include topically and locally administering to the subject an effective amount of a chemical entity (e.g., a compound exhibiting activity as a mitochondrial uncoupling agent or a pharmaceutically acceptable salt and/or hydrate and/or cocrystal thereof; e.g., a compound, such as niclosamide or a pharmaceutically acceptable salt and/or hydrate and/or cocrystal thereof; e.g., a compound, such as a niclosamide analog, or a pharmaceutically acceptable salt and/or hydrate and/or cocrystal thereof) as defined anywhere herein.

In a further aspect, methods for treating autoimmune colitis (or one or more symptoms thereof) in a subject are provided. The methods include topically and locally administering to the subject an effective amount of a chemical entity (e.g., a compound exhibiting activity as a mitochondrial uncoupling agent or a pharmaceutically acceptable salt and/or hydrate and/or cocrystal thereof; e.g., a compound, such as niclosamide or a pharmaceutically acceptable salt and/or hydrate and/or cocrystal thereof; e.g., a compound, such as a niclosamide analog, or a pharmaceutically acceptable salt and/or hydrate and/or cocrystal thereof) as defined anywhere herein.

In one aspect, methods for treating a condition (or one or more symptoms thereof) selected from the group consisting of celiac disease, irritable bowel syndrome, mucositis, uveitis, collagenous colitis, lymphocytic colitis, microscopic colitis, radiation enteritis, rheumatoid arthritis, lupus, scleroderma, psoriasis, cutaneous T-cell lymphoma, acute graft vs. host disease and chronic graft vs. host disease in a subject are provided. The methods include topically and locally administering to the subject an effective amount of a chemical entity (e.g., a compound exhibiting activity as a mitochondrial uncoupling agent or a pharmaceutically acceptable salt and/or hydrate and/or cocrystal thereof; e.g., a compound, such as niclosamide or a pharmaceutically acceptable salt and/or hydrate and/or cocrystal thereof; e.g., a compound, such as a niclosamide analog, or a pharmaceutically acceptable salt and/or hydrate and/or cocrystal thereof) as defined anywhere herein.

In one aspect, a cocrystal is provided, which includes: (i) a mitochondrial uncoupling agent or a pharmaceutically acceptable salt and/or hydrate thereof; and (ii) one or more pharmaceutically acceptable coformers.

Definitions

To facilitate understanding of the disclosure set forth herein, a number of terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs. Each of the patents, applications, published applications, and other publications that are mentioned throughout the specification and the attached appendices are incorporated herein by reference in their entireties.

The term "digestive tract" is understood to include the mouth, pharynx, esophagus, stomach, small intestine (duodenum, jejunum, ileum), large intestine (cecum, colon, rectum) and anus.

The term "oral cavity" is understood to include the mouth, the pharynx and the esophagus.

The term "gastrointestinal tract", or "GI tract" is understood to include the stomach, small intestine (duodenum, jejunum, ileum), large intestine (cecum, colon, rectum) and anus.

The term "acceptable" with respect to a formulation, composition or ingredient, as used herein, means having no persistent detrimental effect on the general health of the subject being treated.

"API" refers to an active pharmaceutical ingredient.

The terms "effective amount" or "therapeutically effective amount," as used herein, refer to a sufficient amount of a chemical entity (e.g., a compound exhibiting activity as a mitochondrial uncoupling agent or a pharmaceutically acceptable salt and/or hydrate and/or cocrystal thereof; e.g., a compound, such as niclosamide or a pharmaceutically acceptable salt and/or hydrate and/or cocrystal thereof; e.g., a compound, such as a niclosamide analog, or a pharmaceutically acceptable salt and/or hydrate and/or cocrystal thereof) being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

The term "excipient" or "pharmaceutically acceptable excipient" means a pharmaceutically-acceptable material, composition, or vehicle, such as a liquid or solid filler, diluent, carrier, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy,* 21*st ed.* Lippincott Williams & Wilkins: Philadelphia, Pa., 2005*; Handbook of Pharmaceutical Excipients, 6th ed.*; Rowe et al., Eds.; The Pharmaceutical Press and the American Pharmaceutical Association: 2009*; Handbook of Pharmaceutical Additives,* 3rd ed.; Ash and Ash Eds.; Gower Publishing Company: 2007*; Pharmaceutical Preformulation and Formulation,* 2nd ed Gibson Ed.; CRC Press LLC: Boca Raton, Fla., 2009.

The term "pharmaceutically acceptable salt" refers to a formulation of a compound that does not cause significant irritation to an organism to which it is administered and does not abrogate the biological activity and properties of the compound. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. In some instances, pharmaceutically acceptable salts are obtained by reacting a compound having acidic group described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, M-methyl-D-glucamine, tris(hydroxymethyl)methylamine, and salts with amino acids such as arginine, lysine, and the like, or by other methods previously determined. The pharmacologically acceptable salt s not specifically limited as far as it can be used in medicaments. Examples of a salt that the compounds described hereinform with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

The term "pharmaceutical composition" refers to a mixture of a compound described herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to: rectal, oral, intravenous, aerosol, parenteral, ophthalmic, pulmonary, and topical administration.

The term "subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

The terms "treat," "treating," and "treatment," in the context of treating a disease or disorder, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof. Often, the beneficial effects that a subject derives from a therapeutic agent do not result in a complete cure of the disease, disorder or condition.

As used herein, the terms "alkyl" and the prefix "alk-" are inclusive of both straight chain and branched chain groups and of cyclic groups, i.e., cycloalkyl. A "$C_{2-10}$ alkenyl" refers to a branched or unbranched hydrocarbon group containing one or more double bonds and having from 2 to 10 carbon atoms. A "$C_{1-10}$ alkynyl" refers to a branched or unbranched hydrocarbon group containing one or more triple bonds and having from 2 to 10 carbon atoms. A "$C_{2-6}$ heterocyclyl" refers to a stable 5- to 7-membered monocyclic or 7- to 14-membered bicyclic heterocyclic ring that is saturated, partially unsaturated or unsaturated (aromatic), and that consists of 2 to 6 carbon atoms and 1, 2, 3 or 4 heteroatoms independently selected from the group consisting of N, O, and S and including any bicyclic group in which any of the above-defined heterocyclic rings is fused to a benzene ring. A "$C_{6-12}$ aryl" refers to an aromatic group having a ring system comprised of carbon atoms with conjugated electrons (e.g., phenyl). A "$C_{7-14}$ alkaryl" refers to an alkyl substituted by an aryl group (e.g., benzyl, phenethyl, or 3,4-dichlorophenethyl) having from 7 to 14 carbon atoms A "$C_{3-10}$ alkheterocyclyl" refers to an alkyl substituted heterocyclic group. A "$C_{1-10}$ heteroalkyl" refers to a branched or unbranched alkyl, alkenyl, or alkynyl group having from 1 to 10 carbon atoms in addition to one or more heteroatoms, where one or more methylenes ($CH_2$) or methines (CH) are replaced by nitrogen, oxygen, sulfur, carbonyl, thiocarbonyl, phosphoryl, or sulfonyl. The term "acyl" refers to a chemical moiety with the formula R—C(O)—, where R is selected from $C_{1-10}$ alkyl, $C_{1-10}$ alkenyl, $C_{1-10}$ alkynyl, $C_{2-6}$ heterocyclyl, $C_{6-12}$ aryl, $C_{7-14}$ alkaryl, $C_{3-10}$ alkheterocyclyl, $C_{1-10}$ heteroalkyl, and the like. In certain embodiments, acyl is a chemical moiety with the formula R—C(O)—, where R is selected from $C_{1-10}$ alkyl, $C_{1-10}$ alkenyl, $C_{1-10}$ alkynyl, $C_{2-6}$ heterocyclyl, $C_{6-12}$ aryl, $C_{7-14}$ alkaryl, $C_{3-10}$ alkheterocyclyl, and $C_{1-10}$ heteroalkyl. Each of the foregoing groups can be independently substituted or unsubstituted. Illustrative substituents include alkoxy, aryloxy, sulfhydryl, alkylthio, arylthio, halide, hydroxyl, fluoroalkyl, perfluoroalkyl, amino, aminoalkyl, disubstituted amino, quaternary amino, hydroxyalkyl, carboxyalkyl, and carboxyl groups.

The details of one or more embodiments of the invention are set forth in the accompanying drawings and the description below. Other features and advantages of the invention will be apparent from the description and drawings, and from the claims.

DETAILED DESCRIPTION

Figure 1:
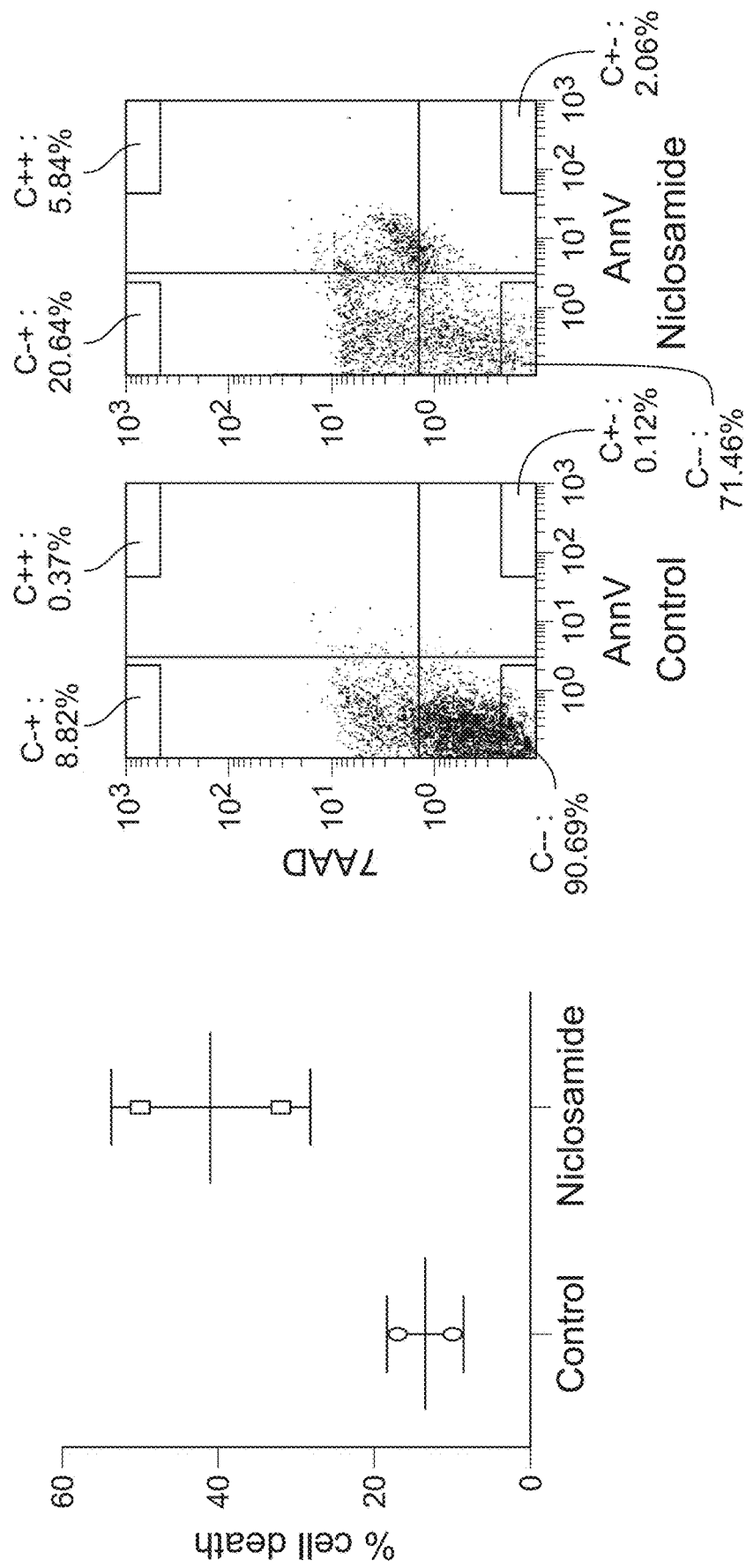
FIG. 1 contains graphs showing that Niclosamide induces cell death in lamina propria T cell from active IBD. LPMC (lamina propria mononuclear cells) from IBD subjects were isolated from macroscopically inflamed intestinal area and treated with DMSO or niclosamide (10 µM) for 16 hours. Cell death in lamina propria T cell (CD3+) was determined by measuring 7-AAD staining by flow cytometry.

This disclosure features chemical entities (e.g., a compound exhibiting activity as a mitochondrial uncoupling agent or a pharmaceutically acceptable salt, and/or hydrate, and/or cocrystal, and/or drug combination thereof; e.g., a compound, such as niclosamide or a pharmaceutically acceptable salt, and/or hydrate, and/or cocrystal, and/or drug combination thereof; e.g., a compound, such as a niclosamide analog, or a pharmaceutically acceptable salt, and/or hydrate, and/or drug combination, and/or cocrystal thereof) that are useful, e.g., for treating one or more symptoms of a pathology characterized by an abnormal inflammatory response (e.g., inflammatory bowel diseases) in a subject (e.g., a human). This disclosure also features compositions as well as other methods of using and making the same.

Chemical Entities

Evaluating Chemical Entities for Activity as Mitochondrial Uncoupling Agents

While not wishing to be bound by theory, it is believed that the chemical entities described herein are capable of uncoupling mitochondrial respiration from oxidative phosphorylation in one or more T cells, thereby disrupting the mitochondrial energy cycle in the one or more T cells, and inducing cell death of the one or more T cells (e.g., activated T cells). The ability of a chemical entity to uncouple mitochondrial respiration from oxidative phosphorylation in one or more T cells can be evaluated using conventional assays that are known in the art.

By way of example, the Jurkat T cell model can be used to study the potential effects of compounds on T cells in vitro. This cell line allows investigation of stimuli and mechanisms that regulate T cell mitochondrial function and survival. As T cells, Jurkats have a lymphocyte appearance and replicate in culture in suspension. Jurkats also contain respiring mitochondria and, as such, response to mitochondrial uncouplers, e.g., niclosamide, may be assessed. Uncoupling is identified and quantified by a detecting a drop in the electrochemical gradient across the mitochondrial inner membrane ($\Delta\Psi m$) that is not associated with a corresponding increase in oxidative phosphorylation. Experiments to detect changes in $\Delta\Psi m$ were performed by including conditions in which a concentration of oligomycin was added to irreversibly inhibit the $F_1F_0$-ATPase and block oxidative phosphorylation to demonstrate that the fall in $\Delta\Psi m$ represents uncoupling since it occurred independent of an increase in mitochondrial oxidative phosphorylation. See Example 1.

As another example, lamina propria mononuclear cells (LPMC) in the human intestine are comprised in part by T cells which mediate physiological and pathological processes including inflammatory bowel disease LPMCs can be isolated from human tissue biopsies. After isolation LPMCs T cells remain viable ex vivo under appropriate culture conditions for periods of time that allow ex vivo experiments. These cells can be used to investigate mechanisms that regulate their mitochondrial function and survival. They contain respiring mitochondria and as such their response to mitochondrial uncouplers such as niclosamide may be assessed. This cellular model can be used in conjunction with oligomycin that blocks oxidative phosphorylation and TMRM to monitor $\Delta\Psi m$ as described in Example 1 See Example 2.

Chemical entities that exhibit mitochondrial uncoupling agent activity can also include those that exhibit mild uncoupling, which refers to a level of proton leak that is compensated for by increased mitochondrial oxygen consumption so as to prevent a significant drop in the transmembrane potential.

Physicochemical Properties of Chemical Entities

In some embodiments, it is advantageous when the resultant systemic bioavailability of the administered chemical entity is relatively low, and the resultant local bioavailability of the administered chemical entity is relatively high. The foregoing can be achieved, for example, by selecting chemical entities having a relatively low oral bioavailability (F), wherein:

$$F=Fa \times Fg \times Fh$$

in which Fa=fraction absorbed; Fg=fraction escaping gut metabolism; and Fh=fraction escaping hepatic metabolism (see Filipski, K. J., et al., *Current Topics in Medicinal Chemistry*, 2013, 13, 776-802). As the skilled artisan will appreciate, the degree of oral bioavailability can be influenced by various physicochemical attributes, such as molecular weight ("MW"), logP, number of hydrogen bond donors ("HBD"), number of hydrogen bond acceptors ("HBA"), number of rotatable bonds ("RB"), and polar surface area ("PSA"). It has been recognized that good oral bioavailability is typically observed in compounds having the following attributes: MW≤500, LogP≤5, HBD≤5, HBA≤10, rotatable bonds (RB)≤10, PSA≤140 (Id). Accordingly, a non-limiting strategy for designing and selecting chemical entities having a relatively low oral bioavailability (F) can include selecting physicochemical attributes that confer properties outside of the preferred oral drug space (Id).

In some embodiments, the chemical entities described herein (including their pharmaceutically acceptable salts and/or hydrates and/or cocrystals thereof) have an oral bioavailability (F) of less than about 50%, or less than about 40%, or less than about 30%, or less than about 20%, or less than about 10%, or less than about 5%, or less than about 2%, or less than about 1%. In certain embodiments, the chemical entities described herein have an oral bioavailability (F) of less than about 20%, e.g., less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, less than about 1%, or less than about 0.5%.

In some embodiments, the chemical entities described herein (including their pharmaceutically acceptable salts and/or hydrates and/or cocrystals thereof) have a relatively low aqueous solubility. Low aqueous solubility refers to a compound having a solubility in water which is less than or equal to 10 mg/mL, when measured at 20° C. In certain embodiments, the chemical entities described herein have aqueous solubility of less than or equal to 900, 800, 700, 600, 500, 400, 300, 200 150 100, 90, 80, 70, 60, 50, 40, 30, micrograms/mL, or further 10, 5 or 1 micrograms/mL, or further 900, 800, 700, 600, 500, 400, 300, 200 150, 100 90, 80, 70, 60, 50, 40, 30, 20, or 10 ng/mL, or less than 10 ng/mL when measured at 20° C.

In some embodiments, the chemical entities described herein (including their pharmaceutically acceptable salts and/or hydrates and/or cocrystals thereof) have a relatively low drug permeability. Permeability measurements are based indirectly on the extent of absorption of a drug substance in humans and directly on the measurement of rates of mass transfer across human intestinal membrane. Alternatively, non-human systems capable of predicting drug absorption in humans can be used (such as in-vitro culture methods). A drug substance is considered highly permeable when the extent of absorption in humans is determined to be about 90% or more of the administered dose based on a mass-balance determination or in comparison to an intravenous dose. Otherwise, the drug substance is considered to be poorly permeable (see, e.g., https://books.google.com/books?id=4cfzT2ZY8hUC&pg=PA102&lpg=PA102&dq=low+permeability+drug+definition&source=bl&ots=WXEDT3C0sL&sig=g1laf7e47KJ-SSV4loN8RSs_sM&hl=en&sa=X&ved=0CFAQ6AEwBmoVChMIrv_6oL7FxwIVxBmSCh02ugoi#v=onepaae&q=low%20permeability%20drug%20definition&f=false).

In some embodiments, the chemical entities described herein can be a BCS class n drug, or pharmaceutically acceptable salt and/or hydrate and/or cocrystal thereof. In other embodiments, the chemical entities described herein can be a BCS class IV drug, or pharmaceutically acceptable salt and/or hydrate and/or cocrystal thereof.

Chemical Entities

Niclosamide and Niclosamide Analogs

In some embodiments, the chemical entity can be niclosamide or a pharmaceutically acceptable salt and/or hydrate thereof; e.g., a compound, such as a niclosamide analog, or a pharmaceutically acceptable salt and/or hydrate. Niclosamide analogues refer to compounds, in which one or more atoms, functional groups, or substructures in niclosamide is/are replaced with one or more different atoms, groups, or substructures.

In certain embodiments, the chemical entity can be a compound having formula I:

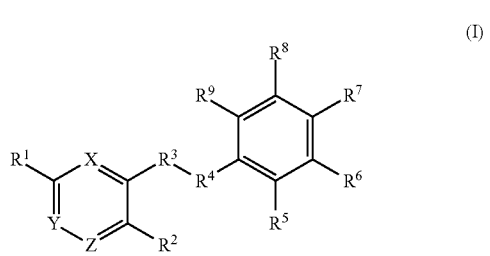

(I)

where X is N or $CR^{10}$; Y is N or $CR^{11}$; Z is N or $CR^{12}$; and each of $R^1$, $R^2$, $R^5$, $R^6$, $R^7$, $R^8$, $R^9$, $R^{10}$, $R^{11}$ and $R^{12}$ is independently selected from H, halide (F, Cl, Br, or I), $NO_2$, OH, $OR^{13}$, $SR^{14}$, $NR^{15}R^{16}$, CN, $CF_3$, $C_{1-10}$ alkyl, $C_{2-10}$ alkenyl, $C_{2-10}$ alkynyl, $C_{2-6}$ heterocyclyl, $C_{6-12}$ aryl, $C_{7-14}$alkaryl, $C_{3-10}$ alkheterocyclyl, $C_{1-10}$ heteroalkyl, or is described by one of the following formulas:

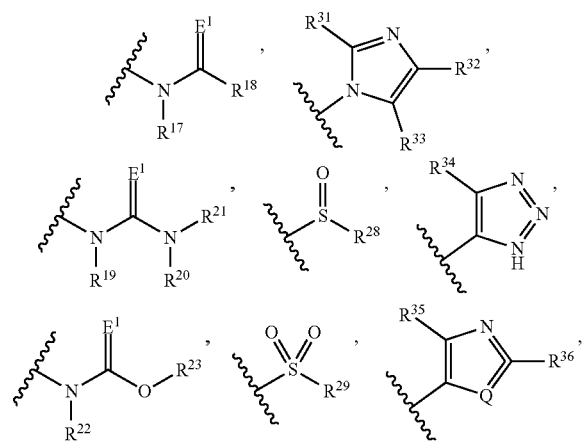

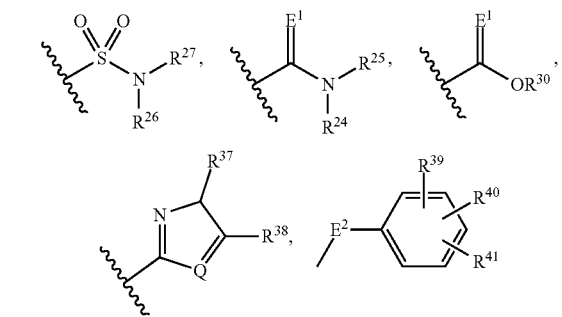

In compounds of formula I, $R^3$ and $R^4$ are independently selected from the group consisting of C=O, C=S, $C=NR^{42}$, NH, $NR^{43}$, $CHOR^{44}$, $CH_2$, and the like Groups $R^2$ and $R^4$; X and $R^4$; $R^5$ and $R^3$; $R^9$ and $R^3$ may combine to form a six-membered ring, using connections described by one of the groups:

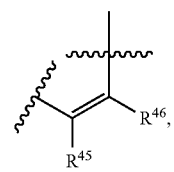

XV

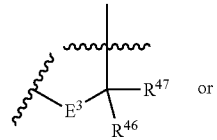

XVI

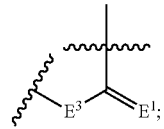

XVII

For compounds of formula I, each $E^1$ is independently O, S, or $NR^{42}$, each $E^2$ is independently $CR^{49}R^{50}$, O or S; each $E^3$ is independently $CR^{51}R^{52}$, O, S, or $NR^{53}$; each Q is, independently, O, S, or $NR^{54}$. $R^{13}$ and $R^{14}$ are each independently, acyl, $C_{1-10}$ alkyl, $C_{2-10}$ alkenyl, $C_{2-10}$alkynyl, $C_{2-6}$, heterocyclyl, $C_{6-12}$ aryl, $C_{7-14}$alkaryl, $C_{3-10}$alkheterocyclyl, $C_{1-10}$ heteroalkyl; $R^{18}$, $R^{23}$, $R^{28}$, $R^{29}$, $R^{30}$, $R^{42}$, $R^{54}$ are each, independently, $C_{1-10}$ alkyl, $C_{1-10}$ alkenyl, $C_{2-10}$alkynyl, $C_{2-6}$ heterocyclyl, $C_{6-12}$ aryl, $C_{7-14}$alkaryl, $C_{3-10}$alkheterocyclyl, $C_{1-10}$ heteroalkyl; $R^{15}$, $R^{16}$, $R^{17}$, $R^{19}$, $R^{20}$, $R^{21}$, $R^{22}$, $R^{24}$, $R^{25}$, $R^{26}$, $R^{27}$, $R^{43}$, $R^{44}$, $R^{45}$, $R^{46}$, $R^{47}$, $R^{48}$, $R^{51}$, $R^{52}$, and $R^{53}$ are each, independently, H, $C_{1-10}$ alkyl, $C_{2-10}$ alkenyl, $C_{2-10}$alkynyl, $C_{2-6}$ heterocyclyl, $C_{6-12}$ aryl, $C_{7-14}$ alkaryl, $C_{3-10}$alkheterocyclyl, $C_{1-10}$ heteroalkyl; $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{49}$, and $R^{50}$ are each, independently, H, halide, $NO_2$, CN, $CF_3$, $C_{1-10}$ alkyl, $C_{2-10}$ alkenyl, $C_{2-10}$alkynyl, $C_{2-6}$ heterocyclyl, $C_{6-12}$ aryl, $C_{7-14}$ alkaryl, $C_{3-10}$alkheterocyclyl, or $C_{1-10}$ heteroalkyl.

In certain embodiments, the chemical entity can be a compound having any one of formulas XVIII-XXI:

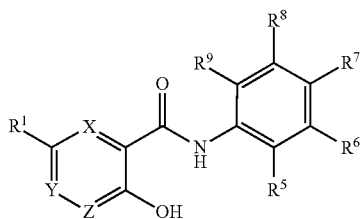

VXIII

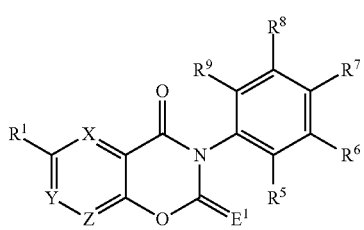

XIX

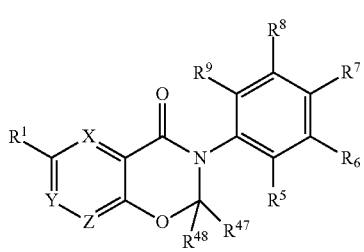

XX

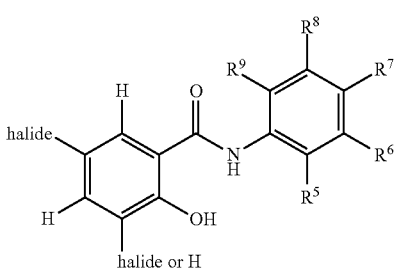

XXI wherein X, Y, Z, E$^1$, R$^1$, R$^5$, R$^6$, R$^7$, R$^8$, R$^9$, R$^{47}$, and R$^{48}$ are as defined above.

In certain embodiments, the chemical entity can be a compound having Formula XXII:

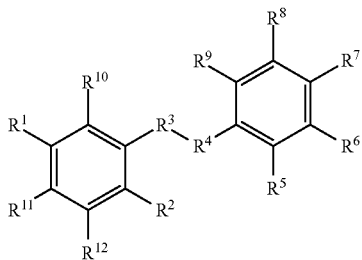

XXII wherein R$^1$, R$^2$, R$^5$, R$^6$, R$^7$, R$^8$, R$^9$, R$^{10}$, R$^{11}$ and R$^{12}$ are independently selected from the group consisting of H, halide, NO$_2$, CF$_3$, OH, acyl, CN, C$_1$-C$_{10}$ alkyl (preferably C$_1$-C$_3$ alkyl), C$_1$-C$_{10}$ heteroalkyl (preferably C$_1$-C$_3$ heteroalkyl), and wherein R$^3$ and R$^4$ are as defined above. In certain embodiments, R$^3$ is C=O, while R$^4$ is NH or R$^3$ is NH while R$^4$ is C=O. In these and certain other embodiments, only two of R$^1$, R$^2$, R$^{10}$, R$^{11}$, and R$^{12}$ are present, and one is H or OH, while the other is halogen (e.g., Cl, Br, or F). In other embodiments, one of R$^1$, R$^2$, R$^{10}$, R$^{11}$, and R$^{12}$ is H or OH, one of R$^1$, R$^2$, R$^{10}$, R$^{11}$, and R$^{12}$ is halogen (e.g., Cl, Br, or F), and the others are hydrogen.

In these and certain other embodiments, only two of R$^5$, R$^6$, R$^7$, R$^8$, and R$^9$ are present and these are NO$_2$ and halogen (e.g., Cl, Br, or F) In other embodiments, one of R$^5$, R$^6$, R$^7$, R$^8$, and R$^9$ is NO$_2$, one of R$^5$, R$^6$, R$^7$, R$^8$, and R$^9$ is halogen (e.g., Cl, Br, or F), and the rest are hydrogen. In certain embodiments niclosamide analogues include, but are not limited to niclosamide analogues in which one halogen group is relocated within the same ring or both halogen groups are relocated within the same ring niclosamides in which the nitro group is relocated within the same ring, niclosamide analogues where the hydroxyl group is relocated within the same ring niclosamide analogues where both halogen and hydroxy and/or nitro groups are relocated while keeping the substituents within the aromatic ring, compounds, except having except (3-chloro-4-nitrophenyl) in place of (2-chloro-4-nitrophenyl), niclosamide analogues having a nitro- and a hydroxyl group relocation, niclosamide analogues comprising a single halogen exchange, niclosamide analogues comprising a double halogen exchange, niclosamide analogs comprising an exchange of Cl— to Br—, niclosamide analogs comprising an exchange of Cl— to F—, and the like.

In certain embodiments the niclosamide analogues include, but are not limited to compounds according to Formula XXIII:

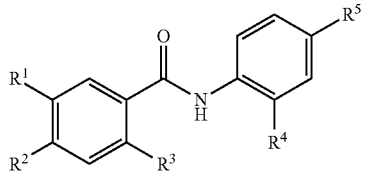

XXIII wherein R$^1$, R$^2$, R$^3$, R$^4$, and R$^5$ are independently present or absent, and when present are independently selected from the group consisting of Cl, Br, alkyl, methyl, hydroxyalkyl, and the like. These analogues are meant to be illustrative and not limiting.

In certain embodiments, the chemical entity can be a compound having formula XXIV, or a pharmaceutically acceptable salt and/or hydrate thereof:

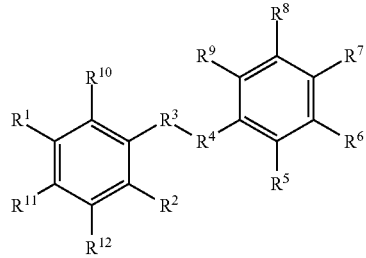

(XXIV)

wherein R$^1$, R$^2$, R$^5$, R$^6$, R$^7$, R$^8$, R$^9$, R$^{10}$, R$^{11}$ and R$^{12}$ are independently selected from the group consisting of H, halide, NO$_2$, CF$_3$, OH, acyl, CN, C$_1$-C$_{10}$ alkyl (preferably C$_1$-C$_3$ alkyl), and C$_1$-C$_{10}$ heteroalkyl (preferably C$_1$-C$_3$ heteroalkyl); and wherein R$^3$ is C=O, and R$^4$ is NH; or R$^3$ is NH, and $R^4$ is C=O, wherein at least one of $R^1$, $R^2$, $R^5$, $R^6$, $R^7$, $R^8$, $R^9$, $R^{10}$, $R^{11}$ and $R^{12}$ is other than H.

In certain of these embodiments, two of $R^1$, $R^2$, $R^{10}$, $R^{11}$ and $R^{12}$ are independently selected from halide, $NO_2$, $CF_3$, OH, acyl, CN, $C_1$-$C_{10}$ alkyl (preferably $C_1$-$C_3$ alkyl), and $C_1$-$C_{10}$ heteroalkyl (preferably $C_1$-$C_3$ heteroalkyl), and the others are H; and two of $R^5$, $R^6$, $R^7$, $R^8$, and $R^9$ are independently selected from halide, $NO_2$, $CF_3$, OH, acyl, CN, $C_1$-$C_{10}$ alkyl (preferably $C_1$-$C_3$ alkyl), and $C_1$-$C_{10}$ heteroalkyl (preferably $C_1$-$C_3$ heteroalkyl), and the others are H.

In certain embodiments, the chemical entity can be a compound having formula XXV, or a pharmaceutically acceptable salt and/or hydrate thereof.

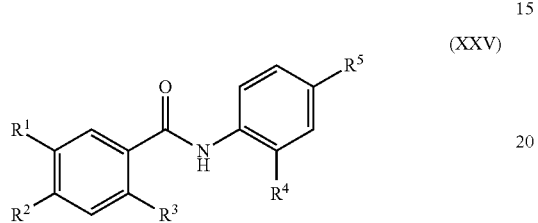

(XXV)

wherein one or more of $R^1$, $R^2$, $R^3$, $R^4$, and $R^5$ is halide, $NO_2$, $CF_3$, OH, acyl, CN, $C_1$-$C_{10}$ alkyl (preferably $C_1$-$C_3$ alkyl), or $C_1$-$C_{10}$ heteroalkyl (preferably $C_1$-$C_3$ heteroalkyl); and the others are hydrogen.

Examples of niclosamide analogues include, but are not limited to those delineated in Tables 1-3.

TABLE 1

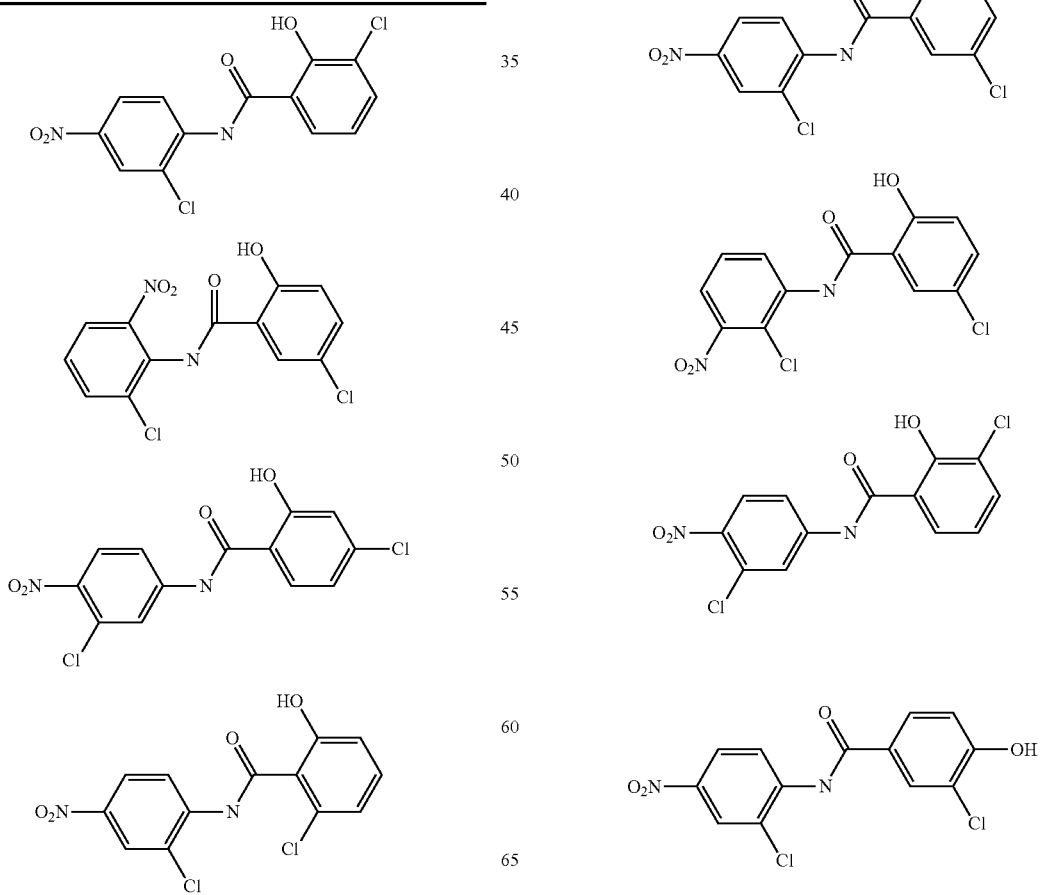

TABLE 1-continued

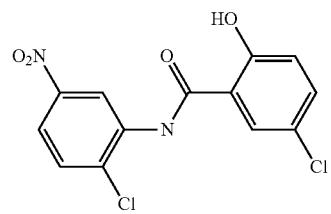 [SMILES: O=C(Nc1cc([N+](=O)[O-])ccc1Cl)c1cc(Cl)ccc1O]

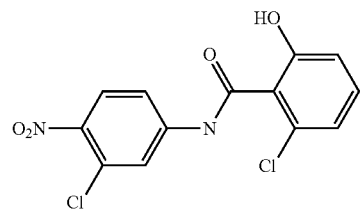 [SMILES: O=C(Nc1ccc([N+](=O)[O-])c(Cl)c1)c1c(O)cccc1Cl]

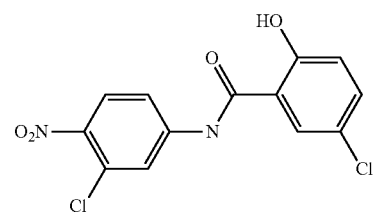 [SMILES: O=C(Nc1ccc([N+](=O)[O-])c(Cl)c1)c1cc(Cl)ccc1O]

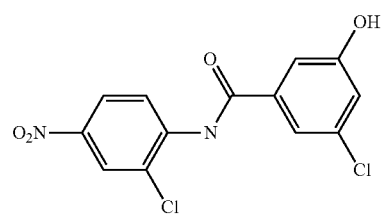

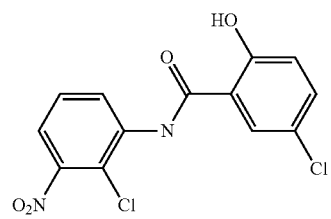 [SMILES: O=C(Nc1cccc([N+](=O)[O-])c1Cl)c1cc(Cl)ccc1O]

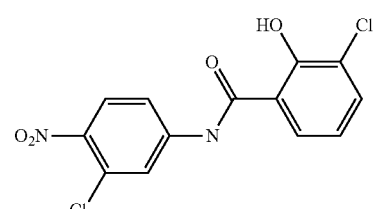

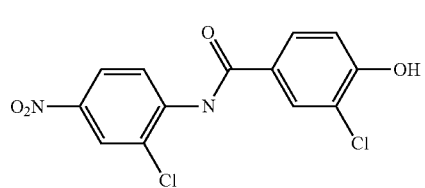 [SMILES: O=C(Nc1ccc([N+](=O)[O-])cc1Br)c1ccc(O)c(Cl)c1]

TABLE 1-continued
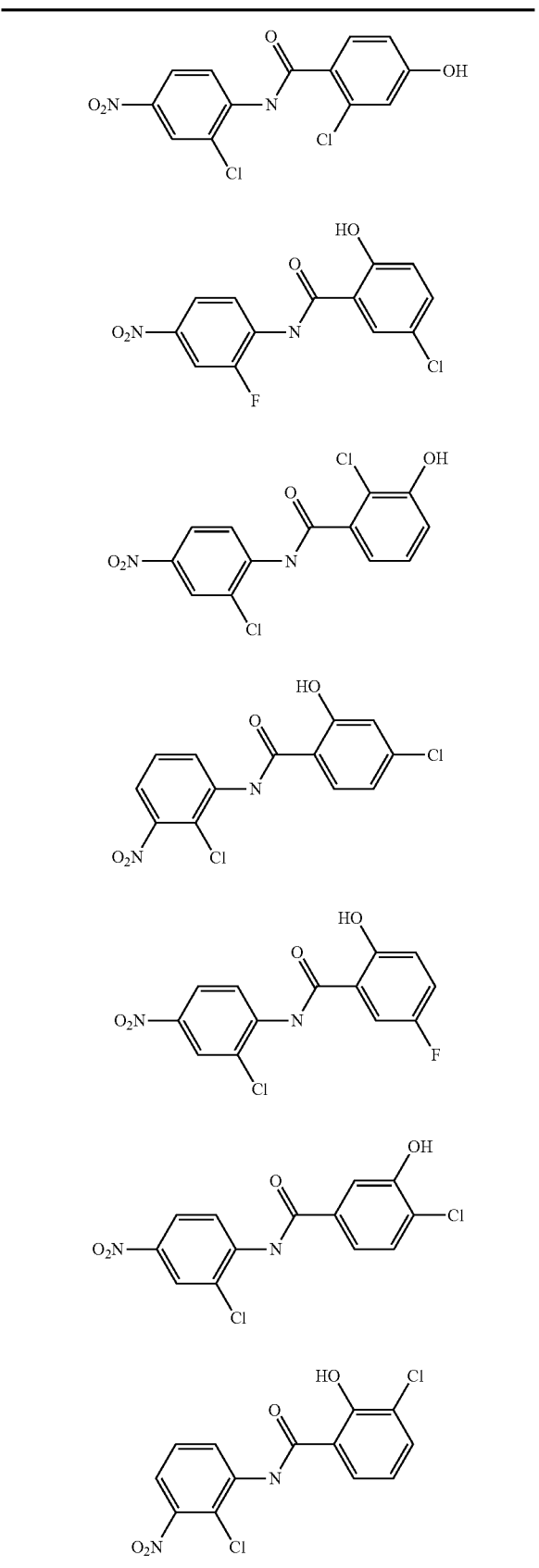
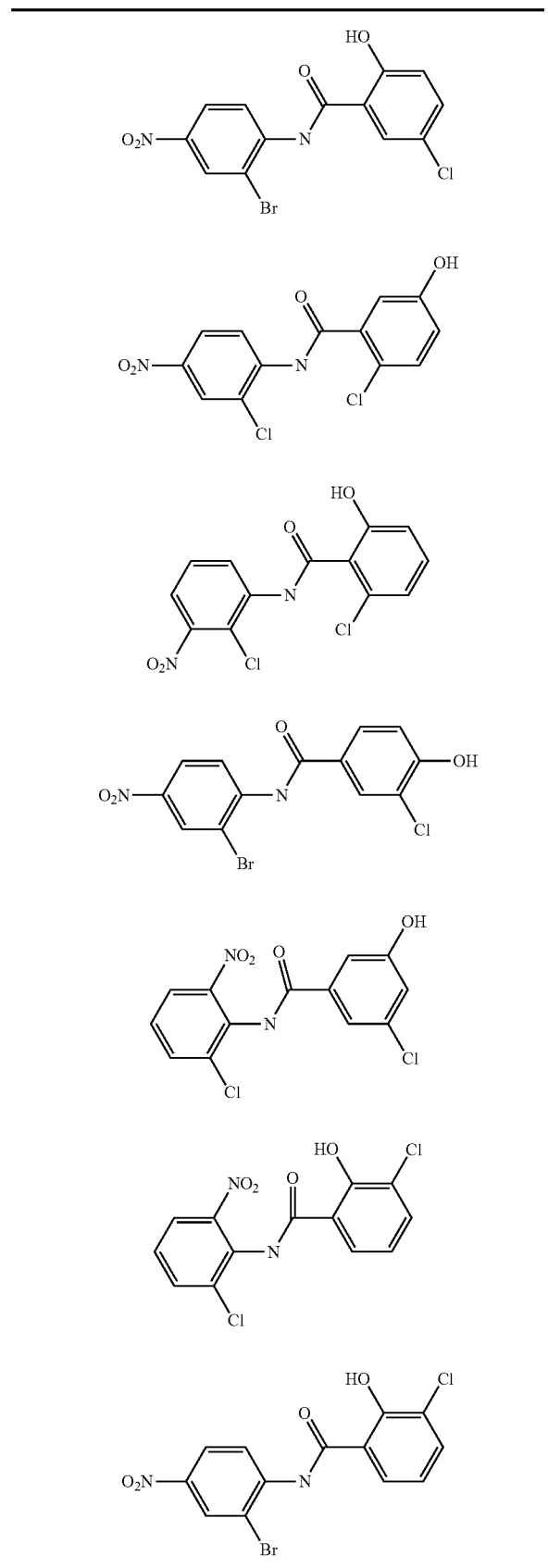

TABLE 1-continued
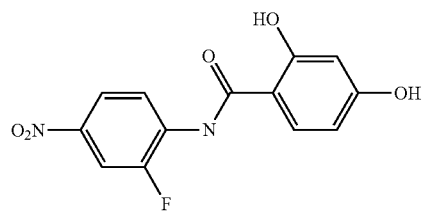 [SMILES: O=C(Nc1ccc([N+](=O)[O-])cc1F)c1ccc(O)cc1O]
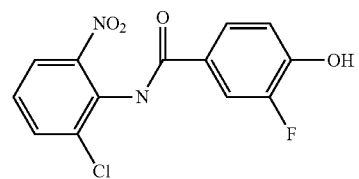 [SMILES: O=C(Nc1c(Cl)cccc1[N+](=O)[O-])c1ccc(O)c(F)c1]
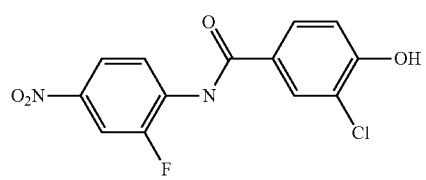
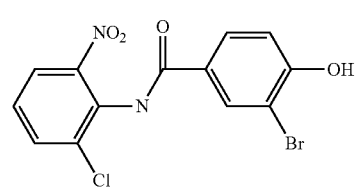
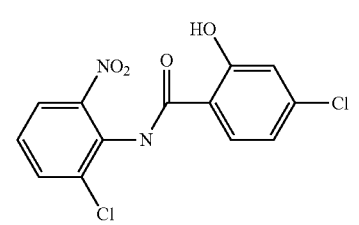 [SMILES: O=C(Nc1c(Cl)cccc1[N+](=O)[O-])c1ccc(Cl)cc1O]
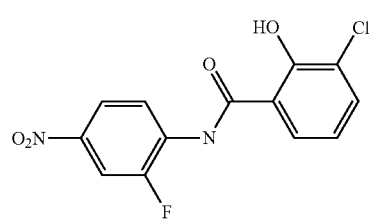
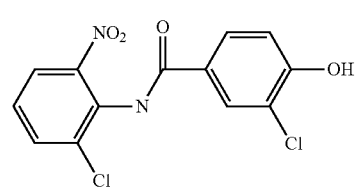
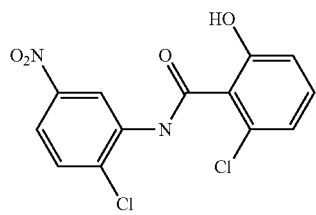 [SMILES: O=C(Nc1cc([N+](=O)[O-])ccc1Cl)c1c(O)cccc1Cl]
TABLE 1-continued
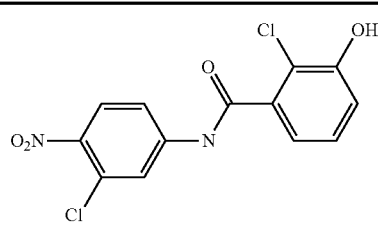
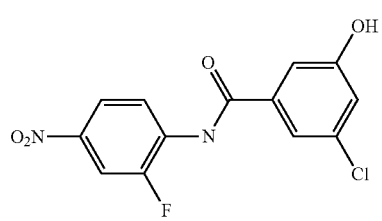
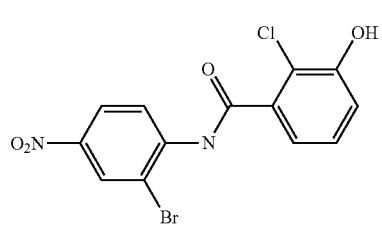 [SMILES: O=C(Nc1ccc([N+](=O)[O-])cc1Br)c1cccc(O)c1Cl]
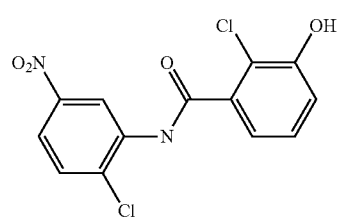 [SMILES: O=C(Nc1cc([N+](=O)[O-])ccc1Cl)c1cccc(O)c1Cl]
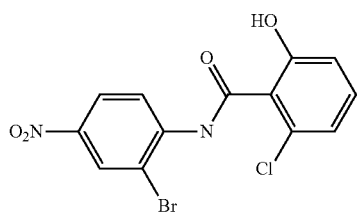 [SMILES: O=C(Nc1ccc([N+](=O)[O-])cc1Br)c1c(O)cccc1Cl]
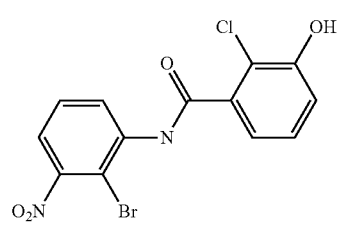 [SMILES: O=C(Nc1cccc([N+](=O)[O-])c1Br)c1cccc(O)c1Cl]
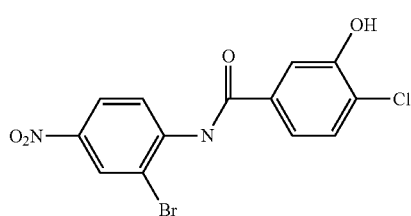 [SMILES: O=C(Nc1ccc([N+](=O)[O-])cc1Br)c1ccc(Cl)c(O)c1]

TABLE 1-continued
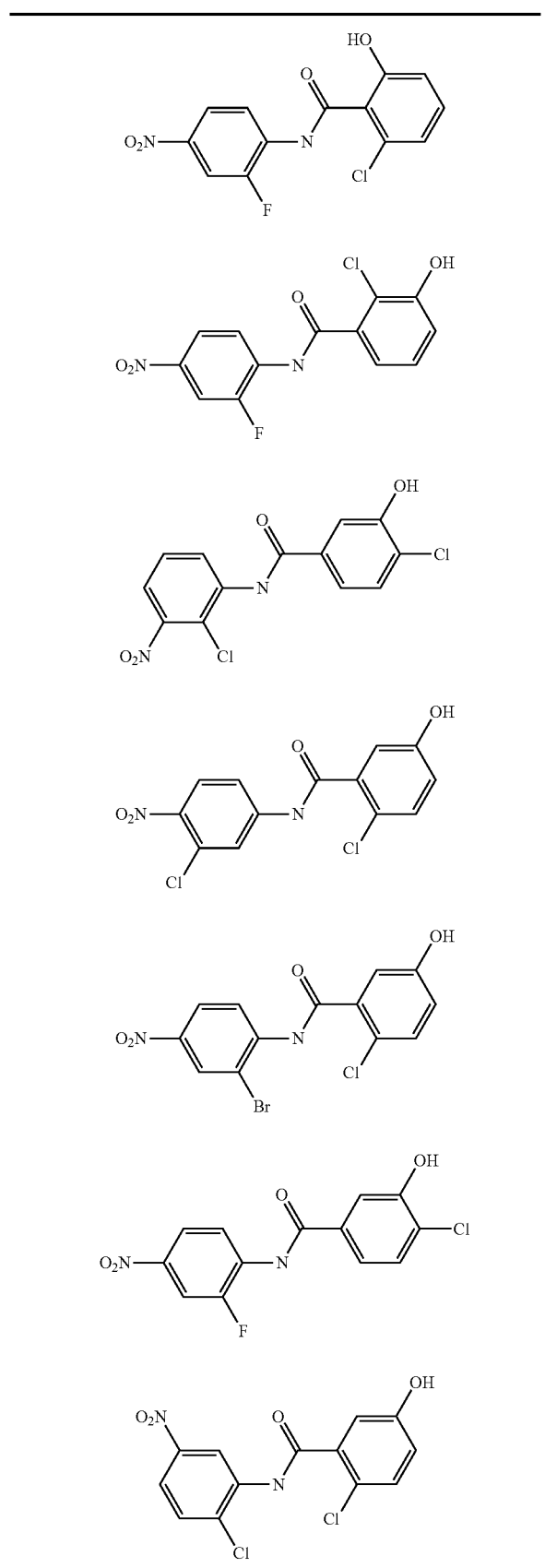
TABLE 1-continued
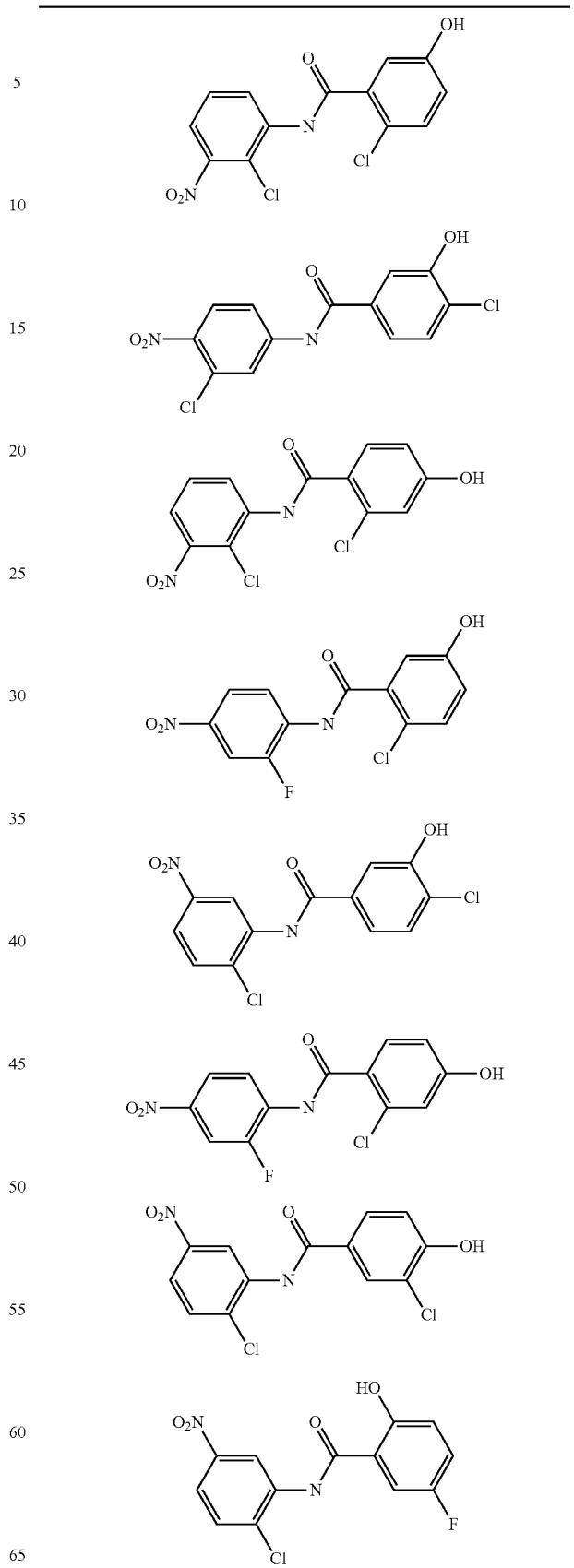

TABLE 1-continued

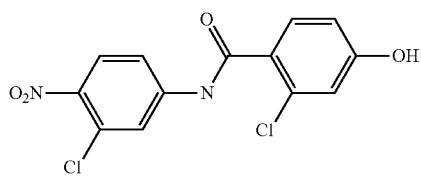 [SMILES: O=C(Nc1ccc([N+](=O)[O-])c(Cl)c1)c1ccc(O)cc1Cl]
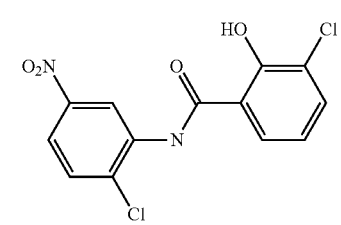 [SMILES: O=C(Nc1cc([N+](=O)[O-])ccc1Cl)c1cccc(Cl)c1O]
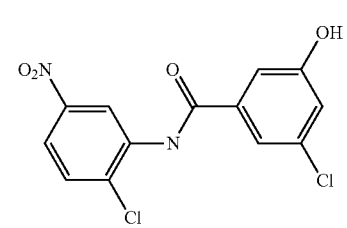 [SMILES: O=C(Nc1cc([N+](=O)[O-])ccc1Cl)c1cc(O)cc(Cl)c1]
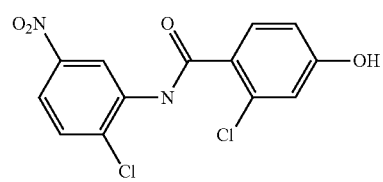 [SMILES: O=C(Nc1cc([N+](=O)[O-])ccc1Cl)c1ccc(O)cc1Cl]
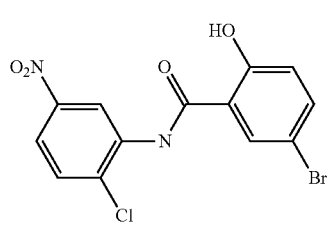
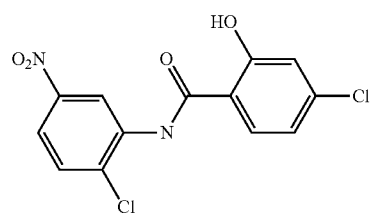 [SMILES: O=C(Nc1cc([N+](=O)[O-])ccc1Cl)c1ccc(Cl)cc1O]
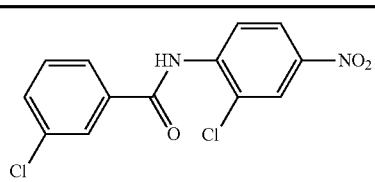

TABLE 2

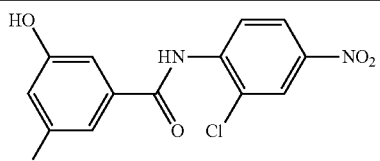
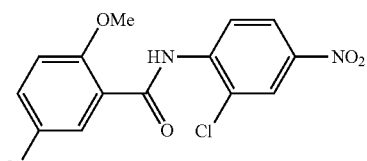
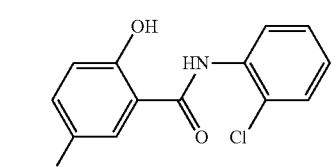
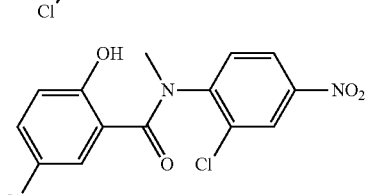

TABLE 3

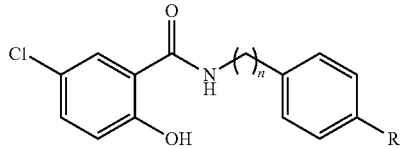

n = 0; R = Cl
n = 1; R = H
n = 2; R = H

In certain embodiments, the chemical entity can be a compound having formula (XXVI):

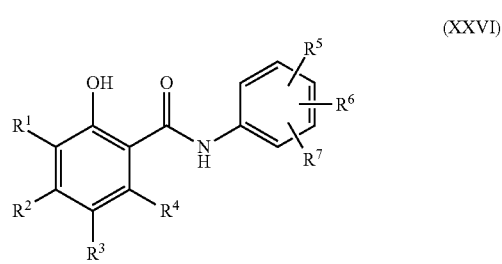

(XXVI)

$R^1$ represents $C_{1-6}$alkyl, $C_{2-6}$alkenyl, $C_{2-6}$alkynyl, $C_{3-8}$cycloalkyl, $C_{4-8}$cycloalkenyl or aryl, all of which may optionally be further substituted with $C_{1-8}$ alkyl, $C_{3-8}$cycloalkyl, $C_{4-8}$ cycloalkenyl or phenyl; or $R^1$ represents a bicyclo-$C_{4-10}$alkyl or tricyclo-$C_{4-10}$-alkyl; and wherein, when $R^1$ is $C_{3-8}$ cycloalkyl, bicyclo-$C_{4-10}$ alkyl, tricyclo-$C_{4-10}$ alkyl or aryl, $R^1$ may optionally be substituted with one or more substituents selected from halogen, hydroxy, cyano, nitro. $C_{1-6}$alkyl, $C_{2-6}$ alkenyl, $C_{2-6}$alkynyl, $C_{3-8}$ cycloalkyl, $C_{4-8}$cycloalkenyl, $C_{1-6}$alkoxy, $C_{1-6}$haloalkoxy and $C_{1-6}$haloalkyl; $R^1$ and $R^4$ independently represent hydrogen, halogen, $C_{1-6}$alkyl, $C_{2-6}$alkenyl, $C_{2-6}$alkynyl, $C_{3-8}$cycloalkyl, $C_{4-8}$cycloalkenyl or $C_{1-6}$alkoxy;

at least one of $R^5$, $R^6$ and $R^7$ represents $C_{1-6}$haloalkoxy, and the remaining of $R^5$, $R^6$ and $R^7$ independently represent hydrogen, nitro, cyano, halogen, $C_{1-6}$alkyl, $C_{2-6}$alkenyl, $C_{2-6}$alkynyl, $C_{3-8}$cycloalkyl, $C_{4-8}$ cycloalkenyl, $C_{1-6}$haloalkyl, —$OR^{10}$, —$NR^{10}R^{11}$, —$C(O)OR^{10}$, —$COR^{10}$, —$C(O)NR^{10}R^{11}$, —SH, —$S(O)_2OR^{10}$, —$S(O)_2NR^{10}R^{11}$, —$S(O)_nR^{11}$, aryl or heteroaryl, wherein said aryl or heteroaryl may optionally be substituted with one or more $C_{1-6}$alkyl, halogen, hydroxy or phenyl, $R^3$ represents hydrogen, halogen, cyano, —$OR^{10}$, —$NR^{10}R^{11}$, —$C(O)OR^{10}$, —$COR^{10}$, —$C(O)NR^{10}R^{11}$, —$S(O)_nR^{10}$, —$S(O)_2NR^{10}R^{11}$, —$NHCOR^{10}$ or —$NHSO_2R^{10}$;

n is 0, 1 or 2; and each $R^{10}$ and $R^{11}$ are selected independently from the group consisting of hydrogen, $C_{1-6}$alkyl, $C_{2-6}$alkenyl, $C_{2-6}$alkynyl, $C_{3-8}$ cycloalkyl, $C_{4-8}$ cycloalkenyl, $C_{1-6}$haloalkyl and $C_1$-$C_6$, haloalkoxy; and pharmaceutically acceptable salts, solvates and prodrugs thereof.

Further examples of niclosamide analogues include, but are not limited to those delineated in Table 4.

TABLE 4

5-Chloro-N-(4-cyano-2-trifluoromethoxy-phenyl)-3-(1,1-dimethyl-propyl)-2-hydroxy-benzamide
3-tert-Butyl-N-(4-cyano-2-trifluoromethoxy-phenyl)-2-hydroxy-5-methanesulfonyl-6-methyl-benzamide
3-Bromo-5-tert-butyl-N-(4-cyano-2-trifluoromethoxy-phenyl)-6-hydroxy-2-methyl-benzamide
5-Bromo-3-tert-butyl-N-(4-cyano-2-trifluoromethoxy-phenyl)-2-hydroxy-benzamide
5-Chloro-3-tert-butyl-N-(4-cyano-2-trifluoromethoxy-phenyl)-2-hydroxy-6-methyl-benzamide
3-tert-Butyl-N-(4-cyano-2-trifluoromethoxy-phenyl)-5-fluoro-2-hydroxy-6-methyl-benzamide
3-tert-Butyl-N-(4-cyano-2-trifluoromethoxy-phenyl)-2-hydroxy-5-methoxy-6-methyl-benzamide
3-tert-Butyl-N-(4-cyano-2-trifluoromethoxy-phenyl)-6-ethyl-2-hydroxy-5-methoxy-benzamide
3-tert-Butyl-N-(4-cyano-2-trifluoromethoxy-phenyl)-5-ethanesulfonylamino-2-hydroxy-6-methyl-benzamide
3-tert-Butyl-N-(4-cyano-2-trifluoromethoxy-phenyl)-2-hydroxy-6-methyl-5-(propane-1-sulfonylamino)-benzamide
3-tert-Butyl-N-(4-cyano-2-trifluoromethoxy-phenyl)-2-hydroxy-6-methyl-5-(propane-2-sulfonylamino)-benzamide
3-tert-Butyl-5-cyano-N-(4-cyano-2-trifluoromethoxy-phenyl-2-hydroxy-6-methyl-benzamide
3-Acetyl-5-tert-butyl-N-(4-cyano-2-trifluoromethoxy-phenyl)-6-hydroxy-2-methyl-benzamide
3-tert-Butyl-N-(4-cyano-2-trifluoromethoxy-phenyl)-2-hydroxy-5-methanesulfinyl-6-methyl-benzamide
3-tert-Butyl-N-(4-cyano-2-trifluoromethoxy-phenyl)-2-hydroxy-6-methyl-5-methylsulfanyl-benzamide
3-tert-Butyl-N-(4-cyano-2-trifluoromethoxy-phenyl)-2-hydroxy-5-methanesulfonylamino-6-methyl-benzamide; and
3-Acetylamino-5-tert-butyl-N-(4-cyano-2-trifluoromethoxy-phenyl)-6-hydroxy-2-methyl-benzamide In certain embodiments, the chemical entity can be a compound having formula

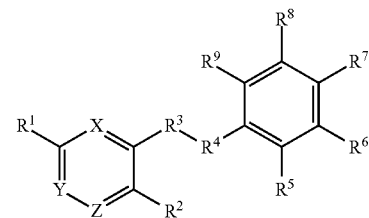

(XXVII)

where X is N or $CR^{10}$; Y is N or $CR^{11}$; Z is N or $CR^{12}$, and each of $R^1$, $R^2$, $R^5$, $R^6$, $R^7$, $R^8$, $R^9$, $R^{10}$, $R^{11}$ and $R^{12}$ is independently selected from H, halide (F, Cl, Br, or I), $NO_2$, OH, $OR^{13}$, $SR^{14}$, $NR^{15}R^{16}$, CN, $CF_3$, acyl, $C_{1-10}$ alkyl. $C_{2-10}$ alkenyl, $C_{2-10}$ alkynyl, $C_{2-6}$ heterocyclyl, $C_{6-12}$ aryl, $C_{7-14}$alkaryl, $C_{3-10}$alkheterocyclyl, $C_{1-10}$ heteroalkyl, or is described by one of the following formulas:

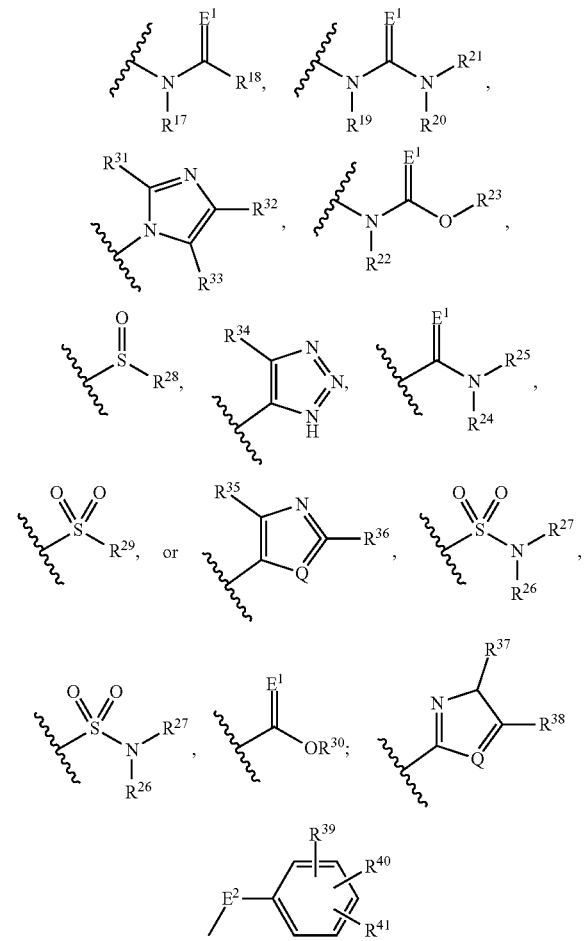

In compounds of formula XXVII, $R^3$ and $R^4$ are independently selected from the group consisting of C=O, C=S, C=$NR^{42}$, NH, $NR^{43}$, $CHOR^{44}$, $C_{1-6}$alkylene (e.g., $CH_2$), S=O, $S(O)_2$, $NHC_{1-6}$alkylene (e.g., $NHCH_2$), $C_{1-6}$alkyleneNH (e.g., $CH_2NH$), $C_{1-6}$alkylene $NR^{43}$, NHC(O), C(O)NH, Groups $R^2$ and $R^4$; X and $R^4$; $R^5$ and $R^3$; $R^9$ and $R^3$ may combine to form a six-membered ring, using connections described by one of the groups:

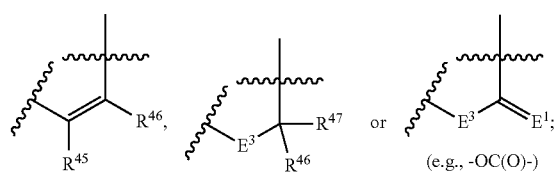
(e.g., -OC(O)-)

For compounds of formula I, each $E^1$ is independently O, S, or $NR^{42}$; each $E^2$ is independently $CR^{49}R^{50}$, O or S; each $E^3$ is independently $CR^{51}R^{52}$, O, S, or $NR^{53}$; each Q is, independently, O, S, or $NR^{54}$. $R^{13}$ and $R^{14}$ are each independently, acyl, $C(O)OC_{1-6}$ alkyl, $C_{1-10}$ alkyl, $C_{2-10}$ alkenyl, $C_{2-10}$ alkynyl, $C_{2-6}$ heterocyclyl, $C_{6-12}$ aryl, $C_{7-14}$ alkaryl, $C_{3-10}$ alkheterocyclyl, $C_{1-10}$ heteroalkyl, $R^{18}$, $R^{23}$, $R^{28}$, $R^{29}$, $R^{30}$, $R^{42}$, $R^{54}$ are each, independently, H, $C_{1-10}$ alkyl, $C_{2-10}$ alkenyl, $C_{2-10}$ alkynyl, $C_{2-6}$ heterocyclyl, $C_{6-12}$ aryl, $C_{7-14}$ alkaryl, $C_{3-10}$ alkheterocyclyl, $C_{1-10}$ heteroalkyl; $R^{15}$, $R^{16}$, $R^{17}$, $R^{19}$, $R^{20}$, $R^{21}$, $R^{22}$, $R^{24}$, $R^{25}$, $R^{26}$, $R^{27}$, $R^{43}$, $R^{44}$, $R^{45}$, $R^{46}$, $R^{47}$, $R^{48}$, $R^{51}$, $R^{52}$, and $R^{53}$ are each, independently, H, $C_{1-10}$ alkyl, $C_{2-10}$ alkenyl, $C_{2-10}$ alkynyl, $C_{2-6}$ heterocyclyl, $C_{6-12}$ aryl, $C_{7-14}$ alkaryl, $C_{3-10}$ alkheterocyclyl, $C_{1-10}$ heteroalkyl; $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{49}$, and $R^{50}$ are each, independently, H, halide, $NO_2$, CN, $CF_3$, $C_{1-10}$ alkyl, $C_{2-10}$ alkenyl, $C_{1-10}$ alkynyl, $C_{2-6}$ heterocyclyl, $C_{6-12}$ aryl, $C_{7-14}$ alkaryl, $C_{3-10}$ alkheterocyclyl, or $C_{1-10}$ heteroalkyl.

Further examples of niclosamide analogues include, but are not limited to those delineated in Table 5.

TABLE 5

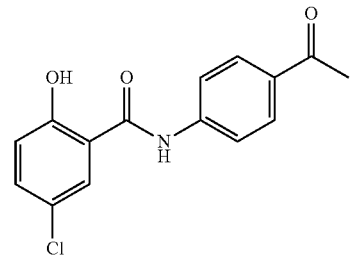 [SMILES: CC(=O)c1ccc(NC(=O)c2cc(Cl)ccc2O)cc1]

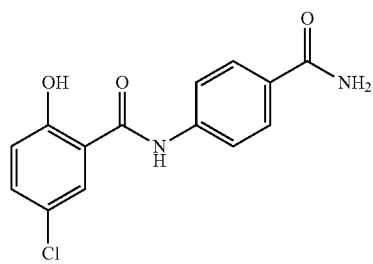 [SMILES: NC(=O)c1ccc(NC(=O)c2cc(Cl)ccc2O)cc1]

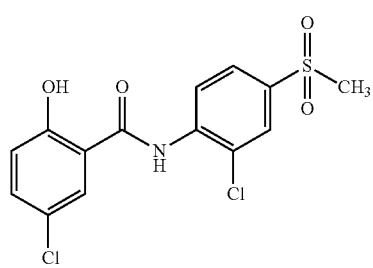 [SMILES: CS(=O)(=O)c1ccc(NC(=O)c2cc(Cl)ccc2O)c(Cl)c1]

TABLE 5-continued

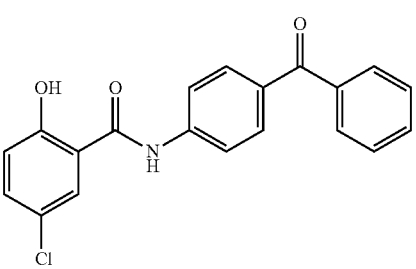 [SMILES: O=C(c1ccccc1)c1ccc(NC(=O)c2cc(Cl)ccc2O)cc1]

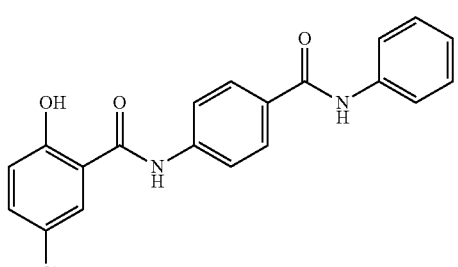

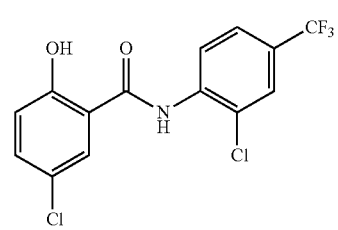 [SMILES: O=C(Nc1ccc(C(F)(F)F)cc1Cl)c1cc(Cl)ccc1O]

TABLE 5-continued
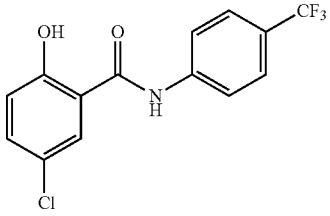 [SMILES: O=C(Nc1ccc(C(F)(F)F)cc1)c1cc(Cl)ccc1O]
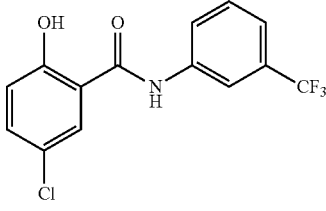 [SMILES: O=C(Nc1cccc(C(F)(F)F)c1)c1cc(Cl)ccc1O]
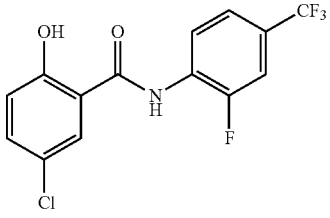 [SMILES: O=C(Nc1ccc(C(F)(F)F)cc1F)c1cc(Cl)ccc1O]
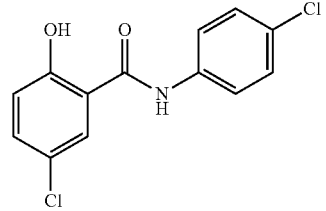 [SMILES: O=C(Nc1ccc(Cl)cc1)c1cc(Cl)ccc1O]
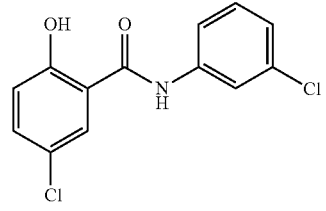 [SMILES: O=C(Nc1cccc(Cl)c1)c1cc(Cl)ccc1O]
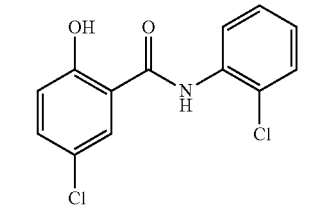 [SMILES: O=C(Nc1ccccc1Cl)c1cc(Cl)ccc1O]
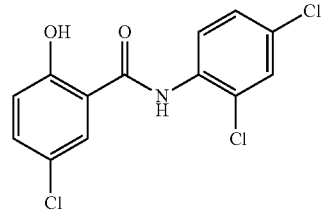 [SMILES: O=C(Nc1ccc(Cl)cc1Cl)c1cc(Cl)ccc1O]
TABLE 5-continued
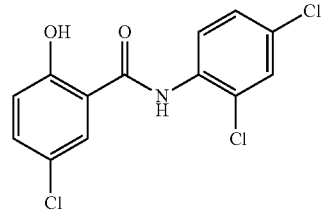 [SMILES: O=C(Nc1ccc(Cl)cc1Cl)c1cc(Cl)ccc1O]
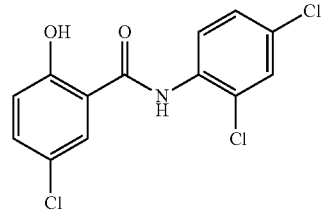 [SMILES: O=C(Nc1ccc(Cl)cc1Cl)c1cc(Cl)ccc1O]
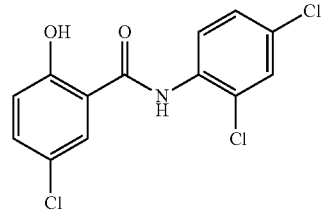 [SMILES: O=C(Nc1ccc(Cl)cc1Cl)c1cc(Cl)ccc1O]
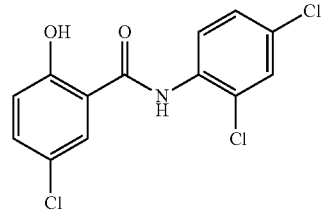 [SMILES: O=C(Nc1ccc(Cl)cc1Cl)c1cc(Cl)ccc1O]
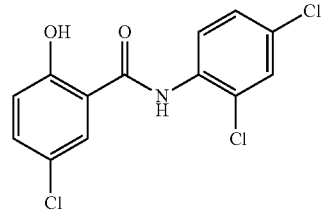 [SMILES: O=C(Nc1ccc(Cl)cc1Cl)c1cc(Cl)ccc1O]
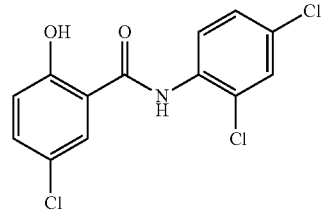 [SMILES: O=C(Nc1ccc(Cl)cc1Cl)c1cc(Cl)ccc1O]
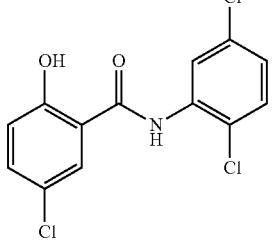

TABLE 5-continued
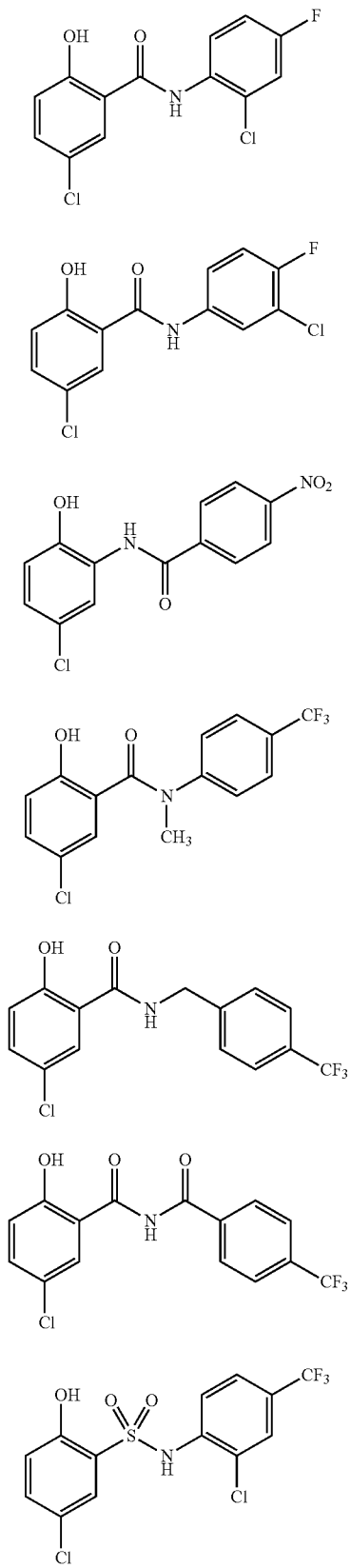
TABLE 5-continued
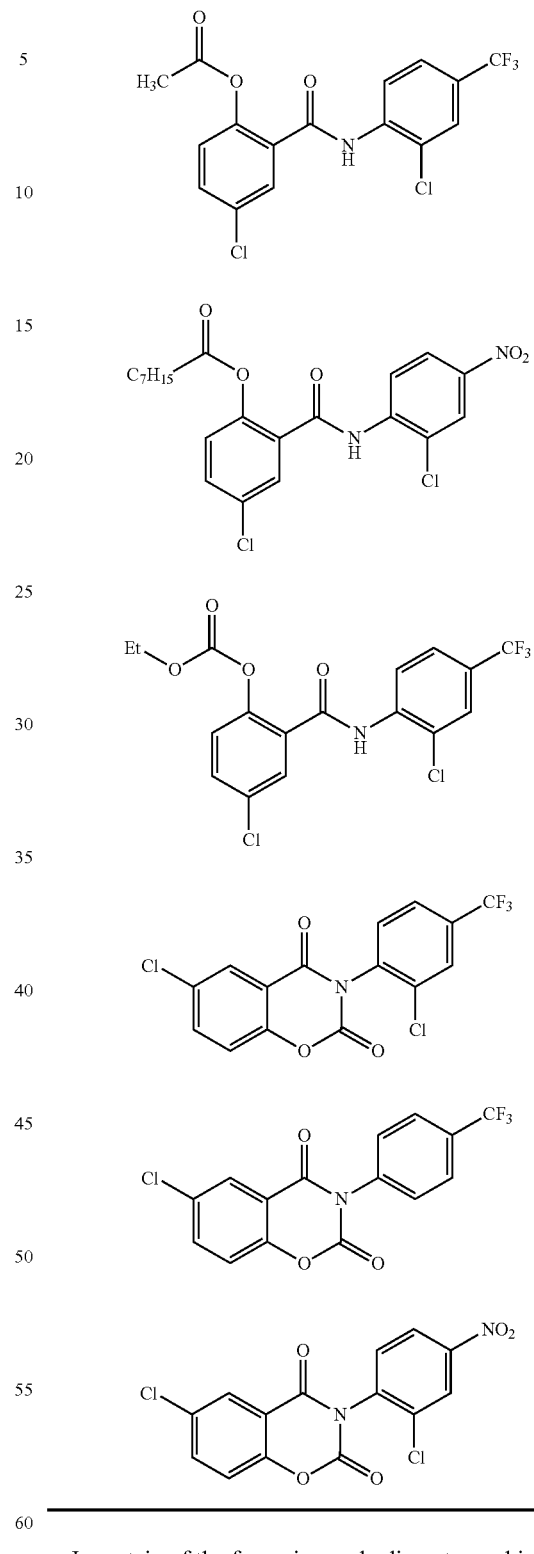
In certain of the foregoing embodiments, acyl is a chemical moiety with the formula R—C(O)—, where R is selected from $C_{1-10}$ alkyl, $C_{2-6}$ heterocyclyl (e.g., heteroaromatic), and $C_{6-12}$ aryl.
Further examples of niclosamide analogues include, but are not limited to those delineated in Table 6.

TABLE 6

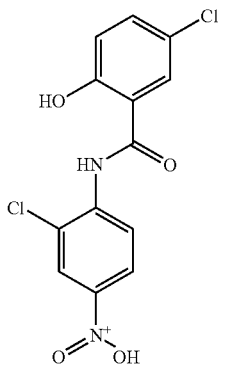

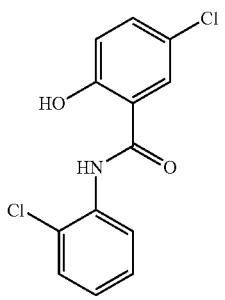 [SMILES: O=C(Nc1ccccc1Cl)c1cc(Cl)ccc1O]

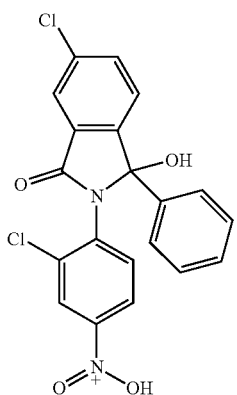

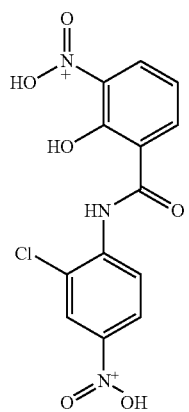

TABLE 6-continued

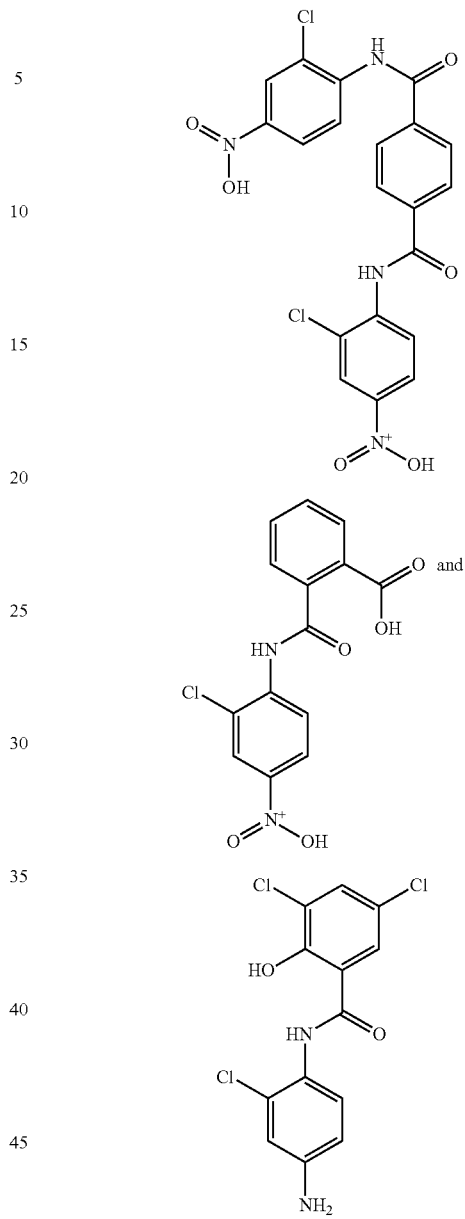

In certain embodiments, the chemical entity is niclosamide or a pharmaceutically acceptable salt or hydrate thereof. "Niclosamide" refers to a compound having the following chemical structure:

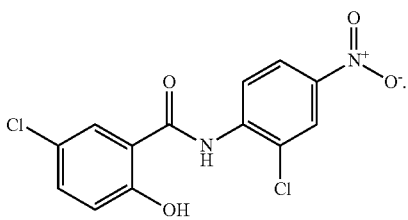

Niclosamide is known by the IUPAC designation: 2'5-dichloro-4'-nitrosalicylanilide and by the CAS designation: CAS: 5-chloro-N-(2-chloro-4-nitrophenyl)-2-hydroxybenzamide. Niclosamide has a relatively low water solubility at about from 5-8 mg/L at 20° C., is sparingly soluble in ether, ethanol and chloroform, and is soluble in acetone. The ethanol amine salt dissolves in distilled water 180-280 mg/L at 20° C.

Niclosamide is available in a various salt or solvated forms. These include, but are not limited to, the ethanolamine salt known by the IUPAC designation 5-chlorosalicyl-(2-chloro-4-nitro) anilide 2-aminoethanol salt or the CAS designation 5-chloro-N-(2-chloro-4-nitrophenyl)-2-hydroxybenzamide with 2-aminoethanol (1.1)—see, e.g., US 2013/0231312; the piperazine salt known by die IUPAC designation 5-chloro-salicyl-(2-chloro-4-nitro) anilide piperazine salt or the CAS designation 5-chloro-N-(2-chloro-4-nitrophenyl)-2-hydroxybenzamide with piperazine (2:1); and niclosamide monohydrate known by the IUPAC designation 5-chloro-salicyl-(2-chloro-4-nitro) anilide monohydrate or the CAS designation 5-chloro-N-(2-chloro-4-nitrophenyl)-2-hydroxybenzamide with monohydrate (1:1).

Niclosamide is commercially available in a variety of formulations including, but not limited to BAYER 73®, BAYER 2353®, BAYER 25 648®, BAYLUSCID®, BAYLUSCIDE®, CESTOCID®, CLONITRALID, DICHLOSALE®, FENASAL®, HL 2447®, IOMESAN®, IOVMEZAN®, LINTEX®, MANOSIL®, NASEMO®, NICLOSAMID®, PHENASAL®, TREDEMINE®, SIJLQUI®, VERMITID®, VERMITIN®, YOMESAN®, and the like.

Compounds disclosed herein are commercially available or can be readily prepared from commercially available starting materials according to established methodology in the art of organic synthesis. General methods of synthesizing the compound can be found in, e.g., Stuart Warren and Paul Wyatt, Workbook for Organic Synthesis: The Disconnection Approach, second Edition, Wiley, 2010. See also, e.g., U.S. Pat. No. 8,148,328, which is incorporated herein by reference in its entirety and Mook, et al., *Bioorg. Med. Chem* 2015, 23, 5829, which is incorporated herein by reference in its entirety.

In other embodiments, the chemical entity can be selected from the compounds that are disclosed genetically, sub genetically and specifically in any one or more of WO 2004/006906; WO 2006/120178; US 2009/0062396; WO 2012/143377; WO 2012/068274; U.S. Pat. Nos. 7,132,546; 7,989,498; and 8,263,857; each of which is incorporated herein by reference in its entirety.

Other Chemical Entities

In some embodiments, the chemical entity can be an anthelminthic agent selected from nitazoxanide, closantel, pyrvinium pamoate, and salinomycin. See. e.g., Senkowski, W., et al., *Mol. Cancer Ther.* 2015, 14, 1504.

Cocrystals of Chemical Entities

Overview

In some embodiments, the chemical entity can be in the form of a cocrystal that includes (i) the chemical entity (e.g., a mitochondrial uncoupling agent (e.g., niclosamide or a niclosamide analogue) or a pharmaceutically acceptable salt and/or hydrate thereof; and (ii) one or more pharmaceutically acceptable coformers. The term "co-crystal" as used herein refers to a crystalline material comprised of two or more unique solids at room temperature in a stoichiometric or non-stoichiometric ratio, which are held together in the crystal lattice by one or more non-covalent interactions (e.g., hydrogen bonds, pi-stacking, guest-host complexation and van der Waals interactions).

In some embodiments, at least one of the one or more non-covalent interactions is a hydrogen bond. In certain of these embodiments, the chemical entity is the hydrogen bond donor, and one of one or more coformers is the hydrogen bond acceptor. In other embodiments, the chemical entity is the hydrogen bond acceptor, and one of one or more coformers is the hydrogen bond donor.

The co-crystals described herein can include one or more solvate (e.g., water or an organic solvent containing one or more hydroxyl groups, e.g., a $C_1$-$C_6$ alcohol or diol, e.g., a $C_1$-$C_6$ alcohol or diol, e.g., ethanol or propylene glycol) molecules in the crystalline lattice. However, solvates of chemical entities that do not further comprise a coformer (e.g., a solid conformer) are not encompassed by the co-crystal definition set forth in this disclosure.

In some embodiments, the cocrystal includes more than one coformer. For example, two, three, four, five, or more coformers can be incorporated in a co-crystal with the chemical entity. The ratio of the chemical entity to each of the one or more pharmaceutically acceptable coformers may be stoichiometric or non-stoichiometric. As a non-limiting example, 1:1, 1:1.5 and 1:2 ratios of chemical entity:coformer are contemplated.

The chemical entity and each of the one or more pharmaceutically acceptable coformers may each be independently specified as a free form, or more specifically, a free acid, free base, or zwitter ion; a salt, or more specifically for example, an inorganic base addition salt such as sodium, potassium, lithium, calcium, magnesium, ammonium, aluminum salts or organic base addition salts, or an inorganic acid addition salts such as HBr, HCl, sulfuric, nitric, or phosphoric acid addition salts or an organic acid addition salt such as acetic, proprionic, pyruvic, malanic, succinic, malic, maleic, fumaric, tartaric, citric, benzoic, methanesulfonic, ethanesulforic, stearic or lactic acid addition salt; an anhydrate or hydrate of a free form or salt, or more specifically, for example, a hemihydrate, monohydrate, dihydrate, trihydrate, quadrahydrate, pentahydrate; or a solvate of a free form or salt.

The Chemical Entity

In some embodiments, the chemical entity (e.g., a mitochondrial uncoupling agent (i.e., component (i) above) can form one or more hydrogen bonds with the one or more pharmaceutically acceptable coformers in the cocrystal. In some embodiments, the chemical entity can accept one or more hydrogen bonds from the one or more pharmaceutically acceptable coformers in the cocrystal. In some embodiments, the chemical entity can form one or more hydrogen bonds with the one or more pharmaceutically acceptable coformers, and the chemical entity can accept one or more hydrogen bonds with the one or more pharmaceutically acceptable coformers in the cocrystal.

In some embodiments, the chemical entity (e.g., a mitochondrial uncoupling agent (i.e., component (i) above) includes one or more functional groups selected from the group consisting of: ether, thioether, hydroxy, sulfhydryl, aldehyde, ketone, thioketone, nitrate ester, phosphate ester, thiophosphate ester, ester, thioester, sulfate ester, carboxylic acid, phosphonic acid, phosphinic acid, sulfonic acid, amido, primary amine, secondary amine, ammonia, tertiary amino, sp2 amino, thiocyanate, cyanamide, oxime, nitrile, diazo, haloalkyl, nitro, heterocyclic ring, heteroaryl ring, epoxide, peroxide, and hydroxamic acid.

In some embodiments, the chemical entity (e.g., a mitochondrial uncoupling agent (i.e., component (i) above) is niclosamide or a pharmaceutically acceptable salt or hydrate thereof; or a niclosamide analog, or a pharmaceutically acceptable salt or hydrate thereof. In some of these embodiments, the chemical entity can be a compound having any one of formulas (I) and (XVIII)-(XXV), e.g., formula XXIV, XXV, or XXVII; or any one of the list of coformers delineated below. In certain of these embodiments, the chemical entity can be a niclosamide analogue having any one of formulas (I) and (XVIII)-(XXV), e.g., formula XXIV or XXV; or XXVI; or any one of the list of coformers delineated below. In certain of these embodiments, the chemical entity can be a niclosamide or a pharmaceutically acceptable salt or hydrate thereof (e.g., niclosamide).

Coformers

In some embodiments, at least one of the one or more pharmaceutically acceptable coformers can form one or more hydrogen bonds with the chemical entity in the cocrystal.

In some embodiments, at least one of the one or more pharmaceutically acceptable coformers can accept one or more hydrogen bonds from the chemical entity in the cocrystal. In some embodiments, at least one of the one or more pharmaceutically acceptable coformers can form one or more hydrogen bonds with the chemical entity in the cocrystal, and at least one of the one or more pharmaceutically acceptable coformers can accept one or more hydrogen bonds from the chemical entity in the cocrystal.

In some embodiments, at least one of the one or more pharmaceutically acceptable coformers comprises one or more functional groups selected from the group consisting of: ether, thioether, hydroxy, sulfhydryl, aldehyde, ketone, thioketone, nitrate ester, phosphate ester, thiophosphate ester, ester, thioester, sulfate ester, carboxylic acid, phosphonic acid, phosphinic acid, sulfonic acid, amido, primary amine, secondary amine, ammonia, tertiary amino, sp2 amino, thiocyanate, cyanamide, oxime, nitrile, diazo, haloalkyl, nitro, heterocyclic ring, heteroaryl ring, epoxide, peroxide, and hydroxamic acid.

In certain embodiments, each of the one of the one or more pharmaceutically acceptable coformers is independently selected from acetamide, benzamide, (+/−)-limonene, 1-(phenylazo)-2-naphthylamine, 1,2,6-hexanetriol, 1,2-dimyristoyl-sn-glycero-3-(phospho-s-(1-glycerol)), 1,2-dimyristoyl-sn-glycero-3-phosphocholine, 1,2-dioleoyl-sn-glycero-3-phosphocholine, 1,2-dipalmitoyl-sn-glycero-3-(phospho-rac-(1-glycerol)), 1,2-distearoyl-sn-glycero-3-(phospho-rac-(1-glycerol)), 1,2-distearoyl-sn-glycero-3-phosphocholine, 1,5-naphthalene-disulfonic acid, 1-hydroxy-2-naphthoic acid, 1-o-tolylbiguanide, 2-ethyl-1,6-hexanediol, 4-aminobenzoic acid, 4-aminopyridine, 4-aminosalicylic acid, 4-chlorobenzene-sulfonic acid, 4-ethoxyphenyl urea, 7-oxo-dhea, acacia, acacia mucilage, acacia syrup, acesulfame, acesulfame potassium, acetohydroxamic acid, acetone sodium bisulfite, acetylated lanolin alcohols, acetylated monoglycerides, acetylcysteine, acetyltributyl citrate, acrylates copolymer, acrylic acid-isooctyl acrylate copolymer, adenine, adipic acid, alanine, albumin aggregated, albumin colloidal, albumin human, albumins, alginic acid, alkyl ammonium sulfonic acid betaine, alkyl aryl sodium sulfonate, allantoin, allopurineol, allyl alpha-ionone, alpha-terpineol, alpha-tocopherol, alpha-tocopherol acetate, aminobenzoate sodium, amyl acetate, anethole, anhydrous citric acid, anhydrous dextrose, anhydrous lactose, anhydrous tribasic sodium phosphate, anhydrous trisodium citrate, arginine, arlacel, asafetida, ascorbic acid, ascorbyl palmitate, asparagine, aspartame, aspartic acid, bacteriostatic sodium chloride injection, barium sulfate, benzalkonium chloride, benzenesulfonic acid, benzethonium chloride, benzododecinium bromide, benzoic acid, benzyl acetate, benzyl alcohol, benzyl benzoate, benzyl chloride, beta-carotene, betanaphthol, betose, bibapcitide, bismuth subcarbonate, bismuth subgallate, boric acid, brocrinat, butyl stearate, butylated hydroxyanisole, butylated hydroxytoluene, butylparaben, butyric acid, C-11-1-aminocyclohexanecarboxylic acid, C12-15 alkyl lactate, caffeine, calcobutrol, cal diamide sodium, caloxetate trisodium, calteridol calcium, camphoric acid, capric acid, captan, captisol, carboxypolymethylene, carmine, carnauba wax, carnauba yellow wax, carrageenan, carrageenan calcium, carrageenan salt, carrageenan sodium, ceresin, ceteareth-12, ceteareth-15, ceteareth-30, cetearyl alcohol/ceteareth-20, cetearyl ethylhexanoate, ceteth-10, ceteth-2, ceteth-20, ceteth-23, cetostearyl alcohol, cetrimonium chloride, cetyl alcohol, cetyl esters wax, cetyl palmitate, cetylpyridinium chloride, chlorocresol, chloroxylenol, cholesterol, chrysin, cinnamaldehyde, cinnamic acid, citrate, citric acid, citric acid monohydrate, clemizole, cocamide ether sulfate, cocamine oxide, coco betaine, coco diethanolamide, coco monoethanolamide, coco-caprylate, coco-glycerides, creatine, creatinine, cresol, cupric sulfate, cyclamic acid, cyclomethicone, cyclomethicone 5, cysteine, dalfampridine, decyl methyl sulfoxide, dehydroacetic acid, denatonium benzoate, deoxycholic acid, dextran, dextran 40, dextrates, dextrin, dextrose, dextrose monohydrate, diacetylated monoglycerides, diatrizoic acid, dibasic anhydrous sodium phosphate, dibasic sodium phosphate, dibasic sodium phosphate dihydrate, dibasic sodium phosphate dodecahydrate, dibasic sodium phosphate heptahydrate, dibutyl phthalate, dibutyl sebacate, diethyl phthalate, diethyl pyrocarbonate, diethyl sebacate, diethylaminoethyl stearamide phosphate, diethylene glycol monoethyl ether, diethylene glycol monomethyl ether, diethylhexyl phthalate, diisopropyl adipate, diisopropyl dilinoleate, diisopropylbenzothiazyl-2-sulfenamide, dimethicone medical fluid 360, dimethyl isosorbide, dimethyl phthalate, dimethyl sulfoxide, dimethyldioctadecylammonium bentonite, dimethylglycine, dimethylsiloxane/methylvinylsiloxane copolymer, dinoseb-ammonium, dipropylene glycol, di sodium cocoamphodiacetate, di sodium hydrogen citrate, di sodium laureth sulfosuccinate, di sodium lauryl sulfosuccinate, di sodium oleamido monoethanolamine sulfosuccinate, disodium sulfosalicylate, disofenin, dl-a350 lactic acid, dl-acetyltryptophan, dl-alpha-tocopherol, dl-alpha-tocopherol acetate, dl-dipalmitoylphosphatidylglycerol, dl-distearoylphosphatidylcholine, dl-glutamic acid, dl-tartaric acid, d-mannose, dmdm hydantoin, docosanol, docusate sodium, d-ribose, edetate calcium disodium, edetate disodium, edetate sodium, edetic acid, egg phosphatidyl glycerol, egg phospholipids, entsufon, entsufon sodium, epilactose, epitetracycline hydrochloride, erythorbic acid, erythritol, ethanolamine hydrochloride, ethyl maltol, ethyl oleate, ethyl vanillate, ethyl vanillin, ethylenediamine dihydrochloride, ethylhexyl hydroxystearate, ethylparaben, eucalyptol, eugenol, exametazime, fatty acid esters, fatty acid glycerides, fatty acid pentaerythriol ester, fatty acids, fatty alcohol citrate, fatty alcohols, ferric chloride, ferric oxide, ferrosoferric oxide, ferrous fumarate, ferrous oxide, fluorescein, fructose, fumaric acid, fumaryl diketopiperazine, gadolinium oxide, galactaric acid, galactose, gamma cyclodextrin, genistein, gentisic acid, gentisic acid ethanolamide, gentisic acid ethanolamine, gluceptate sodium, gluconic acid, gluconolactone, glucosamine, glucose, glucuronic acid, glutamic acid, glutamic acid hydrochloride, glutamine, glutaric acid, glutathione, glyceryl caprylate, glyceryl dibehenate, glyceryl distearate, glyceryl isostearate, glyceryl laurate, glyceryl monostearate, glyceryl oleate, glyceryl palmitate, glyceryl palmitostearate, glyceryl ricinoleate, glyceryl stearate, glyceryl stearate-laureth-23, glyceryl stearate/peg stearate, glyceryl stearate/peg-100 stearate, glyceryl stearate/peg-40 stearate, glyceryl stearate-stearamidoethyl diethylamine, glyceryl trioleate, glycine, glycine hydrochloride, glycol distearate, glycol stearate, glycolic acid, glycyrrhizin, guanidine hydrochloride, hexylresorcinol, hippuric acid, histidine, hyaluronate sodium, hydrocortisone, hydroquinone, hydrous-citric acid, hydroxyethylpiperazine ethane sulfonic acid, hydroxyoctacosanyl hydroxystearate, hydroxyprogesterone caproate, hydroxypropyl beta-cyclodextrin, hystrene, illicium anisatum, imidazole, imidurea, indigotindisulfonate sodium, iodoxamic acid, iofetamine hydrochloride, ipriflavone, isoleucine, isopropyl isostearate, isopropyl myristate, isopropyl myristate-myristyl alcohol, isopropyl palmitate, isopropyl stearate, isostearic acid, isostearyl alcohol, lactate, lactitol monohydrate, lactobionic acid, lactose, landalgine, lanolin, lauralkonium chloride, lauramine oxide, laureth sulfate, lauric acid, lauric diethanolamide, lauric myristic diethanolamide, lauroyl sarcosine, lauryl lactate, lauryl sulfate, lecithin, leucine, levomenthol, levulinic acid, lidofenin, 1-sodium lactate, lysine, maleic acid, malic acid, malonic acid, maltitol, maltodextrin, maltol, maltose anhydrous, mandelic acid, mannitol, maprofix, mebrofenin, medium-chain triglycerides, medronate disodium, medronic acid, menthol, meta-cresol, methionine, methyl salicylate, methyl stearate, methylchloroisothiazolinone, methylisothiazolinone, methylparaben, methylparaben sodium, miripirium chloride, mono and diglyceride, monobasic sodium phosphate, monobasic sodium phosphate anhydrous, monobasic sodium phosphate dihydrate, monobasic sodium phosphate monohydrate, monoglyceride citrate, monoglycerides, monosodium citrate, monosodium glutamate, monostearyl citrate, monothioglycerol, myristic acid, myristyl alcohol, myristyl lactate, niacinamide, nicotinamide, nicotinic acid, W-methyl glucamine, octanoic acid, oleth-20, oleyl alcohol, oleyl oleate, orotic acid, oxalic acid, oxidronate disodium, oxyquinoline, palmitamine oxide, palmitic acid, pamoic acid, pentadecalactone, pentaerythritol cocoate, pentasodium pentetate, pentetate calcium trisodium, pentetic acid, phenol, phenonip, phenoxyethanol, phenylalanine, phenylethyl alcohol, phospholipid, piperazine, piperazine hexahydrate, procaine, product wat, proline, propenyl guaethol, propyl gallate, propylene carbonate, propylene glycol, propylene glycol-lecithin, propylene glycol alginate, propylene glycol diacetate, propylene glycol dicaprylate, propylene glycol monolaurate, propylene glycol monopalmitostearate, propylene glycol palmitostearate, propylene glycol ricinoleate, propylene glycol/diazolidinyl urea/methylparaben/propylparben, propylparaben, propylparaben sodium, p-toluenesulfonic acid, pyridoxamine, pyridoxine (4-pyridoxic acid), quercetin, resveratrol, riboflavin, saccharin, saccharin calcium, saccharin sodium, saccharin sodium anhydrous, salicylic acid, saturated fatty acid esters, sebacic acid, serine, sodium 1,2-ethanedisulfonate, sodium 2-naphthalenesulfonate, sodium acetate, sodium acetate anhydrous, sodium alginate, sodium alkyl sulfate, sodium aluminium silicate, sodium ascorbate, sodium benzoate, sodium bicarbonate, sodium bisulfate, sodium bisulfate acetone, sodium bisulfite, sodium bitartrate, sodium borate, sodium borate decahydrate, sodium carbonate, sodium carbonate decahydrate, sodium carbonate monohydrate, sodium carboxymethyl beta-glucan (ds 065-085), sodium caseinate, sodium cellulose, sodium cetostearyl sulfate, sodium chlorate, sodium chloride, sodium chloride injection, sodium cholesteryl sulfate, sodium citrate, sodium citrate hydrous, sodium cocoyl sarcosinate, sodium cyclamate, sodium desoxycholate, sodium dithionite, sodium dodecylbenzenesulfonate, sodium ethylparaben, sodium formaldehyde sulfoxylate, sodium gluconate, sodium hydroxide, sodium hypochlorite, sodium iodide, sodium lactate, sodium laureth-2 sulfate, sodium laureth-3 sulfate, sodium laureth-5 sulfate, sodium lauroyl sarcosinate, sodium lauryl sulfate, sodium lauryl sulfoacetate, sodium metabisulfite, sodium nitrate, sodium oleate, sodium phosphate, sodium phosphate dihydrate, sodium phosphite, sodium polyacrylate, sodium polyacrylate (2500000 MW), sodium polymetaphosphate, sodium propionate, sodium pyrophosphate, sodium pyrrolidone carboxylate, sodium starch glycolate, sodium starch glycolate type a corn, sodium starch glycolate type a potato, type B potato sodium starch glycolate, sodium stearate, sodium stearyl fumarate, sodium succinate hexahydrate, sodium sulfate, sodium sulfate anhydrous, sodium sulfate decahydrate, sodium sulfite, sodium sulfosuccinated undecyclenic monoalkylolamide, sodium tartrate, sodium thioglycolate, sodium thiomalate, sodium thiosulfate, sodium thiosulfate anhydrous, sodium trimetaphosphate, sodium tripolyphosphate, sodium xylenesulfonate, sorbic acid, sorbitan, sorbitan isostearate, sorbitan monolaurate, sorbitan monooleate, sorbitan monopalmitate, sorbitan monostearate, sorbitan sesquioleate, sorbitan trioleate, sorbitan tristearate, sorbitol, squalane, stannous 2-ethylhexanoate, stearalkonium chloride, stearalkonium hectorite/propylene carbonate, stearamidoethyl diethylamine, stearates, stearic acid, stearic diethanolamide, stearoxytrimethylsilane, stearyl alcohol, succinic acid, sucralose, sucrose, sucrose distearate, sucrose laurate, sucrose palmitate, sucrose polyesters, sucrose stearate, sucrose symp, sulfacetamide sodium, sulfobutylether beta-cyclodextrin, tagatose, tartaric acid, tegacid, terf-buty 1 hydroquinone, tetrofosmin, theophylline, thimerosal, threonine, thymol, tocopherol, tocophersolan, tragacanth, triacetin, tribasic sodium phosphate, tribasic sodium phosphate monohydrate, tribehenin, tricaprylin, triceteareth-4 phosphate, triethanolamine lauryl sulfate, tri ethyl citrate, trihydroxystearin, trilaneth-4 phosphate, trilaureth-4 phosphate, trimyristin, tris, tri sodium citrate dihydrate, tri sodium hedta, tristearin, trolamine, tromantadine, tromethamine, tryptophan, tyloxapol, tyrosine, undecylenic acid, urea, urethane, ursodiol, valine, vanillin, versetamide, viscarin, vitamin E, vitamin E acetate, vitamin K5, xylitol, and zinc sulfate. See also U.S. Pat. No. 7,927,613, which is incorporated herein by reference in its entirety. Other pharmaceutically acceptable coformers include those delineated in the "Generally Regarded as Safe" ("GRAS") and/or the US FDA "Everything Added to Food in the United States" ("EAFUS") lists.

In certain embodiments, at least one of the one or more pharmaceutically acceptable coformers is selected from the group consisting of caffeine, urea, p-aminobenzoic acid, theophylline, benzyl benzoate, and nicotinamide. In other embodiments, the one or more pharmaceutically acceptable coformers is other than those selected from the group consisting of caffeine, urea, p-aminobenzoic acid, theophylline, benzyl benzoate, and nicotinamide. In other embodiments, the one or more pharmaceutically acceptable coformers is other than those selected from the group consisting of acetamide, benzamide, 2-aminothiazole, and isoniazide. In still other embodiments, the one or more pharmaceutically acceptable coformers is an amino acid (e.g., proline, e.g., D-proline or L-proline, or racemic proline). In another embodiment, the one or more pharmaceutically acceptable coformers is a 5-10 (e.g., 5-9, 5-6, or 5) membered heteroaryl, e.g., a nitrogen-containing heteroaryl, e.g., imidazole.

In certain embodiments, at least one of the one or more pharmaceutically acceptable coformers is a second API. In certain of these embodiments, the second API is independently selected from (−)-amlodipine, (−)-halofenate, (R)-salbutamol, (R)-salbutamol, (R,R)-formoterol, (S)-doxazosin, (S)-fluoxetine, (S)-oxybutynin, 1,2-naphthoquinone, 17-methyltestosterone, 17α-hydroxyprogesterone, 195mPt-cisplatin, 1-naphthyl salicylate, l-naphthylamine-4-, 1-theobromineacetic, 1α-hydroxycholecalciferol, 2,4,6-tribromo-m-cresol, 2,6-diamino-2'-butyloxy-3,5'-azopyridine, 2-[[[(1 r)-2-(1 h-imidazol-4-yl)-1-methylethyl]imino]phenylmethyl]-phenol, 21-acetoxypregnenolone, 2-amino-4-picoline, 2-aminothiazole, 2-ethoxybenzoic acid, 2-naphthol, 2-naphthyl benzoate, 2-naphthyl lactate, 2-naphthyl salicylate, 2-p-sulfanilylanilinoethanol, 2-thiouracil, 3',3'',5',5''-tetra-bromophenolphthalein, 3-amino-4-hydroxybutyric acid, 3-Bromo-D-camphor, 3-Hydroxycamphor, 3-O-Lauroylpyridoxol Diacetate, 3-pentadecyl catechol, 3-quinuclidinol, 4,4'-oxydi-2-butanol, 4,4'-sulfinyl dianiline, 4-amino-3-hydroxybutyric acid, 4-amino-3-phenylbutyric acid, 4-aminosalicylic acid, 4-chloro-m-cresol, 4-hexylresorcinol, 4-salicyloylmorphdine, 5'-nitro-2'-propoxyacetanilide, 5-aminolevulinic acid, 5-azacitidine, 5-bromosalicyl-hydroxamic acid, 5F-DF-203, 5-FU, 5-HT3 antagonists, 6-azauridine, 6-mercaptopurine, 8-hydroxyquinoline, 9-aminocamptothecin, A-151892, A-5021, abacavir, abaperidone, abarelix, abciximab, abecamil, abetimus, abiraterone, ABLC, ABT-751, AC-5216, acadesine, acamprosate, acamprosate, acarbose, acebrophylline, acebutolol, acecainide, acecarbromal, aceclofenac, acedapsone, acediasulfone, acefylline, aceglutamide, aceglutamide, acemetacin, acenocoumarol, aceponate, acetal, acetamidoeugenol, acetaminophen, acetaminosalol, acetanilide, acetarsone, acetazolamide, acetiamine, acetohexamide, acetohydroxamic acid, acetophenazine, acetophenide, acetophenone, acetosulfone, acetoxolone, acetrizoat, acetyl, acetylcamitine, acetylcholine, acetylcholine, acetylcysteine, acetylleucine, acetylpheneturide, acetylsalicylate, acetylsalicylic acid, aciclovir, acifran, acipimox, acitazanolast, acitretin, aclarubicin, aclatonium, aconitine, Acranil®, acriflavine, acrisorcin, acrivastine, acrivastine, actagardine derivative, actarit, ACTH, acyclovir, adapalene, ADCON-L, adefovir, adefovir dipivoxil, adenoscan, adenosine triphosphate, ADEPT, adinazolam, adiphenine, ADL-10-0101, adrafinil, adrenal one, adrenochrome, adrogolide, AEOL-10150, aesthinol, AET, AF-2259, afloqualone, AG-041R, AG-2037, AGN-194310, agomelatine, ahistan, AHL-157, AIT-034, AIT-202, AJ-9677, AJG-049, ajmaline, akzo desogestrel, alacepril, alapivoxil, albaconazole, albendazole, albuterol, albutoin, alclofenac, alclometasone, alcuronium, aldioxa, aldol, aldosterone, alendronate, alendronic acid, alexidine, alfacalcidol, alfadolone, alfaxalone, alfentanil, alfimeprase, alfuzosin, alfuzosin, algestone, algestone, algin, alglucerase, alibendol, aliskiren, alitertinoin, alizapride, alkannin, alkofanone, allantoin, allobarbital, allopurinol, allyl isothiocyanate, allylestrenol, almagate, alminoprofen, almitrine, almotriptan, aloe-emodin, aloin, alosetron, alovudine, aloxiprin, alpha-, alpha-1 protease, alphaprodine, alpidem, alpiropride, alprazolam, alprenolol, alsactide, ALT-711, Althiazid, altinicline, altretamine, aluminium chloride hexahydrate, aluminon, aluminum acetate solution, aluminum chlorate, aluminum hydroxychloride, aluminum potassium sulfate, aluminum sodium sulfate, alusulf, alverine, alvimopan, alvocidib, ALX-0646, AM-24, AM-36, AM-477, amantadine, amantanium, ambazon, ambenonium, ambrisentan, ambroxol, ambucaine, ambuphylline, ambusid, ambutonium bromide, amcinonide, AMD-3100, amdinocillin, amdinocillin pivoxil, amdoxovir, amelubant, ameri caine, amezinium, amfenac, amidephrine, amidinomycin, amifostine, amiglumide, amikacin, amiloride, aminacrine, amineptine, aminitrozole, amino acid preparations, aminocaproic acid, aminoglutethimide, aminoguanidine, aminohippurate, aminometradine, aminopentamide, aminophylline, aminopromazine, aminopyrine, aminoquinuride, aminorex, amiodarone, amiodipine, amiphenazole, amiprilose, amisulpride, amitriptyline, amitriptyline+ketamine, amitriptylinoxide, amlexanox, ammoniacum, ammoniated mercuric chloride, ammonium benzoate, ammonium mandelate, ammonium salicylate, ammonium valerate, amobarbital, amocarzine, amodiaquin, amorolfine, amoscanat, amosulalol, amotriphene, amoxapine, amoxicillin, amoxicillin+potassium clavulan, AMP Alex, amphetamine, amphetaminil, amphotericin B, ampicillin, ampiroxicam, ampligen, amprenavir, amrinose, amrubicin, amsacrine, amtolmetin guacil, amylocaine, AN-152, anabolic steroids, anagestone, anagrelide, anastrozole, anazolene, ancitabine, ancrod, andolast, androisoxazole, androstenediol, anecortave, anethole, anethole trithione, angiogenix, angiotensin, anhydrovinblastine, anidulafungin, anilerdine, aniracetam, anisindione, anisomycin, anisotropine, anistreplase, antazoline, anthiolimine, anthralin, anthramycin, anthrarobin, anthrax inhibitor, anti angiogenic, anticort, antidepressants, anti-invasins, antimony potassium tartrate, antimony sodium thioglycollate, antimony thioglycollamide, anti progestin, antipyrine, antipyrine salicylate, antithrombin HI, anxiolytics, AP-521, AP-5280, apalcillin, apaziquone, apazone, apocodeine, apomine, apomorphine, apraclonidine, aprepitant, aprindine, aprobarbital, apronalide, aprotinin, aptiganel, AQ4N, aquavan, AR-116081, AR-A2, arachidonic acid, aranidipine, arbekacin, arbidol, arbutamine, arcitumomab, ardeparin, arecoline, argatroban, arginine, Ariflo®, aripiprazole, arofylline, arotinolol, arsacetin, arsenic trioxide, arsphenamine, arteether, arteflene, artemether, artemisinin, artemotil, artesunate, arzoxifene, AS-3201, ASA, ascaridole, ascorbic acid, asenapine, asimadoline, asocarboxazid, asoprisnil, asoxime, aspartic acid, aspidin, aspidinol, aspirin, aspirin dipyridamole, aspoxicillin, AST-120, astemizole, asulacrine, AT-1015, atamestane, atazanavir, atenolol, atenolol+chlorthalidone, atenolol+nifedipine, atevirdine, atipamezole, atiprimod dimaleate, ATL-146e, atomoxetine, atorvastatin, atosiban, atovaquone, atovaquone+proguanil, atracurium, atrasentan, atrial natriuretic, atrolactamide, atropine, augmentin, auranofin, aurothioglucose, avasimibe, avobenzone, AWD-12-281, azacitidine, azacyclonol, azanidazole, azapropazone, azaserine, azasertron, azatadine, azathiprine, AZD-4282, AZD-6140, azelaic acid, azelastine, azelnidipine, azidamfenicol, azidocillin, azimilide, azintamide, azithromycin, azlocillin, azosemide, aztreonam, azulene, bacampicillin, bacitracin, baclofen, baicalein, balofloxacin, balsalazide, bambuterol, bamethan, bamifylline, bamipine, barbital, bamidipine, BAS-118, basic alumina, baslilximab, batimastat, batroxobin, Bay-41-2272, Bay-41-8543, BAY-43-9006, BAY-57-1293, bazedoxifen, BBR-3464, BBR-3576, BBR-3610, BCH-1868, bebeerine, beclamide, beclometasone, befloxatone, befunolol, bemegride, benactyzine, benazepril, bencyclane, bendazac, bendroflumethiazide, benetonide, benexate, benfluorex, benfotiamine, benfurodil, benidipine, benorylate, benoxaprofen, benoxinate, benperidol, benproperine, benserazide, bentazepam, bentiromide, bentoquatam, benzafibrate, benzalkonium, benzarone, benzathine, benzbromarone, benzethonium, benzetimide, benzilonium, benziodarone, benznidazole, benzocaine, benzoctamine, benzonatate, benzoxonium chloride, benzoyl peroxide, benzoylpas, benzphetamine, benzpiperylon, benzquinamide, benzthiazide, benztropine, benzydamine, benzyl benzoate, benzylhydrochloro-thiazide, benzylmorphine, bephenium, bepotastine, bepridil, beraprost, berberine, bergapten, bermoprofen, besipirdine, betahistine, betaine, betamethasone, betamipron, betasine, betaxolol, betazole, bethanechol, bethanidine, betoxycaine, bevantolol, bevonium, bexarotene, bezitramide, BG-9928, BIA-2-024, BIA-2-093, BIA-3-202, bialamicol, biapenem, bibenzonium, bibrocathol, bicalutamide, bicifadine, bicisate, bicyclic, bidisomide, bietamiverine, bietanautine, bietaserpine, bifermelane, bifluranol, bifonazole, bimatoprost, bimoclomol, bimosiamose, binifibrate, binodenoson, biomed-101, biotin, biperiden, biriperone, birlcodar, bisacodyl, bisantrene, bisbentiamine, bisdequalinium, bismuth, bismuth, bismuth, bismuth aluminate, bismuth ethyl, bismuth sodium, bismuth sodium triglycollamate, bismuth subcarbonate, bismuth subgallate, bismuth subnitrate, bismuth subsalicylate, bisoprolol, bisoprolol+HCTZ, bisoprolol+trichloromethiazide, bisoxatin, bithionol, bitolterol, bitoscanat, BL-3875, bleomycin, blonanserin, BMS-184476, BMS-387032, BN-82451, BNP-7787, BO-653, bolandiol, bolasterone, boldenone, bopindolol, bornyl chloride, bornyl salicylate, bortezomib, bosentan, bradycor, brain natriuretic, brallobarbital, brasofensine, brequinar, bretylium, brilliant green, brimonidine, brinzolamide, brivudin, brodimoprim, bromazepam, bromfenac, bromhexine bromide, bromindione, bromisovalum, bromocriptine, bromo-diphenhydramine, bromoform, bromopride, bromo-salicychloranilide, bromperidol, brompheniramine, broparoestrol, bropirimine, brostallicin, brotizolam, brovincamine, broxyquinoline, brozuridine, brucine, bucetin, bucillamine, bucindolol, bucladesine, buclizine, buclosamide, bucolome, bucricaine, bucumolol, budesonide, budesonide+formoterol, budipine, budralazine, bufeniode, bufetolol, bufexamac, buflomedil, buformin, bufuralol, bumadizon, bumetanide, bunaftine, bunamiodyl sodium, bunazosin, bunitrolol, bupivacaine, bupranolol, buprenorphine, bupropion, buramate, buserelin, buspirone, busulfan, busulfan, butabarbital, butacaine, butacetin, butalamine, butalbital, butallylonal, butamben, butamirate, butanilicaine, butaperazine, butaverine, butazolamide, butedronic acid, butenafine, butethal, butethamate, butethamine, buthalital, buthiazide, butibufen, butidrine, butobendine, butoconazole, butoctamide, butofilolol, butorphanol, butoxycaine, butriptyline, butropium, butylthiolaurate, butyrate propio, buzepide, BVT-5182, BXT-51072, C-1311, cabergoline, cabergoline, cacodylic acid, cactinomycin, cadexomer iodine, cadmium salicylate, cadralazine, cafaminol, caffeine, calcifediol, calcipotriene, calcipotriol, calcipotriol+beclometasone, calcitriol, calcium 3-aurothio-2-propanol-1-sulfonate, calcium acetylsalicylate, calcium bromolactobionate, calcium carbonate, calcium gluconate, calcium glycerophosphate, calcium hopantothenate, calcium iodobehenate, calcium iodosterate, calcium lactate, calcium levulinate, calcium mesoxalate, calcium N-carbamoylaspartate, calcium polycarbophil, calcium propionate, calcium succinate, caldaret, calusterone, camazepam, camostat, camphor, camphorate, camphotamide, camptothecin, candesartan, candesartan cilexetil, candoxatril, canertinib, canrenone, cantharidin, cantuzumab mertansine, capecitabine, capobenic acid, capravirine, capromab, capsaicin cream, captodiamine, captopril, captopril+HCTZ, capuride, carabersat, caramiphen, carazolol, caibachol, carbamazepine, carbamide peroxide, carbarsone, carbaryl, carb azochrome, carbendazim, carbenicillin, carbenoxolone, carbetapentane, carbicarb, carbidopa, carbidopa+levodopa-1, carbimazole, carbinoxamine, carbocloral, carbocysteine, carbon tetrachloride, carbonate gel, carboplatin, carboprost, carboprost, carboquone, carbromal, carbubarb, carbutamide, carbuterol, carfimate, carglumic acid, cargutocin, carindacillin, cariporide, cariporide, carisoprodol, carmofur, carmoxirole, carmustine, carnitine, caroverine, caroxazone, carphenazine, carpipramine, carprofen, carsalam, carteolol, cardcaine, carubicin, carumonam, carvacrol, carvedilol, carvone, cascarillin, caspofungin, catechin, cathepsin K inhibitors, cathepsin S inhibitors, CC-401, CCI-779, CCR5 antagonists, CDC-394, CDC-801, CEE-03-310, cefactor, cefadroxil, cefalexin, cefalexin pivoxil, cefamandole, cefatrizine, cefazedone, cefazolin, cefbuperazone, cefcapene pivoxil, cefclidin, cefdinir, cefditoren pivoxil, cefepime, cefetamet, cefetamet pivoxil, cefixime, cefmenoxime, cefmetazole, cefminox, cefodizime, cefonicid, cefoperazone, cefoperazone+sulbactam, ceforanide, cefoselis, cefotazime, cefotetan, cefotiam, cefotiam hexetil, cefoxitin, cefozopran, cefpimizole, cefpiramide, cefpirome, cefpodoxime, cefprozil, cefroxadine, cefsulodin, ceftazidime, cefteram, ceftezole, ceftibuten, ceftizoxime, ceftizoxime, ceftriaxone, cefuroxime, cefuroxime axetil, cefuzonam, celecoxib, celgosivir, celiprolol, cellulose ethyl, CEP-1347, CEP-701, cephacetrile, cephaeline, cephalexin, cephaloglycin, cephaloridine, cephalosporin C, cephalothin, cephapirin, cephradine, cerivastatin, ceronapril, certoparin, ceruletide, cerviprost, cetalkonium, cetamolol, cethexonium, cethromycin, cetiedil, cetirizine, cetirizine, cetirizine+pseudoephedrine, cetotiamine, cetoxime, cetraxate, cetrimonium, cetrorelix, cetyldimethylethyl-ammonium, cetylpyridinium, cevimeline, CG-1521, chaulmoogric acid, chenodiol, CHF-3381, chlophedianol, chloracizine, chloral, chlorambucil, chloramine-B, chloramine-T, chloramino-chloramphenicol, chlorazanil, chlorbenzoxamine, chlorbetamide, chlorcyclizine, chlordantoin, chlorguanide, chlorhexadol, chiorhexidine, chloriazepoxide, chlorisondamine, chlormadinone, chlormerodrin, chlormezanone, chlormidazole, chlomaphazine, chloroazodin, chlorophyll, chloroprednisone, chloroprocaine, chloropyramine, chloroquine, chlorothen, chlorothiazide, chlorotrianisene, chloroxine, chloroxylenol, chlorozotocin, chlorphenamine, chlorphenesin, chlorpheniramine, chlorphenoxamide, chlorphenoxamine, chlorphentermine, chlorproethazine, chlorproguanil, chlorproguanil+dapsone, chlorpromazine, chlorpropamide, chlorprothixene, chlorquinaldol, chlortetracycline, chlorthalidone, chlorthenoxazine(e), chlorzoxazone, cholic acid, choline, choline theophyllinate, choline-L-alfoscerate, chromocarb, chromonar, chrysoidine, CHS-828, CI-1031, CI-1040, cibenzoline, ciclesonide, cicletanine, ciclonicate, ciclopirox, ciclosidomine, ciclosporin A, cidofovir, cifenline, cilansetron, cilastatin, cilazapril, cilengitide, cilnidipine, cilomilast, cilostazol, cimetidine, cimetropium, cinacalcet, cinchonidine, cinchonine, cinchophen, cinepazet, cinepazide, cinepazide, cinitapride, cinmetacin, cinnamedrine, cinnarizine, cinolazepam, cinoxacin, cinoxate, cinromide, cioteronel, cipamfylline, cipralisant, ciprofibrate, ciprofloxacin, ciprofloxacin+ciramadol, cisapride, cisatracurium, cisplatin, citalopram, citicoline, Citiolone, citrate, citric acid, citrulline, cizolirtine, CJ-13610, CKD-602, cladribine, clanobutin, clarithromycin, clavulan, clavulanate disodium, clavulanic acid, clebopride, clemastine, clemizol, clenbuterol, clentiazem, clevidipine, clevudine, clidanac, clidinium, clinafloxacin, clindamycin, clindamycin, clindamycin+tretinoin, clinofibrate, clinprost, clobazam, clobenfurol, clobenoside, clobenzepam, clobenzorex, clobenztropine, clobetasol, clobetasone, clobutinol, clocapramine, clocinizine, cloconazole, clocortolone, clodronate, clodronic acid, clofarabine, clofazimine, clofenamide, clofibrat, clofibric acid, cloflucarban, clofoctol, cloforex, clomacran, clomestrone, clometacin, clomethiazole, clometocillin, clomiphene, clomipramine, clomocycline, clonazepam, clonidine, clonitazene, clonitrate, clonixin, clopamid, clopenthixol, cloperastine, clopidogrel, clopirac, cloprednol, cloranolol, clorazepic acid, clorexolone, cloricromene, clorindione, clorprenaline, clortermine, clospirazine, clostebol, clothiapine, clotiazepam, clotrimazole, clotrimazole+betamethasone, cloxacillin, cloxazolam, cloxotestosterone, cloxyquin, clozapine, CMI-392, CMT-3, CNI-1493, CNS-5161, cobamamide, cocaethylene, cocaine, codeine, cofactor, colchicine, colesevelam, colestilan, colestipol, colforsin daropate, colfosceril, collagraft, colocynthin, colpormon, coluracetam, combretastatin A-4 prodrug, compound B, conivaptin conjugate, connettivina, convallatoxin, coparaffinate, corticorelin ovine, corticosterone, cortisone, cortivazol, cosyntropin, cotamine, cotinine, co-trimazine, coumetarol, CP-248, CP-461, CPC-211, CPI-1189, CRA-0450, creatinol-O-phosphate, CRL-5861, crobenetine, croconazole, cromoglicic acid, cromolyn, cropropamide, crotamiton, crotethamide, crystacide, CS-502, CS-758, CS-834, CT-052923, CT-32228, cupric citrate, cuproxoline, CVT-2584, CX-659S, cyacetacide, cyamemazine, cyanidin, CYC400, cyclacillin, cyclandelate, cyclazocine, cyclexanone, cyclexedrine, cyclidrol, cyclin D1 inhibitors, cyclizine, cyclobarbital, cyclobendazole, cyclobenzaprine, cyclobutyrol, cyclocumarol, cyclodrine, cyclofenil, cycloguanil, cyclomethycaine, cycloniumelodide, cyclopentamine, cyclopenthiazide, cyclopentobarbital, cyclopentolate, cyclophosphamide, cyclopiroxalamine, cycloserine, cyclothiazide, cyclovalone, cymarin, cymserine, cynarin(e), cyp26 inhibitors, cyproheptadine, cyproterone, cysteamine, cystic fibrosis ther, cytarabine, D-24851, D-4418, DA-5018, DA-6034, DA-7867, DA-7911, DA-8159, dacarbazine, daclizumab, dactinomycin, dalbavancin, dalfopristin, dalfopristin+quinupristin, dalteparin, daltroban, danaparoid, danazol, danthron, dantrolene, dapiprazole, dapivirine, dapoxetine, dapsone, daptomycin, darbepoetin alfa, darifenacin, daunorubicin, DAX<SciClone, DB-67, D-camphocarboxylic, DCF-987, DDT, deaminooxytocin, deanol, debrisoquin, decamethonium, decimemide, decitabine, declopramide, deferiprone, deferoxamine, deflazacort, defosfamide, degarelix, dehydroascorbic acid, dehydroemetine, dehyrdocholic acid, delapri+manidipine, delapril, delavirdine, delmadinone, delmopinol, delorazepam, delucemine, demanyl, demecarium, demeclocycline, demecolcine, demegestone, demexiptilline, denaverine, dendrimers, denileukin diftitox, denopamine, denopterin, deoxycholic acid, deoxycorticosterone, deoxydihydro-streptomycin, deoxyepinephrine, depreotide, depsipeptide, deptropine, dequalinium, dersalazine, deserpidine, desferriexamine, desflurane, desipramine, deslanoside, desloratadine, deslorelin, desmopressin, desogestrel, desogestrel+estradiol, desogestrel+ethinylestrad (1), desomorphine, desonide, desoximetasone, detaxtran, devacade, dexamethasone, dexanabinol, dexecadotril, dexefaroxan, dexetimide, dexibuprofen, dexketoprofen, dexloxiglumide, dexmedetomidine, dexmethylphenidate, dexpanthenol, dexrazoxane, dextran-1, dextranomer, dextroamphetamine, dextromethorphan, dextromoramide, dextropropoxyphene, dezocine, DF-1012, DFA-IV, D-fenchone, D-glucuronolactone, Diab II, diacerein, diampromide, diamthazole, diathymosulfone, diatrizoate, diazepam, diaziquone, diazoxide, dibekacin, dibenzepin, dibromopropamidine, dibucaine, dichloralphenazone, dichloramine T, dichlorisone, dichlorobenzyl alcohol, dichlorohydrin, dichlorophen, dichlorphenarsine, dichlorphenamide, diclofenac, diclofenac+HA, dicloxacillin, dicoumarol, dicumarol, dicyclomine, didanosine, dideoxyadenosine, didox, dienestrol, dienogest, dienogest+estradiol, diethadione, diethazine, diethylamide, diethylbromo-acetamide, diethylcarbamazine, diethylpropion, diethylstilbestrol, difemerine, difenamizole, difenoxin, difenpiramide, diflomotecan, diflorasone, difloxacin, diflucortolone, diflunisal, difluprednate, digitalin, digitoxin, digoxin, dihexyverine, dihydralazine, dihydrocodeine, dihydrocodeinone enol, dihydroergocrypdne, dihydroergocryptine, dihydroergotamine, dihydromorphine, dihydrostreptomycin, dihydrotachysterol, dihydroxyaluminum, diisopromine, diisopropyl paraoxon, diisopropylamine, dilazep, dilevalol, diloxanide, diltiazem, dimecrotic acid, dimefline, dimeglumine, dimemorfan, dimenhydrinate, dimenoxadol, dimepheptanol, dimercaprol, dimetacrine, dimethadione, dimethazan, dimethindene, dimethisoquin, dimethisterone, dimethocaine, dimethoxanate, dimethyl sulfoxide, dimethylthiambutene, dimetofrine, dimorpholamine, dinoprostone, diosmectite, diosmin, dioxadrol, dioxaphetyl, dioxethedrine, dioxybenzone, diphemanil, diphenadione, diphencyprone, diphenhydramine, diphenidol, diphenoxylate, diphenylpyraline, diphetarsone, diphtheria & tetanus toxoids and acellular pertussis vaccine adsorbed, dipipanone, dipivefrin, dipyridamole, dipyridamole, dipyrocetyl, dipyrone, diquafosol, dirithromycin, disodium pamidronate, disofenin, disopyramide, distigmine, disulfamide, disulfiram, ditazol, dithiazanine, dithranol, ditiocarb, dixanthogen, dixyrazine, DJ-927, DK-507k, DL-Lactic Acid, DMDC, DMXAA, DNA Stealth, dobesilate, dobutamine, docarpamine, docetaxel, docosahexaenoic acid, docosanol, docusate, dofetilide, dolasetron mesilate, domiodol, domiphen, domitroban, domperidone, donepezil, donitriptan, dopamine, dopexamine, doramapimod, doranidazole, doripenem, dorzolamide, dorzolamide+timolol, dosmalfate, dosulepine, dotarizine, dothiepin, doxacurium, doxapram, doxazosin, doxefazepam, doxenitoin, doxepin, doxercalciferol, doxifluridine, doxofylline, doxorubicin, doxycycline, doxylamine, DPC-817, DPI-3290, DQ-113, drofenine, droloxifene, drometrizole, dromostanolone, dronabinol, dronedarone, droperidol, droprenilamine, dropropizine, drospirenone, drotaverine, drotebanol, droxicam, droxidopa, droxidopa, DU-125530, duloxetine, duramycin, durapatite, dutasteride, DW-1141, DW-286a, DW-471, DX-9065a, DY-9760e, dyclonine, dydrogesterone, dymanthine, dyphyllin, E-1010, E-2101, E2F antagonists, E-3620, E-5564, E-5842, E-6259, EAA-90, ebastine, eberconazole, ebrotidine, ebselen, ebumamonine, ecabapide, ecabet, ecadotril, ecgonidine, ecgonine, echothiophate, econazole, ecopipam, ecraprost, ectylurea, ED-71, edaravone, edatrexate, edetate calcium disodium, edetate disodium, edetate sodium, edetate trisodium, edonentan, edotreotide, edoxudine, edrecolomab, edrophonium, efalith, efaproxiral, efavirenz, efletirizine, eflornithine, efloxate, eflucimibe, efonidipine, EGIS-7229, eglumegad, egualen, elarofiban, elcatonin, elcosapentaenoic acid, eledoisin, eletriptan, elgodipine, ellagic acid, elliptinium, eltoprazine, elvucitabine, elzasonan, embelin, embramine, emedastine, emepronium, emetine, emitefur, EMM-210525, emodin, emorfazone, EMR-62203, emtricitabine, emylcamate, enalapril, enalaprilat, enallylpropymal, encainide, enciprazine, endralazine, enfenamic acid, enflurane, enilconazole, eniluracil, ENMD-0995, enocitabine, enol-3-IPA, enoxacin, enoxaparin, enoximone, enoxolone, enprostil, enrasentan, entacapone, entecavir, enviomycin, eoinephrine, epalrestat, epavir, EPC-K1, eperisone, epervudine, ephedrine, epicillin, epimestrol, epinastine, epirizole, epirubicin, epitiostanol, eplerenone, eplivanserin, epoprostenol, epostane, eprazinone, epristeride, eprosartan, eprozinol, eptapirone, eptaplatin, eptastigmine, eptazocine, eptifibatide, equilenin, equilin, ERA-923, erdosteine, ergocomine, ergocominine, ergoloid mesylates, ergonovine, ergosterol, ergotamine, eritadenine, erlotinib, ertapenem, erythrityl tetranitrate, erythrocentaurin, erythromycin acistrate, erythromycin erythrophleine, erythromycin estolate, erythromycin glucoheptonate, erythromycin lactobionate, erythromycin propionate, erythromycin stearate, erythromycin stinoprate, esaprazole, escitalopram, esculin, eseridine, esmolol, esomeprazole, estazolam, ester, estradiol, estradiol, estramustine, estriol, estrogen, estrone, eszopiclone, etafedrine, etafenone, etamiphyllin, etanercept, etanidazole, etaqualone, eterobarb, ethacridine, ethacrynic acid, ethadion, ethambutol, ethamivan, ethamsylate, ethanolamine, ethaverine, ethchlorvynol, ethenzamide, ethiazide, ethinamate, ethinyl estradiol, ethinyl estradiol, ethinyl estradiol, ethionamide, ethisterone, ethoheptazine, ethopropazine, ethosuximide, ethotoin, ethoxzol amide, ethybenztropine, ethyl alcohol, ethyl biscoumacetate, ethyl chloride, ethyl dibunate, ethyl ether, ethyl icosapentate, ethyl loflazepate, ethyl loflazepate, ethylamine, ethylene, ethylestrenol, ethylidene, ethylmethyl-thiambutene, ethylmorphine, ethylnorepinephrine, ethynodiol, ethynylcytidine, etidocaine, etidronate, etidronic acid, etifelmin, etifoxine, etilefrin, etilevodopa, etiprednol, etiroxate, etizolam, etodolac, etodroxizine, etofenamate, etofibrate, etofylline, etofylline clofibrate, etofylline nicotinate, etoglucid, etomidate, etomidoline, etonitazene, etonogestrel, etoperidone, etoposide, etoposide phosphate, etoricoxib, etoxadrol, etozolin, etretinate, etryptamine, etymemazine, eucatropine, eugenol, EUK-134, EUK-189, evans blue, everolimus, exalamide, exametazime, exatecan, exemestane, exifone, exisulind, Exosurf®, ezetimibe, Factor IX, Factor VIII, Factor XIII, fadolmidine, fadrozole, falecalcitriol, famciclovir, famotidine, fampridine, fandofloxacin, fantofarone, faropenem, faropenem daloxate, fasidotril, fasudil, fazadinium bromide, febarbamate, febuprol, febuxostat, fedotozine, felbamate, felbinac, felodipine, felypressin, femoxetine, fenbenicillin, fenbufen, fenbutrazate, fencamfamine, fencamine, fenclozic acid, fendiline, fendosal, fenethylline, fenfluramine, fenipentol, fenofibrate, fenoldopam, fenoprofen, fenoterol, fenoverine, fenoxazoline, fenoxedil, fenozolone, fenpentadiol, fenpiprane, fenpiverinium, fenproporex, fenquizone, fenretinide, fenspiride, fentanyl, fentiazac, fenticlor, fenticonazole, fentonium bromide, fepradinol, feprazone, ferric sodium edetate, ferriexamine B, ferrocholinate, ferrous gluconate, ferumoxytol, fesoterodine, fexofenadine, fibrostat, fidarestat, ftduxosin, finasteride, finrozole, fipexide, FK-960, flavopiridol, flavoxate, flecainide, fleroxacin, flesinoxan, flibanserin, floctafenine, flomoxef, flopropione, florantyrone, flosequinan, floxacillin, floxuridine, fluacizine, fluanisone, fluarizine, fluasterone, fluazacort, flucloronide, flucloxacillin, fluconazole, flucytosine, fludarabine, fludeoxyglucose F18, fludiazepam, fludrocortisone, flufenamic acid, fluindione, flumazenil, flumecinol, flumequine, flumethasone, flumethiazide, flunisolide, flunitrazepam, flunoxaprofen, fluocinolone acetonide, fluocinolone SAL, fluocinonide, fluocortin butyl, fluocortolone, fluorescein, fluoresone, fluorometholone, fluorosalan, fluorouracil, fluoxetine, fluoxymesterone, flupentixol, fluperolone, fluphenazine, flupirtine, fluprednidene acetate, fluprednisolone, fluproquazone, flurandrenolide, flurazepam, flurbiprofen, flurithromycin, flurogestone, flurothyl, fluroxen, fluspirilene, flutamide, flutazolam, fluticasone, flutoprazepam, flutrimazole, flutropium bromide, fluvastatin, fluvoxamine, folic acid, folinic acid, fomepizole, fominoben, fomivirsen, fomocaine, fonazine, fondaparinux, formebolone, formestane, formocortal, formoterol, fosamprenavir, foscarnet, fosfestrol, fosfluconazole, fosfomycin, fosfomycin, fosfosal, fosinopril, fosphenytoin, fotemustine, fropenem, frovatriptan, fructose, fructose-1,6-diphosphate, FTC, FTY-720, fudosteine, fulvestrant, fumagiline, fumagillin, furaltadone, furazabol, furazolidone, furazolium chloride, furonazide, furosemide, fursultiamine, furtrethonium, fusidic acid, G1, YM BioSciences, G25, GABA-A Alphas, gabapentin, gabexate, gaboxadol, gadobenat, gadobutrol, gadodiamide, gadolinium, gadopentetic acid, gadoteridol, gadoversetamide, gadoxetic acid, galantamine, galanthamine, galarubicin, gallamine triethiodide, gallic acid, gallium maltolate, gallium nitrate, gallopamil, ganaxolone, ganciclovir, ganirelix, ganstigmine, gantofiban, garenoxacin, gamocestim, gatifloxacin, gefamate, gefitinib, gemcabene, gemcitabine, gemeprost, gemfibrozil, gemifloxacin, gentamicin, gentian violet, gentiopicrin, gentisic acid, gepefrine, gepirone, gestodene, gestodene+ethinylest, gestonorone caproate, gestrinone, gimatecan, giractide, gitoxin, GL-406349, Glafenine, glatiramer, Glibomuride, gliclazide, glimepiride, glipizide, gliquidone, glisolamide, glisoxepid, globulin (human), glucametacin, glucoheptonic acid, gluconic acid, glucosamine, glucosulfone, glufosfamide, glutamic acid, glutaraldehyde, glutethimide, glyburide, glybuthiazol(e), glybuzole, glycerol, glycerophosphate, glycocyamine, glycol salicylate, glyconiamide, glycopyrrolate, glyhexamide, glymidine, glypinamide, GMDP, gold sodium, goserelin, GPI-1485, GPI-5693, graftskin, granisetron, grepafloxacin, griseofulvin, guaiacol, guaiapate, guaiazulene, guaifenesin, guaimesal, gualacolsulfonate, guamecycline, guanabenz, guanadrel, guanethidine, guanfacine, guanoxabenz, guanoxan, gugulipid, gusperimus, GW-280430A, GW-320659, GYKI-16084, hachimycin, halazepam, halcinonide, halobetasol, halofantrine, halometasone, haloperidol, halopredone, haloprogin, halopropane, halothane, haloxazolam, harkoseride, HE-2000, heal os, hematoporphyrin, hepronicate, heptabarbital, heptaminol, hetacillin, hetastarch, hexacetonide, hexachlorophene, hexadimethrine, hexafluorenium, hexamethonium, hexamidine, hexapropymate, hexedine, hexestrol, hexestrol Bis(β-diethylaminoethyl ether), hexethal, hexedine, hexobarbital, hexobendine, hexocyclium methyl sulfate, hexoprenaline, hextend, hexylcaine, HF-0299, HGP-2, HGP-6A, hidrosmin, histamine, Histapyrrodine, histrelin, HM-101, HMN-214, homatropine, homocamfin, homochlorcyclizine, hopantenic acid, HP-228, huperzine A, hyaluronan, hycanthone, hydnocarpic acid, hydralazine, hydrastine, hydrastinine, hydrochlorothiazide, hydrocodone, hydrocortamate, hydrocortisone, hydrocortisone, hydroflumethiazide, hydromorphone, hydroquinidine, hydroquinine, hydroquinone, hydroxid, hydroxocobalamin, hydroxyamphetamine, hydroxychloroquine, hydroxydione, hydroxyethyl ether, hydroxynaphthoate, hydroxypethidine, hydroxyphenamate, hydroxypropyl cellulose, hydroxystilbamidine, hydroxytetracaine, hydroxyzine, Hylan G-F 20, hymecromone, hyoscyamine, hypericin, IACFT, ibandronic acid, ibopamine, ibopamine, Ibritumomab, ibrolipim, ibudilast, Ibufenac, ibuprofen, ibuprofen piconol, ibuproxam, ibutilide, ICA-17043, icodextrin, idarubicin, Idazoxan, IdB-1016, idebenone, IDN-5109, idoxifen, idraparinux, idrocilamide, ifenprodil, ifosfamide, iguratimod, ilaprazole, ilomastat, iloperidone, iloprost trometamol, ILX23-7553, imatinib, imidapril, imidazole salicylate, imipenem, imipramine, imipramine N-Oxide, imiquimod, imolamine, implitapide, improsulfan, inactivated, inaperisone, incadronate, incadronic acid, indalpine, indanazoline, indapamide, indecainid, indeloxazine, indeloxazine, indenolol, indinavir, indiplon, indisetron, indisulam, indobufen, indocyanine green, indometacin, indoprofen, indoramin, induclem, infliximab, inhibitor, inhibitors, inosine pranobex, inositol, inositol niacinate, inverse agonist Mer, iobenguane, iobenzamic acid, iobitridol, iocarmic acid, iocetamic acid, iodamide, iodide, iodine, iodipamide, iodixanol, iodoalphionic acid, iodochlorhydroxyquin, iodoform, iodopyracet, iodopyrrole, iodoquinol, iodosubgallate, iofetamine 123I, ioglycamic acid, iohexol, iomeglamic acid, iomeprol, iopamidol, iopanoic acid, iopentol, iophendylate, iophenoxic acid, iopromide, iopronic acid, iopydol, iopydone, iothalamic acid, iotrolan, ioversol, ioxaglic acid, ioxilan, IP-751, ipidacrine, IPL-576092, ipodate, iponiazid, ipratpopium, ipratropium, ipratropium bromide, iprazochrome, ipriflavone, iprindole, iproclozid, ipsapiron, irbesartan, IRFI-042, IRFI-165, iridomyrmecin, irindalone, irinotecan, irofulven, iron sorbitex, irsogladine, IS-741, isaglitazone, ISAtx-247, isbogrel, isepamicin, isoaminile, isobutyl p-aminobenzoate, isoconazole, isoetharine, isofloxythepin, isoflurane, isoflurophate, isoladol, isomethadone, isometheptene, isoniazid, isonixin, isopromethazine, isopropamide iodide, isopropyl alcohol, isopropyl unoprostone, isoproterenol, isosorbide, isosorbide dinitrate, isosorbide mononitrate, isothipendyl, isotretinoin, isovaleryl, isoxepac, isoxicam, isoxsuprine, isradipine, israpafant, ISV-403, itasetron, ITF-282, itopride, itraconazole, itramin, itriglumide, iturelix, ivabradine, ixabepilone, J-104132, J-107088, J-113397, Janex-1, josamycin, JTV-519, K-777, kainic acid, kalimate, kallidin, KB-130015, KCB-328, kebuzone, ketamine, ketanserin, ketazolam, kethoxal, ketobemidone, ketoconazole, ketoprofen, ketorolac, ketorolac, ketotifen, khellin, kinetin, KNI-272, KP-103, KP-157, KP-544, KRN-5500, KT-136, KUL-7211, KW-2170, KW-6002, KW-7158, L-365260, L-5-hydroxy-tryptophan, L-745337, L-758298, L-826141, labetalol, lacidipine, lactic acid, lactitol, lactulose, lafutidine, lamifiban, lamivudine, lamotrigine, landiolol, lanicemine, laniquidar, lanoconazole, lanoteplase, lanreotide, lansoprazole, lanthanum carbonate, lapatinib, laquinimod, lasofoxifene, latamoxef, latanoprost, lauroguadine, laurolinium acetate, lawsone, LAX-111, lazabemide, LB-30057, L-cysteine, lefetamine, leflunomide, leflunomide, leiopyrrole, lenampicillin, lentinan, lepirudin, lercanidipine, lerisetron, lesopitron, leteprinim, letosteine, letrozole, leucocyanidin, leuprolide, leuprolide acetate, leuprorelin, levallorphan, levaminsole, levcromakalim, levetiracetam, levobetaxolol, levobunolol, levobupivacaine, levocabastine, levocetirizine, levodopa, levodropropizine, levofloxacin, levomethadyl acetate, levomoprolol, levonorgestrel, levophacetoperane, levopropoxyphene, levorphanol, levosimendan, levosulpride, levothyroxine, levovirin, lexidronam, lexipafant, LF-15-0195, LF-16-0687, LCD-1550, LH, LH-RH, liarozote, licofelone, licostinel, lidadronate, lidamidine, lidocaine, lidofenin, lidoflazine, limaprost, lincomycin, lindan, linezolid, linoleic acid, linolenic acid, liothyronine, lipase, lipo-dexamethasone, lipo-flurbiprofen, Lipogel HA, LiquiVent, liranaftate, lisinopril, lisofyllin, lisuride, lithium, lithium citrate, lixivaptan, LJP-1082, LLUAlpha, LMP-160, LMP-420, loanzapine, lobaplatin, lobeline, lobenzarit, lodoxamide, lofentanil, lofepramine, lofexidine, loflucarban, lomefloxacin, lomerizine, lomifylline, lomustine, lonafamib, lonapalene, lonazolac, lonidamine, loperamide, loperamide oxide, loprazolam, loprinone, loracarbef, lorajmine, loratadine, lorazepam, lorcainide, lormetazepam, lomoxicam, losartan, loteprednol, lotrafiban, lovastatin, loxapine, loxiglumide, loxoprofen, Lu-35-138, lubeluzole, lubiprostone, lucanthone, lucanthone, lumefantrine, lumiracoxib, lurtotecan, lutetium texaphyrin, LV-216, LX-104, LY-156735, LY-293111, LY-293558, LY-355703, lyapolate, lymecycline, lynestrenol, lypressin, lysine acetylsalicylate, lysine salicylate, lysophospholipids, M-40403, mabuprofen, mabuterol, macrophage colony-stimulating factor, MADU, mafenide, mafosfamide, magaldrate, magenta I, magnesium, magnesium carbonate, magnesium chloride, magnesium citrate, magnesium gluconate, magnesium lactate, magnesium salicylate, malathion, malotilate, mandelic acid, mandelic acid isoamyl, mangafodipir, manidipine, mannomustine, mannose-6-phosphate, maprotilline, maribavir, marimastat, maxacalcitol, mazindol, mazipredone, MC-5723, MCC-478, MCI-154, m-cresyl acetate, MDAM, MDI-101, MDI-403, MDL-100907, mebendazole, mebeverine, mebhydroline, mebrofenin, mebutamate, mecamylamine, mechlorethamine, mechlorethamine oxide, mecillinam, meclizine, meclocycline, meclofenamate, meclofenamic acid, meclofenoxate, mecloqualone, mecysteine, medazepam, medifoxamine, medrogestone, medronic acid, medroxyprogesterone, medrysone, mefenamic acid, mefenorex, mefexamide, mefloquine, mefruside, megestrol, meglumin, meglutol, melagatran, melanocortin-4 agonist, melarsoprol, melengestrol, melevodopa, melinamide, melitracen, meloxicam, melperone, melphalan, meluadrine, memantine, MEN-10700, MEN-10755, menadiol, menadione, menadoxime, menbutone, menogaril, MENT, menthol, menthyl valerate, meobentine, meparfynol, mepartricin, mepazine, mepenzolate bromide, meperidine, mephenesin, mephenoxalone, mephentermine, mephenytoin, mephobarbital, mepindolol, mepitiostane, mepivacaine, mepixanox, meprednisone, meprobamate, meproscillarin, meptazinol, mequitazine, meralein, meralluride, merbromin, mercaptomerin, mercumallylic acid, mercuric oleate, mercuric oxycyanide, merimepodib, meropenem, mersalyl, mertiatide, mesalamine, mesalazine, mesna, mesoridazine, mestanolone, mesterolone, mestranol, mesulfen, metaclazepam, metampicillin, metapramine, metaproterenol, metaraminol, metazocine, metergoline, metformin, methacholine, methacycline, methadone, methafurylene, methamphetamine, methandriol, methandrostenolone, methantheline, methapyrilene, methaqualone, metharbital, methazolamide, methdilazine, methenamine, methenolone, methestrol, methetoin, methicillin, methimazole, methiodal, methionic acid, methionine, methisazone, methitural, methixene, methocarbamol, methohexital, methotrexate, methotrimeprazine, methoxamine, methoxsalen, methoxycinnamate, methoxyflurane, methoxyphenamine, methoxypromazine, methscopolamine, methsuximide, methyclothiazide, methyl blue, methyl nicotinate, methyl propyl ether, methyl salicylate, methyl tert-butyl ether, methylbenzethonium chloride, methylbromide, methylcobalamin, methyldopa, methylene blue, methylergonovine, methylhexaneamide, methylphenidate, methylprednisolone, methyl prednisolone, methylprednisolone, methylthiouracil, methyltrienolone, methyprylon, methysergide, metiazinic acid, metipranolol, metoclopramide, metocurine iodide, metofenazate, metolazone, metopimazine, metopon, metoprolol, metralindole, metrizamide, metrizoic acid, metron s, metyrapone, metyrosine, mexazolam, mexenone, mexiletine, mezlocillin, MFH-244, mianserin, mibefradil, miboplatin, micafungin, miconazole, micronomicin, midaxifyline, midazolam, midecamycin, midecamycin acetate, midesteine, midodrine, midostaurin, mifepristone, miglitol, miglustat, mildronate, milnacipran, miloxacin, milrinone, miltefosine, minaprine, minocycline, minodronic acid, minoxidil, miokamycin, mirtazapine, misoprostol, mitemcinal, mitiglinide, mitobronitol, mitoguazone, mitolactol, mitomycin, mitotane, mitoxantrone, mitoxantrone, MIV-210, mivacurium, mivazerol, mizolastine, mizoribine, MKC-733, MLN-519, MLN-576, moclobemide, modafinil, moexipril, mofarotene, mofebutazone, mofegiline, mofetil, mofezolac, MOL-6131, molindone, molsidomine, mometasone, monatepil, monobenzone, monoethanolamine, monolaurin, monoterpene diols, montelukast, monteplase, moperone, mopidamol, moprolol, moracizine, morazone, moricizine, moroxydine, morphazinamide, morphine, morphine-6-glucuronide, mosapramine, mosapride, motexafin, motretinide, moveltipril, moxalactam, moxastine, moxaverine, moxestrol, moxifloxacin, moxisylyte, moxonidine, M-PGA, MPI-5010, MPI-5020, MPL, MRS-1754, MS-209, MS-275, MS-325, MS-377, mupirocin, muscarin, muzolimine, MX-1013, mycophenolate, mycophenolic acid, myrophine, N-(hydroxymethyl)-nicotinamide, N,N,N',N'-tetraethylphthalamide, N-[4-[4-(2-methoxyphenyl)-1-piperazinyl]butyl]naphthalene-2-carboxamide, N2-formyl-sulfisomidine, N4-sulfanilylsulfanilamide, N4-β-D-glucosylsulfanilamide, nabilone, nabumetone, N-acetylcysteine, N-acetylmethionine, nadifloxacin, nadolol, nadoxolol, nafamostat, nafarelin, nafcillin, nafronyl, naftidofuryl, naftifine, naftopidil, nalbuphine, nalidixic acid, nalmefene, nalorphine, naloxone, naltrexone, NAMI, naminidil, nandrolone, napadisilate, naphazoline, naphthalene, naproxen, naproxen betainate, naratriptan, narceine, narcobarbital, natamycin, nateglinide, N-butyldeoxy-nojirimycin, N-butylscopolammonium Bromide, NC-503, NC-531, NCX-1000, NCX-4016, NCX-456, NCX-950, n-docosanol, NE-100, nealbaibital, nebivolol, nebostinel, nebracetam, nedaplatin, nedocromil, nefazodone, nefiracetam, nefopam, negamycin, nelfmavir, nemonapride, neostigmine, nepadutant, neramexane, neridronic acid, neriifolin, N-ethylamphetamine, neticonazole, netilmicin, nevirapine, NGD-98-2, nialamide, niaprazine, nicametate, nicaraven, nicardipine, nicergoline, niceritrol, niclosamide, nicoclonate, nicofuranose, nicomol, nicomorphine, nicorandil, nicotinamide, nicotine, nicotinic acid, nicotinic acid benzyl ester, nicotinyl alcohol, nifedipine, nifekalant, nifenalol, niflumic acid, nifuratel, nifurfoline, nifuroxazide, nifuroxime, nifurpirinol, nifurprazine, nifurtimox, nifurtoinol, nifurzide, NIK-254, nikethamide, nilutamide, nilvadipine, nimesulide, nimetazepam, nimodipine, nimorazole, nimustine, ninopterin, NIP-142, NIP-531, niperotidine, nipradilol, niridazole, nisoldipine, nitazoxanide, nitisinone, nitracrine, nitrazepam, nitrendipine, nitroflurbiprofen, nitrofurantoin, nitrofurazone, nitroglycerin, nitromersol, nitronaproxen, nitroxazepine, nitroxoline, nizatidine, nizofenone, NM-3, NM-702, N-methylephedrine, N-methylepinephrine, N-methylglucamine, NN-414, NNC-05-1869, nobel, nogalamycin, nolatrexed, nolomirole, nolpitantium, nomegestrol, nomifensine, noprylsulfamide, norbolethone, nordazepam, nordefrin, nordihydroguaiaretic acid, norelgestromin, norepinephrine, norethandrolone, norethindrone, norethynodrel, norfenefrine, norfloxacin, norgesterone, norgestimate, norgestrel, norgestrienone, norlevorphanol, normethadone, normethandrone, normorphine, norphenazone, norpipanone, norpseudoephedrine, nortriptyline, norvinisterone, noscapine, novembichin, novobiocin, noxiptillin, noxythiolin, NS-1209, NS-1231, NS-126, NS-220, NS-2330, NS5A inhibitors, NS-7, NS-8, NSC-330507, NSC-619534, NSC-697726, N-sulfanilyl-3,4-xylamide, NU-6027 nucleosides, NV-07, NVP-SRA880, NW-1029, NXY-059, Nylidrin, NZ-314, NZ-419, obidoxime chloride, OC-108, ocinaplon, octabenzone, octacaine, octamoxin, octaverine, octenidine, octodrine, octopamine, octotiamine, octreotide, octyl, ofloxacin, oleandrin, oleic acid, olmesartan-medoxomil, o-Iodohippurate, olopatadine, olpadronic acid, olsalazine, oltipraz, OM-294DP, omacor, omapatrilat, omeprazole, omiloxetine, omoconazole, onapristone, ondansetron, ONO-3403, ONO-4128, ONO-8815 Ly, ONT-093, OPC-14523, OPC-31260, OPC-51803, OPC-6535, opiniazide, opioid analgesics, opipramol, orazamide, orazipone, Org-12962, Org-24448, oritavancin, orlistat, ormeloxifene, omidazole, omipressin, ornithine, omoprostil, orotic acid, orphenadrine, orthocaine, osalmid, osanetant, osaterone, oseltamivir, OSI-7836, OSI-7904, ospemifene, otilonium bromide, ouabain, oxaceprol, oxacillin, oxaflozane, oxaliplatin, oxalyt-C, oxamarin, oxametacine, oxamniquine, oxandrolone, oxantel, oxapropanium, oxaprozin, oxatomide, oxazepam, oxazolam, oxcarbazepine, oxeladin, oxendolone, oxethazaine, oxetoron, oxiconazole, oxidronic acid, oxiniacic acid, oxiracetam, oxitropium, oxolamin, oxolinix acid, oxophenarsine, oxprenolol, oxybenzone, oxybutynin, oxycinchophen, oxycodone, oxygent, oxymesterone, oxymetazoline, oxymetholone, oxymethurea, oxymorphone, oxypendyl, oxypertine, oxyphenbutazone, oxyphencyclimine, oxyphenisatin, oxyphenonium, oxypinocamphone, oxypurinol, oxytedrine, oxytetracycline, ozagrel, p-(benzylsulfonamido)-benzoic acid, P-100, P-1202, P32/98, PA-824, PACAP 38, pactitaxel, PADRE, pagoclone, PAI inhibs, palindore, palivizumab, palonosetron, pamabrom, pamaquine, pamicogral, pamidronate, p-aminobenzoic acid, p-aminohippuric acid, p-amino-propiophenone, p-aminosalicylic acid, panavir, pancuronium, panipenem, pantethine, pantoprazole, pantothenic acid, papain, papaverine, paracetamol, paraflutizide, paraldehyde, paramethadione, paramethasone, paranyline, parathyroid hormone, parecoxib, parethoxycaine, pargyline, paricalcitol, paromomycin, paroxetine, paroxypropione, parsalmide, patrin-2, pazinaclone, pazufloxacin, p-bromoacetanilide, PC-NSAIDs, PD-0166285, pecilocin, pefloxacin, pegvisomant, pelletierine, pemetrexed, pemirolast, pemoline, pempidine, PEN-203, penamecillin, penbutolol, penciclovir, penethamate, penfluridol, penicillamine, penicillin G, penicillin G Procaine, penicillin N, penicillin O, penicillin V, penimepicycline, penntuss, pentaerythritol, pentaerythritol, pentaerythritol chloral, pentagastrin, pentagestrone, pentalyte, pentam thonium, pentamidine, pentazocine, pentetate, pentetic acid, pentetreotide, penthienate, pentifyllin, pentigetide, pentisomide, pentobarbital, pentolinium, pentorex, pentosan, pentostatin, pentoxifylline, pentoxyl, pentrinitrol, pentylenetetrazole, peplomycin, peptide, peptide, perazine, perfiromycin, perflubron, perfosfamide, pergolide, perhexiline, pericyazine, perifosine, perillyl alcohol, perimethazine, perindopril, periodyl, perisoxal, perlapine, permanganate, permethrin, perospirone, perphenazine, petroleum benzin, PH-10, phanquinone, pharmacor, pharmaprojects no. 6362, pharmaprojects no. 4994, pharmaprojects no. 5325, pharmaprojects no. 5972, pharmaprojects no. 6446, pharmaprojects no. 6590, pharmaprojects no. 6656, pharmaprojects no. 6691, pharmaprojects no. 6743, pharmaprojects no. 6748, phenacaine, phenacemide, phenacetin, phenadoxone, phenallymal, phenamet, phenamide, phenazocine, phenazopyridine, phenbutamide, phencyclidine, phendimetrazine, phenelzine, phenesterine, phenetharbital, phenethicillin, pheneturide, phenformin, phenglutarimide, phenindamine, phenindione, pheniprazine, pheniramine, phenmetrazine, phenobarbital, phenobutiodil, phenocoll, phenoctide, phenolphthalein, phenolphthalol, phenolsulfonphthalein, phenol-tetrachlorophthalein, phenoperidine, phenosulfazole, phenoxybenzamine, phenoxypropazine, phenprobamate, phenprocoumon, phenserine, phensuximide, phentermine, phentetiothalein, phentolamine, phenyl acetylsalicylate, phenyl aminosalicylate, phenyl salicylate, phenylbutazone, phenylephrine, phenylethanolamine, phenylmercury, phenylmethylbarbituric acid, phenylpropanolamine, phenylpropyl-methylamine, phenyltoloxamine, phenyramidol, phenytoin, phethenylate, phloroglucinol, pholcodine, pholedrine, phoramide, phosphate, phosphate, phosphocreatine, phosphocysteamine, phosphorylcholine, phthalylsulfathiazole, phthalylsulfacetamide, p-hydroxyephedrine, phylloquinone, physostigmine, phytic acid, PI-88, piberaline, piboserod, picilorex, picloxydine, picoperine, picosulfate, picotamide, picumast, pidotimod, pifamine, piketoprofen, pildralazine, pilocarpine, piloplex, pilsicainide, pimeclone, pimecrolimus, pimefylline, pimilprost, piminodine, pimobendan, pimozide, pinacidil, pinaverium, pinazepam, pindolol, pioglitazone, pipacycline, pipamazine, pipamperone, pipazethate, pipebuzone, pipecurium, pipecuronium, pipemidic acid, pipenzolate bromide, piperacetazine, piperacillin, piperazine adipate, piperidione, piperidolate, piperilate, piperine analogues, piperocaine, piperonal, piperoxan, piperylone, pipobroman, piposulfan, pipotiazine, pipoxolan, pipradrol, piprozolin, piracetam, pirarubicin, pirazolac, pirbuterol, pirenoxine, pirenzepine, piretanide, pirfenidone, piribedil, piridocaine, pirifibrate, piritramide, piritrexim, pirlindole, pirmenol, piroctone, piroheptine, piromidic acid, piroxicam, piroxicam betadex, piroxicam cinnamate, pirozadil, pirprofen, pitavastatin, pivagabine, pivaloyloxymethyl, pivalylbenzhydrazine, pivampicillin, pivampicillin/pivmecillinam, pivcefalexin, pivmecillinam, pixantrone, pizotifen, pizotyline, PKI-166, p-lactophenetide, plaftbride, plasminogen activator, plasmocid, platonin, plaunotol, PLD-118, PLD-147, pleconaril, plicamycin, p-methyldiphenhydramine, PMS-601, Pneumococcal, PNU-288034, podophyllotoxin, polaprezinc, poldine methylsulfate, policresulen, polidexide, polidocanol, poliovirus vaccine, poly-ADPRT inhibitors, polyestradiol, polyphenon E, polythiazide, porfimer, posaconazole, posatirelin, potassium, potassium, potassium, potassium chloride, potassium gluconate, potassium p-aminobenzoate, povidone, povidone-iodine, PP-117, PR-2699, PR-608, practolol, prajmaline, pralidoxime, pralnacasan, pramipexole, pramiracetam, pramiverin, pramlintide, pramoxine, pranidipine, pranlukast, pranoprofen, prasterone, pratosartan, pravastatin, prazepam, praziquantel, prazosin, prednicarbate, prednimustine, prednisolone, prednisolone 21-diethylaminoacetate, prednisolone famesil, prednisolone sodium, prednisone, prednival, prednylidene, pregabalin, pregnan-3α-ol-20-one, premarin+trimegestone, prenalterol, prenoxdiazine, prenylamine, prezatide, pridinol, prifinium, prilocaine, primaquine, primidone, prinomastat, PRO-2000, probenecid, probucol, procainamide, procaine, procarbazine, procaterol, prochlorperazine, procodazol, procyclidine, procymate, prodipine, proflavine, progabide, progesterone, proglumetacin, proglumide, proheptazine, prolactin, prolintane, prolonium, promazine, promedol, promegestone, promestriene, promethazine, pronethalol, propacetamol, propafenone, propagermanium, propallylonal, propamidine, propane-1,2-diol, propanidid, propantheline, proparacaine, propatyl, propenidazole, propentofylline, propicillin, propiomazine, propionic acid, propionyl 1-carnitine, propipocaine, propiram, propiverine, propizepine, propofol, propoxycaine, propoxyphene, propranolol, propylhexedrine, propyliodone, propylthiouracil, propyphenazone, proquazone, proscillaridin, prostacyclin, prostaglandin E1, prostaglandin E2, prostaglandin F2α, prosultiamine, protein C, protheobromine, prothipendyl, protiofate, protionamide, protizinic acid, protoanemonin, protoklol, protoporphyrin IX, protriptyline, pro-urokinase, proxazole, proxetil, proxibarbal, proxigermanium, proxyphylline, prozapine, prucalopride, prulifloxacin, pseudococaine, pseudoephedrine, pseudoephedrine, pseudoephedrine+triprolidine, psilocybin, PSK-3841, p-sulfanilyl-benzylamine, PT-141, pteropterin, puromycin, PX-12, pyrantel, pyrazinamide, pyridinol carbamate, pyridostigmine, pyridoxal 5-phosphate, pyridoxine, pyrilamine, pyrimethamine, pyrinoline, pyrisuccideanol, pyrithione, pyrithyldione, pyritinol, pyrocatechol, pyrogallol, pyronaridine, pyrophosphate, pyrovalerone, pyroxylin, pyrrobutamine, pyrrocaine, pyrrolntrin, pyrvinium pamoate, quazepam, quercetin, quetiapine, quinacillin, quinacrine, quinagolide, quinapril, quinaprilat, quinapyramine, quinbolone, quinestradiol, quinestrol, quinethazone, quinfamide, quinidine, quinine, quinocide, quinupramine, quinupristin, R-107500, R-667, rabeprazole, racecadotril, racemethorphan, raloxifene, raltitrexed, ramatroban, ramifenazone, ramipril, ramosetron, Ramot project No. 1097, ranimustine, ranitidine, ranitidine bismuth, ranolazine, ranpimase, rapacuronium, rasagiline, raubasine, ravuconazole, raxofelast, razoxane, RC-529, rebamipide, rebimastat, reboxetime, remacemide, remifentanil, reminetant, remoxipride, renzapride, repaglinide, repertaxin L-lysine salt, repinotan, repirinast, reposal, reproterol, rescimetol, rescinnamine, reserpiline, reserpine, resibufogenin, resiquimod, resorcinol, reteplase, retigabine, retinoic acid, revimid, R-flurbiprofen, rho (D) immune, rho-kinase inhibitors, ribavirin, riboflavin, ribostamycin, ricinoleic acid, ridogrel, rifabutin, rifalazil, rifametane, rifamide, rifampicin+trimethoprim, rifampin, rifamycin SV, rifapentine, rifaximin, rifaximine cream, rilmazafone, rilmenidine, riluzole, rimantadine, rimazolium, rimexolone, rimiterol, rimonabant, riodoxol, rioprostil, risedronate, risedronic acid, risperidone, ritanserin, ritipenem, ritodrine, ritonavir, rituximab, rivastigmine, rizatriptan, RJR-2403, RNA Stealth, Ro-0094889, Ro-61-1790, rociverine, rocuronium, rofecoxib, roflumilast, rokitamycin, rolipram, rolitetracycline, romurtide, ronifibrate, ropinirole, ropivacaine, roquinimex, rosaprostol, rosaramicin, rose bengal, rosiglitazone, rosoxacin, rostaporfin, rosuvastatin, rotigotine, rotraxate, roxarsone, roxatidine, roxifiban, roxindol, roxithromycin, RPR-109881 A, RPR-130401, R-roscovitine, RS-0406, RSR-13, rubijervine, rubitecan, ruboxistaurin, rufinamide, rufloxacin, rupatadine, rutin, RWJ-54428, S-0139, S-15535, S-18886, S-34730, S-3578, S-36496, S-36527, S-5751, S-8510, S-8921, sabcomeline, sabeluzole, S-adenosylmethionine, safinamide, salacetamide, salazosulfadimidine, salbutamol, salicin, salicyl alcohol, salicylamide, salicylamide O-acetic acid, salicylanilide, salicylic acid, salicylsilfuric acid, salinazid, salmeterol, salsalate, salverine, samarium $^{153}$Sm, sampatrilat, sancycline, saperconazole, sapropterin, saquinavir, saralasin, saredutant, saredutant, sarizotan, sarizotan, sarpogrelate, sarpogrelate, satigrel, satigrel, satraplatin, satraplatin, satumomab, satumomab, SB-237376, SB-237376, SB-238039, SB-238039, SB-277011, SB-277011, scarlet red, SCH-00013, SCH-00013, Sch-23863, Sch-23863, Sch-57790, Sch-63390, scillarenin, scopolamine, scopolamine, scopolamine N-oxide, SCS technology, secalciferol, secnidazole, secobarbital, selegiline, selenomethionine, sematilide, semotiadil, seocalcitol, sepimostat, seratrodast, sertaconazole, sertaconazole, sertindole, sertindole, sertraline, sertraline, sestamibi, setastine, setastine, sevelamer, sevelamer, sevoflurane, sevoflurane, SG-210, sibutramine, siccanin, sildenafil, silodosin, silprostone, silver lactate, silver picrate, silver sulfadiazine, simetride, simfibrate, simvastatin, sincalide, sintropium bromide, sisomicin, sitafloxacin, sitamaquine, sitaxsentan, sivelestat, SJA-6017, SL-65-1498, SLV-306, SLV-308, Sml53 lexidronam, S-methylmethionine, SMP-300, SN-38, SNAP-7941, SOA-132, soblidotin, sobrerol, sobuzoxane, sodium arsanilate, sodium arsphenamine, sodium chloride, sodium dibunate, sodium folate, sodium formaldehydesulfoxylate, sodium hyaluronate, sodium iodomethamate, sodium nitrite, sodium nitroprusside, sodium oxybate, sodium phenol-sulfonate, sodium phenylbutyrate, sodium phosphate, sodium prasterone sulfate, sodium propionate, sodium salicylate, sodium tradecyl sulfate, sofalcone, solasulfone, solifenacin, sorbinicate, sorbitol, sorivudine, sotalol, soterenol, sozoioddic acid, spaglumic acid, sparfloxacin, sparteine, SPA-S-843, spasmolytol, SPD-754, spectinomycin, SPI-339, spiperone, spirapril, spirogermanium, spironolactone, SR-121463, SR-144190, SR-146131, SR-271425, SR-27897, SR-31747, SR-58611, SS732, SS-750, SSR-149415, SSR-180575, SSR-181507, SSR-591813, SST-101, SSY-726, ST-200, stachyfilin, stallimycin, stampidine, stannous, stannsoporfin, stanolone, stanozolol, staph aureus ther, STAT4 inhibitors, stavudine, stenbolone, stepronim, stibocaptate, stibophen, stilbamidine, stiripentol, streptodomase, streptomycin, streptonicozid, streptonigrin, streptozocin, strontium ranelate, strontium-89 chloride, succimer, succinimide, succinylcholine, succinylcholine, succinylsulfathiazole, succisulfone, suclofenide, sucralfate, sufentanil, sulbactam, sulbactam+ampicillin, sulbenicillin, sulbentine, sulbutiamine, sulconazole, suleptanate, sulesomab, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanole, sulfalene, sulfaloxic acid, sulfamerazine, sulfameter, sulfamethazine, sulfamethizole, sulfamethomidine, sulfamethoxazole, sulfamethoxypyrazine, sulfamethoxypyridazine, sulfametrole, sulfamidochrysoidine, sulfamoxole, sulfanilamide, sulfanilic acid, sulfanilylurea, sulfaperine, sulfaphenazole, sulfaproxyline, sulfapyrazine, sulfapyridine, sulfarside, sulfarsphenamine, sulfasalazine, sulfasomizole, sulfasymazine, sulfathiazole, sulfathiourea, sulfinalol, sulfinpyrazone, sulfiram, sulfisomidine, sulfisoxazole, sulfobromophthalein, sulfonethylmethane, sulfoniazide, sulfonic acid, sulfonmethane, sulforidazine, sulfoxone, sulindac, sulisatin, sulisobenzone, sulmarin, sulmazole, suloctidil, sulphan blue, sulpiride, sultamicillin, sulthiame, sultopride, sultosilic acid, sumanirole, sumatriptan, SUN-N8075, suplatast, suprofen, suramin, surfactant TA, suriclone, suxibuzone, SYM-1010, SYM-2081, SYM-2207, symclosene, Syn-1253, Syn-2190, Syn-2869, synephrine, syrosingopine, T-1095, T-1249, T-3912, T-588, T-67, T-82, TA-2005, TA-2005, TA-993, tabimorelin, tacalcitol, tacedinaline, tacrine, tacrolimus, tadalafil, tafenoquine, tafluposide, TAK-375, TAK-427, TAK-559, taka-diastase, talampanel, talampicillin, talaporfin, talastine, talbutal, talinolol, talipexole, talnetant, talniflumate, taltirelin, tamoxifen, tamsulosin, tandospirone, tannoform, taprostene, tariquidar, TAS-103, tasosartan, taurocholic acid, taurolidine, tazanolast, tazarotene, tazobactam, tazobactam+piperacillin, TBC-3711, TCH-346, tebipenem, teboroxime, tecadenoson, tecastemizole, Technetium $^{99}$Tc, teclothiazide, teclozan, tedisamil, teflurane, tegafur, tegafur+uracil, tegaserod, teicoplanin, telbivudine, telenzepine, telithromycin, telmesteine, telmisartan, telomerase inhibs, temazepam, temiverine, temocapril, temocillin, temoporfin, temozolomide, tenatoprazole, tenecteplase, tenidap, teniposide, tenofovir, tenofovir disoproxil, tenonitrozole, tenoxicam, tenuazonic acid, teprenone, terazosin, terbinafine, terbutaline, terconazole, terfenadine, terguride, terlipressin, terodiline, terofenamate, terpin, tertalolol, tert-pentyl alcohol, tesaglitazar, tesmilifene, testolactone, testosterone, tetrabamate, tetrabarbital, tetrabenazine, tetracaine, tetrachloroethylene, tetracine, tetracycline, tetrahydrozoline, tetrandrine, tetrantoin, tetrazepam, tetrofosmin, tetroxoprim, Tevenel®, tezacitabine, tezosentan, thalidomide, thenaldine, thenyldiamine, theobromine, theofibrate, theophylline, thiabendazole, thiacetazone, thiacymserine, thialbaibital, thiamine, thiamiprine, thiamphenicol, thiamylal, thiazesim, thiazinamium, thiazolinobutazone, thiazolsulfone, thibenzazoline, thiemalat, thiethylperazine, thimerfonate, thimerosal, thiobarbital, thiobutabaibital, thiocarbamizine, thiocarbarsone, thiocolchicine, thiocresol, thioctic acid, thioglycerol, thioguanine, thioimrag, thiopental, thiophosphoramide, thiopropazate, thioproperazine, thioridazine, thiosulfate, thiothixene, thiovir, thiphenamil, thiram, thonzylamine, thozalinone, thromboplastin, thurfyl nicotinate, thymectacin, thymol, thymopentin, thymyl N-isoamylcarbamate, thyropropic acid, thyroxine, tiadenol, tiagabine, tiamenidine, tianeptine, tiapride, tiaprofenic acid, tiaramide, tiazofurin, tibezonium, tibdone, ticarcillin, ticlopidine, ticrynafen, tiemonium, tigecycline, tigemonam, tigloidine, tilidine, tilisolol, tilmacoxib, tiludronic acid, timentin, timepidium, timiperone, timolol, timonacic, tin ethyl etiopurpurin, tinazoline, tinidazole, tinoridine, tiocarlide, tioclomarol, tioconazole, tiopronin, tiotropium, tioxolone, tipepidine, tipifarnib, tipranavir, tiquizium, tirapazamine, tiratricol, tirilazad, tirofiban, tiropramide, titanium sulfate, tiuxetan, tixocortol, tizanidine, TLK-199, TLK-286, TNF-β analogue, TNP-470, TO-186, tobramycin, tocainide, tocamphyl, tocladesine, tocoretinate, todralazine, tofenacin, tofimilast, tofisopam, tolazamid, tolazolin, tolbutamide, tolcapone, tolciclate, tolcyclamide, tolevamer, tolfenamic acid, tolindate, toliprolol, tolmetin, tolnaftate, tolonidine, tolonium, toloxatone, tolperisone, tolpropamine, tolrestat, tolserine, tolterodine, tolvaptan, tolycaine, topiramate, topoisomerase, topotecan, torasemide, torcetapib, torcitabine, toremifene, torsemide, tositumomab, tosulfloxacin, tramadol, tramazoline, trandolapril, tranexamic acid, tranilast, trans-retinoic acid, tranylcypromine, trapidil, trastuzumab, travoprost, traxanox, traxoprodil, trazodone, tremacamra, trenbolone, trengestone, treosulfan, trepibutone, treprostinol, tretinoin, tretoquinol, TRH, TRI-50b, triacetin, triamcinolone, triamcinolone, triamcinolone, triamcinolone acetonide, triamterene, triapine, triaziquone, triazolam, tribenoside, tribromophenate, trichlorfon, trichlormethiazide, trichlormethine, trichloroethylene, triclobisonium, triclocarban, triclofenol piperazine, triclofos, triclosan, tricromyl, tridihexethyl iodide, trientine, triethanolamine, triethylenemelamine, trifluoperazine, trifluperidol, triflupromazine, trifluridine, triflusal, triflutate, trihexyphenidyl, trimazosin, trimebutine, trimecaine, trimeprazine, trimetazidine, trimethadione, trimethaphan, trimethobenzamide, trimethoprim, trimetozine, trimetrexate, trimipramine, trimoprostil, triolstane, trioxsalen, tripamide, triparanol, tripelennamine, triprolidine, triptorelin, tritiozine, tritoqualine, TRK-530, TRK-820, troclosene, trofosfamide, troglitazone, troleandomycin, trolnitrate, tromantadine, trometamol, trometamol, tromethamine, tromethamine, tropacine, tropesin, tropicamide, tropine, tropisetron, trospectomycin, trospium, trovafloxacin, troxacitabine, troxerutin, troxipide, trypan red, tryparsamide, tryptophan, TSH, TSN-09, TU-2100, tuaminoheptane, tubercidin, tubocurarine chloride, tulobuterol, TV-3326, TY-11223, TY-12533, TYB-3215, tybamate, tyloxapol, tymazoline, tyramine, tyropanoate, ubenimex, ufenamate, undecylenic acid, unoprostone, UR-8880, uracil mustard, uralyt-U, urapidil, urea, uredepa, urethan, uridine 5′-triphosphate, urinastatin, ursodeoxycholic acid, ursodiol, ushercell, uzarin, vaccine, Diphtheria Vaccine, Polyvalent Vaccine, valacyclovir, valdecoxib, valdetamide, valethamate, valganciclovir, valnoctamide, valomaciclovir, valproate, valproic acid, valpromide, valrocemide, valrubicin, valsartan, valspodar, vardenafil, varespladib, varicella virus, vatanidipine, VEA, vecuronium, velnacrine, venlafaxine, veralipride, verapamil, verteporfin, vesnarinone, vetrabutine, VF-233, VI-0134, vidarabine, vigabatrin, vilazodone, viloxazine, viminol, vinbarbital, vinblastine, vinbumine, vincamine, vinconate, vincristine, vindesine, vinflunine, vinorelbine, vinpocetine, vinyl ether, vinylbital, viquidil, viridin, visnadine, vitamin A, vitamin B12, vitamin C, vitamin D2, vitamin D3, vitamin K5, prenatal vitamins, VLA-4 antagonists, VNP-4010M, voglibose, voriconazole, vorozole, VUF-K-8788, warfarin, WF-10, WMC-79, wound healing matrix, WP-170, xaliproden, xamoterol, xanomeline, xanthinol niacinate, xemilofiban, xenbucin, xibenolol, xibomol, ximelagatran, ximoprofen, xipamide, xorphanol, XR-5118, XR-5944, xylometazoline, xylose, YH-1885, YM-511, YM-598, yohimbine, YT-146, Z-321, Z-335, zafirlukast, zalcitabine, zaldaride, zaleplon, zaltoprofen, zanamivir, zanapezil, zatebradine, ZD-0473, ZD-0947, ZD-6126, ZD-9331, zebularine, zelandopam, zenarestat, ziconotide, zidovudine, zileuton, zimeldine, zinc acetate, zinc acexamate, zinc ibuprofenate, zinc p-phenolsulfonate, zinc salicylate, zinostatin, zinostatin stimalamer, zipeprol, ziprasidone, zofenopril, zofenpril+HCTZ, zoledronic acid, zolimidine, zolmitriptan, zdpidem, zomepirac, zonampanel, zoniporide, zonisamide, zopiclone, zopolrestat, zorubicin, zosuquidar, zotepine, ZP-123, Z-tamoxifen, zuclopenthixol, α1-antitrypsin, α-bisabolol, α-chloralose, α-ethylbenzyl alcohol, α-glucose-1-phosphate, α-phenylbutyramide, α-santonin, α-terpineol, α-tocopherol, β-alethine, β-benzalbutyramide, β-carotene, β-eucaine, β-propiolactone, β-sitosterol, γ-aminobutyric acid, γ-hydroxybutyrate, γ-linolenic acid, δ-aminolevulinic acid, ε-acetamidocaproic, and ε-aminocaproic acid. See also U.S. Pat. No. 7,927,613, which is incorporated herein by reference in its entirety. Other pharmaceutically acceptable coformers include those delineated in the "Generally Regarded as Safe" ("GRAS") and/or the US FDA "Everything Added to Food in the United States" ("EAFUS") lists.

In some embodiments, at least one of the one or more pharmaceutically acceptable coformers is niclosamide or a pharmaceutically acceptable salt or hydrate thereof; or a niclosamide analog, or a pharmaceutically acceptable salt or hydrate thereof. In some of these embodiments, at least one of the one or more pharmaceutically acceptable coformers can be a compound having any one of formulas (I), (XVIII)-(XXV), and XXVII, e.g., formula XXIV or XXV; or any one of the compounds delineated above. In certain of these embodiments, at least one of the one or more pharmaceutically acceptable coformers can be a niclosamide analogue having any one of formulas (I), (XVIII)-(XXV), and XXVII, e.g., formula XXIV or XXV; or XXVI; or any one of the compounds specifically delineated above. In certain of these embodiments, the chemical entity can be a niclosamide or a pharmaceutically acceptable salt or hydrate thereof (e.g., niclosamide).

Non-limiting Combinations

In some embodiments, the cocrystal includes (i) niclosamide or a niclosamide analog; and (ii) a pharmaceutically acceptable salt and/or hydrate of niclosamide; or a pharmaceutically acceptable salt and/or hydrate of a niclosamide analog.

In some embodiments, the cocrystal includes (i) niclosamide; and (ii) a pharmaceutically acceptable salt and/or hydrate of niclosamide; or a pharmaceutically acceptable salt and/or hydrate of niclosamide of a niclosamide analog.

In some embodiments, the cocrystal includes (i) niclosamide or a niclosamide analog; and (ii) a second API.

In some embodiments, the cocrystal includes (i) a pharmaceutically acceptable salt and/or hydrate of niclosamide; or a pharmaceutically acceptable salt and/or hydrate of niclosamide of a niclosamide analog; and (ii) a second API.

In some embodiments, the cocrystal includes (i) niclosamide; and (ii) a second API.

In some embodiments, the cocrystal includes (i) a pharmaceutically acceptable salt and/or hydrate of niclosamide; or a pharmaceutically acceptable salt and/or hydrate of niclosamide of a niclosamide analog; and (ii) an amino acid (e.g., proline, e.g., D-proline, or L-proline, or racemic proline).

In some embodiments, the cocrystal includes (i) niclosamide; and (ii) an amino acid (e.g., proline, e.g., D-proline, or L-proline, or racemic proline).

In some embodiments, the cocrystal includes (i) a pharmaceutically acceptable salt and/or hydrate of niclosamide; or a pharmaceutically acceptable salt and/or hydrate of niclosamide of a niclosamide analog; and (ii) a 5-10 (e.g., 5-9, 5-6, or 5) membered heteroaryl, e.g., a nitrogen-containing heteroaryl, e.g., imidazole.

In some embodiments, the cocrystal includes (i) niclosamide; and (ii) a 5-10 (e.g., 5-9, 5-6, or 5) membered heteroaryl, e.g., a nitrogen-containing heteroaryl, e.g., imidazole.

For examples, see Sanphui, P. *Cryst. Growth Des.* 2012, 12, 4588; Imramovský, A. *Crystals* 2012, 2, 349-361; and Grifasi, F. *Cryst. Growth Des.* 2015, 15, 4588.

Properties

In some embodiments, the resulting co-crystals confer enhanced and/or new and beneficial properties to the chemical entity (and/or to one or more of the conformers, e.g., when a conformer is a second API) as compared to the chemical entity in a free form (including free acids, free bases, and zwitter ions, hydrates, solvates, etc.), or an acid or base salt thereof particularly with respect to, e.g., solubility, dissolution, bioavailability, stability, Cmax, Tmax, permeability processability, therapeutic plasma concentration, hygroscopicity, localized concentration, crystallization of amorphous compounds, decrease in form diversity (including polymorphism and crystal habit), change in morphology or crystal habit.

In some embodiments, the cocrystals have an oral bioavailability (F) of less than about 50%, or less than about 40%, or less than about 30%, or less than about 20%, or less than about 10%, or less than about 5%, or less than about 2%, or less than about 1%. In certain embodiments, the chemical entities described herein have an oral bioavailability (F) of less than about 20%, e.g., less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, less than about 1%, or less than about 0.5%.

In some embodiments, the cocrystals have a relatively low aqueous solubility. Low aqueous solubility refers to a compound having a solubility in water which is less than or equal to 10 mg/mL, when measured at 20° C. In certain embodiments, the chemical entities described herein have aqueous solubility of less than or equal to 900, 800, 700, 600, 500, 400, 300, 200 150 100, 90, 80, 70, 60, 50, 40, 30.20 micrograms/mL, or further 10, 5 or 1 micrograms/mL, or further 900, 800, 700, 600, 500, 400, 300, 200 150, 100 90, 80, 70, 60, 50, 40, 30, 20, or 10 ng/mL, or less than 10 ng/mL when measured at 20° C.

In some embodiments, the cocrystals have a relatively low drug permeability.

Pharmaceutical Compositions and Administration

General

A chemical entity (e.g., a compound exhibiting activity as a mitochondrial uncoupling agent or a pharmaceutically acceptable salt and/or hydrate and/or cocrystal thereof; e.g., a compound, such as niclosamide or a pharmaceutically acceptable salt and/or hydrate and/or cocrystal thereof; e.g., a compound, such as a niclosamide analog, or a pharmaceutically acceptable salt and/or hydrate and/or cocrystal thereof) is administered to a subject in need thereof by any route which makes the compound bioavailable (e.g., locally bioavailable).

In some embodiments, a chemical entity (e.g., a compound exhibiting activity as a mitochondrial uncoupling agent or a pharmaceutically acceptable salt and/or hydrate and/or cocrystal thereof; e.g., a compound, such as niclosamide or a pharmaceutically acceptable salt and/or hydrate and/or cocrystal thereof; e.g., a compound, such as a niclosamide analog, or a pharmaceutically acceptable salt and/or hydrate and/or cocrystal thereof) is administered as a pharmaceutical composition that includes the chemical entity and one or more pharmaceutically acceptable excipients, and optionally one or more other therapeutic agents as described herein.

In some embodiments, the chemical entities can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%-100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see *Remington: The Science and Practice of Pharmacy*, 22$^{nd}$ Edition (Pharmaceutical Press, London, U K. 2012).

In some embodiments, the chemical entities described herein or a pharmaceutical composition thereof can be administered to subject in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumor, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal.

Local Administration

In some embodiments, the chemical entities described herein or a pharmaceutical composition thereof are suitable for local administration, e.g., local administration by way of topically administering the chemical entity or composition thereof at a particular treatment site, (e.g., the digestive tract, the gastrointestinal ("GI") tract, eye, joint, or skin) so as to provide local administration of the chemical entity to the area in need of treatment (e.g., oral cavity; GI tract, e.g., the colon; eye; skin; or joint). In certain embodiments, minimal systemic exposure of the chemical entity occurs during said local administration. Examples of such compositions include, without limitation, compositions for rectal administration, oral administration, dermal administration, or implant. In certain embodiments, compositions are for other than oral administration.

In some embodiments, the chemical entities described herein or a pharmaceutical composition thereof are suitable for local administration to the GI tract. In certain embodiments, upon administration, the local concentration of the chemical entity in the GI tract is higher (e.g., from about 2 times higher to about 50 times higher, from about 5 times higher to about 50 times higher; from about 5 times higher to about 25 times higher; from about 5 times higher to about 15 times higher; e.g., about 50 times higher, about 25 time higher, about 20 times higher, about 15 times higher, about 10 times higher, about 5 times higher, e.g., at least about 10 times higher) than the concentration of the chemical entity in the plasma compartment. In certain of these embodiments, the chemical entity in the plasma compartment is subject to first pass metabolism.

In some embodiments, the chemical entities described herein or a pharmaceutical composition thereof are suitable for local administration to one or more specific locations within the digestive or GI tract. For example, at least some of the chemical entity is present in the upper GI tract (e.g., stomach); or at least some of the agent is present in the lower GI tract (e.g., the large intestine, e.g., the colon, e.g., the ascending colon and/or transverse colon and/or distal colon; or the small bowel). As a further example, at least some of the chemical entity is present in the ascending colon and/or the transverse colon and/or the distal colon and/or the small bowel and/or the stomach. Methods of said local administration can include, without limitation, rectal administration and/or oral administration.

In certain embodiments, the chemical entities described herein or a pharmaceutical composition thereof are suitable for local, topical administration to the digestive or GI tract, e.g., rectal administration. Rectal compositions include, without limitation, enemas, rectal gels, rectal foams, rectal aerosols, suppositories, jelly suppositories, and enemas (e.g., retention enemas).

Pharmacologically acceptable excipients usable in the rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methyloxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In certain embodiments, suppositories can be prepared by mixing the chemical entities described herein with suitable non-irritating excipients or carriers such as cocoa butter, polyethylene glycol or a suppository wax which are solid at ambient temperature but liquid at body temperature and therefore melt in the rectum and release the active compound. In other embodiments, compositions for rectal administration are in the form of an enema.

Enema Formulations

In some embodiments, enema formulations containing the chemical entities described herein are provided in "ready-to-use" form.

In some embodiments, enema formulations containing the chemical entities described herein are provided in one or more kits or packs. In certain embodiments, the kit or pack includes two or more separately contained/packaged components, e.g. two components, which when mixed together, provide the desired formulation (e.g., as a suspension). In certain of these embodiments, the two component system includes a first component and a second component, in which: (i) the first component (e.g., contained in a sachet) includes the chemical entity (as described anywhere herein) and optionally one or more pharmaceutically acceptable excipients (e.g., together formulated as a solid preparation, e.g., together formulated as a wet granulated solid preparation); and (ii) the second component (e.g., contained in a vial or bottle) includes one or more liquids and optionally one or more other pharmaceutically acceptable excipients together forming a liquid carrier. Prior to use (e.g., immediately prior to use), the contents of (i) and (ii) are combined to form the desired enema formulation, e.g., as a suspension. In other embodiments, each of component (i) and (ii) is provided in its own separate kit or pack.

In some embodiments, each of the one or more liquids is water, or a physiologically acceptable solvent, or a mixture of water and one or more physiologically acceptable solvents. Typical such solvents include, without limitation, glycerol, ethylene glycol, propylene glycol, polyethylene glycol and polypropylene glycol. In certain embodiments, each of the one or more liquids is water. In other embodiments, each of the one or more liquids is an oil, e.g. natural and/or synthetic oils that are commonly used in pharmaceutical preparations.

Further pharmaceutical excipients and carriers that may be used in the pharmaceutical products herein described are listed in various handbooks (e.g. D. E. Bugay and W. P. Findlay (Eds) Pharmaceutical excipients (Marcel Dekker, New York, 1999), E-M Hoepfner, A. Reng and P. C. Schmidt (Eds) Fiedler Encyclopedia of Excipients for Pharmaceuticals, Cosmetics and Related Areas (Edition Cantor, Munich, 2002) and H. P. Fielder (Ed) Lexikon der Hilfsstoffe für Pharmazie, Kosmetik and angrenzende Gebiete (Edition Cantor Aulendorf, 1989)).

In some embodiments, each of the one or more pharmaceutically acceptable excipients can be independently selected from thickeners, viscosity enhancing agents, bulking agents, mucoadhesive agents, penetration enhancers, buffers, preservatives, diluents, binders, lubricants, glidants, disintegrants, fillers, solubilizing agents, pH modifying agents, preservatives, stabilizing agents, anti-oxidants, wetting or emulsifying agents, suspending agents, pigments, colorants, isotonic agents, chelating agents, emulsifiers, and diagnostic agents.

In certain embodiments, each of the one or more pharmaceutically acceptable excipients can be independently selected from thickeners, viscosity enhancing agents, mucoadhesive agents, buffers, preservatives, diluents, binders, lubricants, glidants, disintegrants, and fillers.

In certain embodiments, each of the one or more pharmaceutically acceptable excipients can be independently selected from thickeners, viscosity enhancing agents, bulking agents, mucoadhesive agents, buffers, preservatives, and fillers.

In certain embodiments, each of the one or more pharmaceutically acceptable excipients can be independently selected from diluents, binders, lubricants, glidants, and disintegrants.

Examples of thickeners, viscosity enhancing agents, and mucoadhesive agents include without limitation: gums, e.g. xanthan gum, guar gum, locust bean gum, tragacanth gums, karaya gum, ghatti gum, cholla gum, psyllium seed gum and gum arabic; poly(carboxylic acid-containing) based polymers, such as poly (acrylic, maleic, itaconic, citraconic, hydroxyethyl methacrylic or methacrylic) acid which have strong hydrogen-bonding groups, or derivatives thereof such as salts and esters; cellulose derivatives, such as methyl cellulose, ethyl cellulose, methylethyl cellulose, hydroxymethyl cellulose, hydroxyethyl cellulose, hydroxypropyl cellulose, hydroxyethyl ethyl cellulose, carboxymethyl cellulose, hydroxypropylmethyl cellulose or cellulose esters or ethers or derivatives or salts thereof; clays such as manomorillonite clays, e.g. Veegun, attapulgite clay; polysaccharides such as dextran, pectin, amylopectin, agar, mannan or polygalactonic acid or starches such as hydroxypropyl starch or carboxymethyl starch; polypeptides such as casein, gluten, gelatin, fibrin glue; chitosan, e.g. lactate or glutamate or carboxymethyl chitin; glycosaminoglycans such as hyaluronic acid; metals or water soluble salts of alginic acid such as sodium alginate or magnesium alginate; schleroglucan; adhesives containing bismuth oxide or aluminium oxide; atherocollagen; polyvinyl polymers such as carboxyvinyl polymers; polyvinylpyrrolidone (povidone); polyvinyl alcohol; polyvinyl acetates, polyvinylmethyl ethers, polyvinyl chlorides, polyvinylidenes, and/or the like; polycarboxylated vinyl polymers such as polyacrylic acid as mentioned above; polysiloxanes; polyethers; polyethylene oxides and glycols; polyalkoxys and polyacrylamides and derivatives and salts thereof. Preferred examples can include cellulose derivatives, such as methyl cellulose, ethyl cellulose, methylethyl cellulose, hydroxymethyl cellulose, hydroxyethyl cellulose, hydroxypropyl cellulose, hydroxyethyl ethyl cellulose, carboxymethyl cellulose, hydroxypropylmethyl cellulose or cellulose esters or ethers or derivatives or salts thereof (e.g., methyl cellulose); and polyvinyl polymers such as polyvinylpyrrolidone (povidone).

Examples of preservatives include without limitation: benzalkonium chloride, benzoxonium chloride, benzethonium chloride, cetrimide, sepazonium chloride, cetylpyridinium chloride, domiphen bromide (Bradosol®), thiomersal, phenylmercuric nitrate, phenylmercuric acetate, phenylmercuric borate, methylparaben, propylparaben, chlorobutanol, benzyl alcohol, phenyl ethyl alcohol, chlorohexidine, polyhexamethylene biguanide, sodium perborate, imidazolidinyl urea, sorbic acid, Purite®), Polyquart®), and sodium perborate tetrahydrate and the like.

In certain embodiments, the preservative is a paraben, or a pharmaceutically acceptable salt thereof. In some embodiments, the paraben is an alkyl substituted 4-hydroxybenzoate, or a pharmaceutically acceptable salt or ester thereof. In certain embodiments, the alkyl is a C1-C4 alkyl. In certain embodiments, the preservative is methyl 4-hydroxybenzoate (methylparaben), or a pharmaceutically acceptable salt or ester thereof, propyl 4-hydroxybenzoate (propylparaben), or a pharmaceutically acceptable salt or ester thereof, or a combination thereof.

Examples of buffers include without limitation: phosphate buffer system (sodium dihydrogen phospahate dehydrate, disodium phosphate dodecahydrate, bibasic sodium phosphate, anhydrous monobasic sodium phosphate), bicarbonate buffer system, and bisulfate buffer system.

Examples of disintegrants include, without limitation: carmellose calcium, low substituted hydroxypropyl cellulose (L-HPC), carmellose, croscarmellose sodium, partially pregelatinized starch, dry starch, carboxymethyl starch sodium, crospovidone, polysorbate 80 (polyoxyethylenesorbitan oleate), starch, sodium starch glycolate, hydroxypropyl cellulose pregelatinized starch, clays, cellulose, alginine, gums or cross linked polymers, such as cross-linked PVP (Polyplasdone XL from GAP Chemical Corp). In certain embodiments, the disintegrant is crospovidone.

Examples of glidants and lubricants (aggregation inhibitors) include without limitation: talc, magnesium stearate, calcium stearate, colloidal silica, stearic acid, aqueous silicon dioxide, synthetic magnesium silicate, fine granulated silicon oxide, starch, sodium laurylsulfate, boric acid, magnesium oxide, waxes, hydrogenated oil, polyethylene glycol, sodium benzoate, stearic acid glycerol behenate, polyethylene glycol, and mineral oil. In certain embodiments, the glidant/lubricant is magnesium stearate, talc, and/or colloidal silica; e.g., magnesium stearate and/or talc.

Examples of diluents, also referred to as "fillers" or "bulking agents" include without limitation: di calcium phosphate dihydrate, calcium sulfate, lactose (e.g., lactose monohydrate), sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar. In certain embodiments, the diluent is lactose (e.g., lactose monohydrate).

Examples of binders include without limitation: starch, pregelatinized starch, gelatin, sugars (including sucrose, glucose, dxtrose, lactose and sorbitol), polyethylene glycol, waxes, natural and synthetic gums such as acacia tragacanth, sodium alginate cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone (povidone). In certain embodiments, the binder is polyvinylpyrrolidone (povidone).

In some embodiments, enema formulations containing the chemical entities described herein include water and one or more (e.g., all) of the following excipients:

One or more (e.g., one, two, or three) thickeners, viscosity enhancing agents, binders, and/or mucoadhesive agents (e.g., cellulose or cellulose esters or ethers or derivatives or salts thereof (e.g., methyl cellulose); and polyvinyl polymers such as polyvinylpyrrolidone (povidone);

One or more (e.g., one or two; e.g., two) preservatives, such as a paraben, e.g., methyl 4-hydroxybenzoate (methylparaben), or a pharmaceutically acceptable salt or ester thereof, propyl 4-hydroxybenzoate (propylparaben), or a pharmaceutically acceptable salt or ester thereof, or a combination thereof;

One or more (e.g., one or two; e.g., two) buffers, such as phosphate buffer system (e.g., sodium dihydrogen phospahate dehydrate, disodium phosphate dodecahydrate);

One or more (e.g., one or two, e.g., two) glidants and/or lubricants, such as magnesium stearate and/or talc;

One or more (e.g., one or two; e.g., one) disintegrants, such as crospovidone; and One or more (e.g., one or two; e.g., one) diluents, such as lactose (e.g., lactose monohydrate).

In certain of these embodiments, the chemical entity is niclosamide, or a pharmaceutically acceptable salt and/or hydrate and/or cocrystal thereof; e.g., niclosamide.

In certain embodiments, enema formulations containing the chemical entities described herein include water, methyl cellulose, povidone, methylparaben, propylparaben, sodium dihydrogen phospahate dehydrate, disodium phosphate dodecahydrate, crospovidone, lactose monohydrate, magnesium stearate, and talc. In certain of these embodiments, the chemical entity is niclosamide, or a pharmaceutically acceptable salt and/or hydrate and/or cocrystal thereof; e.g., niclosamide.

In certain embodiments, enema formulations containing the chemical entities described herein are provided in one or more kits or packs. In certain embodiments, the kit or pack includes two separately contained/packaged components, which when mixed together, provide the desired formulation (e.g., as a suspension). In certain of these embodiments, the two component system includes a first component and a second component, in which: (i) the first component (e.g., contained in a sachet) includes the chemical entity (as described anywhere herein) and one or more pharmaceutically acceptable excipients (e.g., together formulated as a solid preparation, e.g., together formulated as a wet granulated solid preparation); and (ii) the second component (e.g., contained in a vial or bottle) includes one or more liquids and one or more one or more other pharmaceutically acceptable excipients together forming a liquid carrier. In other embodiments, each of component (i) and (ii) is provided in its own separate kit or pack. In certain of these embodiments, component (i) includes the chemical entity (e.g., niclosamide, or a pharmaceutically acceptable salt and/or hydrate and/or cocrystal thereof; e.g., niclosamide) and one or more (e.g., all) of the following excipients:

(a) One or more (e.g., one) binders (e.g., a polyvinyl polymer, such as polyvinylpyrrolidone (povidone));

(b) One or more (e.g., one or two, e.g., two) glidants and/or lubricants, such as magnesium stearate and/or talc;

(c) One or more (e.g., one or two; e.g., one) disintegrants, such as crospovidone; and (d) One or more (e.g., one or two; e.g., one) diluents, such as lactose (e.g., lactose monohydrate).

In certain embodiments, component (i) includes from about 40 weight percent to about 80 weight percent (e.g., from about 50 weight percent to about 70 weight percent, from about 55 weight percent to about 70 weight percent; from about 60 weight percent to about 65 weight percent;

e.g., about 62.1 weight percent) of the chemical entity (e.g., niclosamide, or a pharmaceutically acceptable salt and/or hydrate and/or cocrystal thereof; e.g., niclosamide).

In certain embodiments, component (i) includes from about 0.5 weight percent to about 5 weight percent (e.g., from about 1.5 weight percent to about 4.5 weight percent, from about 2 weight percent to about 3.5 weight percent; e.g., about 2.76 weight percent) of the binder (e.g., povidone).

In certain embodiments, component (i) includes from about 0.5 weight percent to about 5 weight percent (e.g., from about 0.5 weight percent to about 3 weight percent, from about 1 weight percent to about 3 weight percent; about 2 weight percent e.g., about 1.9 weight percent) of the disintegrant (e.g., crospovidone).

In certain embodiments, component (i) includes from about 10 weight percent to about 50 weight percent (e.g., from about 20 weight percent to about 40 weight percent, from about 25 weight percent to about 35 weight percent; e.g., about 31.03 weight percent) of the diluent (e.g., lactose, e.g., lactose monohydrate).

In certain embodiments, component (i) includes from about 0.05 weight percent to about 5 weight percent (e.g., from about 0.05 weight percent to about 3 weight percent) of the glidants and/or lubricants.

In certain embodiments (e.g., when component (i) includes one or more lubricants, such as magnesium stearate), component (i) includes from about 0.05 weight percent to about 1 weight percent (e.g., from about 0.05 weight percent to about 1 weight percent; from about 0.1 weight percent to about 1 weight percent; from about 0.1 weight percent to about 0.5 weight percent; e.g., about 0.27 weight percent) of the lubricant (e.g., magnesium stearate).

In certain embodiments (when component (i) includes one or more lubricants, such as talc), component (i) includes from about 0.5 weight percent to about 5 weight percent (e.g., from about 0.5 weight percent to about 3 weight percent, from about 1 weight percent to about 3 weight percent; from about 1.5 weight percent to about 2.5 weight percent; from about 1.8 weight percent to about 2.2 weight percent; about 1.93 weight percent) of the lubricant (e.g., talc).

In certain of these embodiments, each of (a), (b), (c), and (d) above is present.

In certain embodiments, component (i) includes the ingredients and amounts as shown in Table 7.

TABLE 7

| Ingredient | Weight Percent |
| --- | --- |
| niclosamide | 40 weight percent to about 80 weight percent (e.g., from about 50 weight percent to about 70 weight percent, from about 55 weight percent to about 70 weight percent; from about 60 weight percent to about 65 weight percent; e.g., about 62.1 weight percent) |
| Crospovidone (Kollidon CL) | 0.5 weight percent to about 5 weight percent (e.g., from about 0.5 weight percent to about 3 weight percent, from about 1 weight percent to about 3 weight percent; about 1.93 weight percent |
| lactose monohydrate (Pharmatose 200M) | about 10 weight percent to about 50 weight percent (e.g., from about 20 weight percent to about 40 weight percent, from about 25 weight percent to about 35 weight percent; e.g., about 31.03 weight percent |
| Povidone (Kollidon K30) | about 0.5 weight percent to about 5 weight percent (e.g., from about 1.5 weight percent to about 4.5 weight percent, from about 2 weight percent to about 3.5 weight percent; e.g., about 2.76 weight percent |
| talc | 0.5 weight percent to about 5 weight percent (e.g., from about 0.5 weight percent to about 3 weight percent, from about 1 weight percent to about 3 weight percent; from about 1.5 weight percent to about 2.5 weight percent; from about 1.8 weight percent to about 2.2 weight percent; e.g., about 1.93 weight percent |
| Magnesium stearate | about 0.05 weight percent to about 1 weight percent (e.g., from about 0.05 weight percent to about 1 weight percent; from about 0.1 weight percent to about 1 weight percent; from about 0.1 weight percent to about 0.5 weight percent; e.g., about 0.27 weight percent |

In certain embodiments, component (i) includes the ingredients and amounts as shown in Table 8.

TABLE 8

| Ingredient | Weight Percent |
| --- | --- |
| niclosamide | About 62.1 weight percent) |
| Crospovidone (Kollidon CL) | About 1.93 weight percent |
| lactose monohydrate (Pharmatose 200M) | About 31.03 weight percent |
| Povidone (Kollidon K30) | About 2.76 weight percent |
| talc | About 1.93 weight percent |
| Magnesium stearate | About 0.27 weight percent |

In certain embodiments, component (i) is formulated as a wet granulated solid preparation. In certain of these embodiments an internal phase of ingredients (the chemical entity, disintegrant, and diluent) are combined and mixed in a high-shear granulator. A binder (e.g., povidone) is dissolved in water to form a granulating solution. This solution is added to the Inner Phase mixture resulting in the development of granules. While not wishing to be bound by theory, granule development is believed to be facilitated by the interaction of the polymeric binder with the materials of the internal phase. Once the granulation is formed and dried, an external phase (e.g., one or more lubricants—not an intrinsic component of the dried granulation), is added to the dry granulation. It is believed that lubrication of the granulation is important to the flowability of the granulation, in particular for packaging. See, e.g., Example 8.

In certain of the foregoing embodiments, component (ii) includes water and one or more (e.g., all) of the following excipients:

(a') One or more (e.g., one, two; e.g., two) thickeners, viscosity enhancing agents, binders, and/or mucoadhesive agents (e.g., cellulose or cellulose esters or ethers or derivatives or salts thereof (e.g., methyl cellulose); and polyvinyl polymers such as polyvinylpyrrolidone (povidone);

(b') One or more (e.g., one or two; e.g., two) preservatives, such as a paraben, e.g., methyl 4-hydroxybenzoate (methylparaben), or a pharmaceutically acceptable salt or ester thereof, propyl 4-hydroxybenzoate (propylparaben), or a pharmaceutically acceptable salt or ester thereof, or a combination thereof; and (c') One or more (e.g., one or two; e.g., two) buffers, such as phosphate buffer system (e.g., sodium dihydrogen phospahate dihydrate, disodium phosphate dodecahydrate);

In certain of the foregoing embodiments, component (ii) includes water and one or more (e.g., all) of the following excipients:

(a") a first thickener, viscosity enhancing agent, binder, and/or mucoadhesive agent (e.g., a cellulose or cellulose ester or ether or derivative or salt thereof (e.g., methyl cellulose));

(a'") a second thickener, viscosity enhancing agent, binder, and/or mucoadhesive agent (e.g., a polyvinyl polymer, such as polyvinylpyrrolidone (povidone));

(b") a first preservative, such as a paraben, e.g., propyl 4-hydroxybenzoate (propylparaben), or a pharmaceutically acceptable salt or ester thereof;

(b'") a second preservative, such as a paraben, e.g., methyl 4-hydroxybenzoate (methylparaben), or a pharmaceutically acceptable salt or ester thereof, (c") a first buffer, such as phosphate buffer system (e.g., disodium phosphate dodecahydrate);

(c'") a second buffer, such as phosphate buffer system (e.g., sodium dihydrogen phosphahate dehydrate), In certain embodiments, component (ii) includes from about 0.05 weight percent to about 5 weight percent (e.g., from about 0.05 weight percent to about 3 weight percent, from about 0.1 weight percent to about 3 weight percent; e.g., about 1.4 weight percent) of (a").

In certain embodiments, component (ii) includes from about 0.05 weight percent to about 5 weight percent (e.g., from about 0.05 weight percent to about 3 weight percent, from about 0.1 weight percent to about 2 weight percent; e.g., about 1.0 weight percent) of (a'").

In certain embodiments, component (ii) includes from about 0.005 weight percent to about 0.1 weight percent (e.g., from about 0.005 weight percent to about 0.05 weight percent; e.g., about 0.02 weight percent) of (b").

In certain embodiments, component (ii) includes from about 0.05 weight percent to about 1 weight percent (e.g., from about 0.05 weight percent to about 0.5 weight percent; e.g., about 0.20 weight percent) of (b'").

In certain embodiments, component (ii) includes from about 0.05 weight percent to about 1 weight percent (e.g., from about 0.05 weight percent to about 0.5 weight percent; e.g., about 0.15 weight percent) of (c").

In certain embodiments, component (ii) includes from about 0.005 weight percent to about 0.5 weight percent (e.g., from about 0.005 weight percent to about 0.3 weight percent; e.g., about 0.15 weight percent) of (c'").

In certain of these embodiments, each of (a")-(c'") is present.

In certain embodiments, component (ii) includes water (up to 100%) and the ingredients and amounts as shown in Table 9.

TABLE 9

| Ingredient | Weight Percent |
| --- | --- |
| methyl cellulose (Methocel A15C premium) | 0.05 weight percent to about 5 weight percent (e.g., from about 0.05 weight percent to about 3 weight percent, from about 0.1 weight percent to about 3 weight percent; e.g., about 1.4 weight percent |
| Povidone (Kollidon K30) | 0.05 weight percent to about 5 weight percent (e.g., from about 0.05 weight percent to about 3 weight percent, from about 0.1 weight percent to about 2 weight percent; e.g., about 1.0 weight percent |
| propyl 4-hydroxybenzoate | about 0.005 weight percent to about 0.1 weight percent (e.g., from about 0.005 weight percent to about 0.05 weight percent; e.g., about 0.02 weight percent) |
| methyl 4-hydroxybenzoate | about 0.05 weight percent to about 1 weight percent (e.g., from about 0.05 weight percent to about 0.5 weight percent; e.g., about 0.20 weight percent) |
| disodium phosphate dodecahydrate | about 0.05 weight percent to about 1 weight percent (e.g., from about 0.05 weight percent to about 0.5 weight percent; e.g., about 0.15 weight percent) |
| sodium dihydrogen phospahate dihydrate | about 0.005 weight percent to about 0.5 weight percent (e.g., from about 0.005 weight percent to about 0.3 weight percent; e.g., about 0.15 weight percent) |

In certain embodiments, component (ii) includes water (up to 100%) and the ingredients and amounts as shown in Table 10.

TABLE 10

| Ingredient | Weight Percent |
| --- | --- |
| methyl cellulose (Methocel A15C premium) | about 1.4 weight percent |
| Povidone (Kollidon K30) | about 1.0 weight percent |
| propyl 4-hydroxybenzoate | about 0.02 weight percent |
| methyl 4-hydroxybenzoate | about 0.20 weight percent |
| disodium phosphate dodecahydrate | about 0.15 weight percent |
| sodium dihydrogen phospahate dihydrate | about 0.15 weight percent |

Ready-to-use" enemas are generally be provided in a "single-use" sealed disposable container of plastic or glass. Those formed of a polymeric material preferably have sufficient flexibility for ease of use by an unassisted patient. Typical plastic containers can be made of polyethylene. These containers may comprise a tip for direct introduction into the rectum. Such containers may also comprise a tube between the container and the tip. The tip is preferably provided with a protective shield which is removed before use. Optionally the tip has a lubricant to improve patient compliance.

Figure 3A:
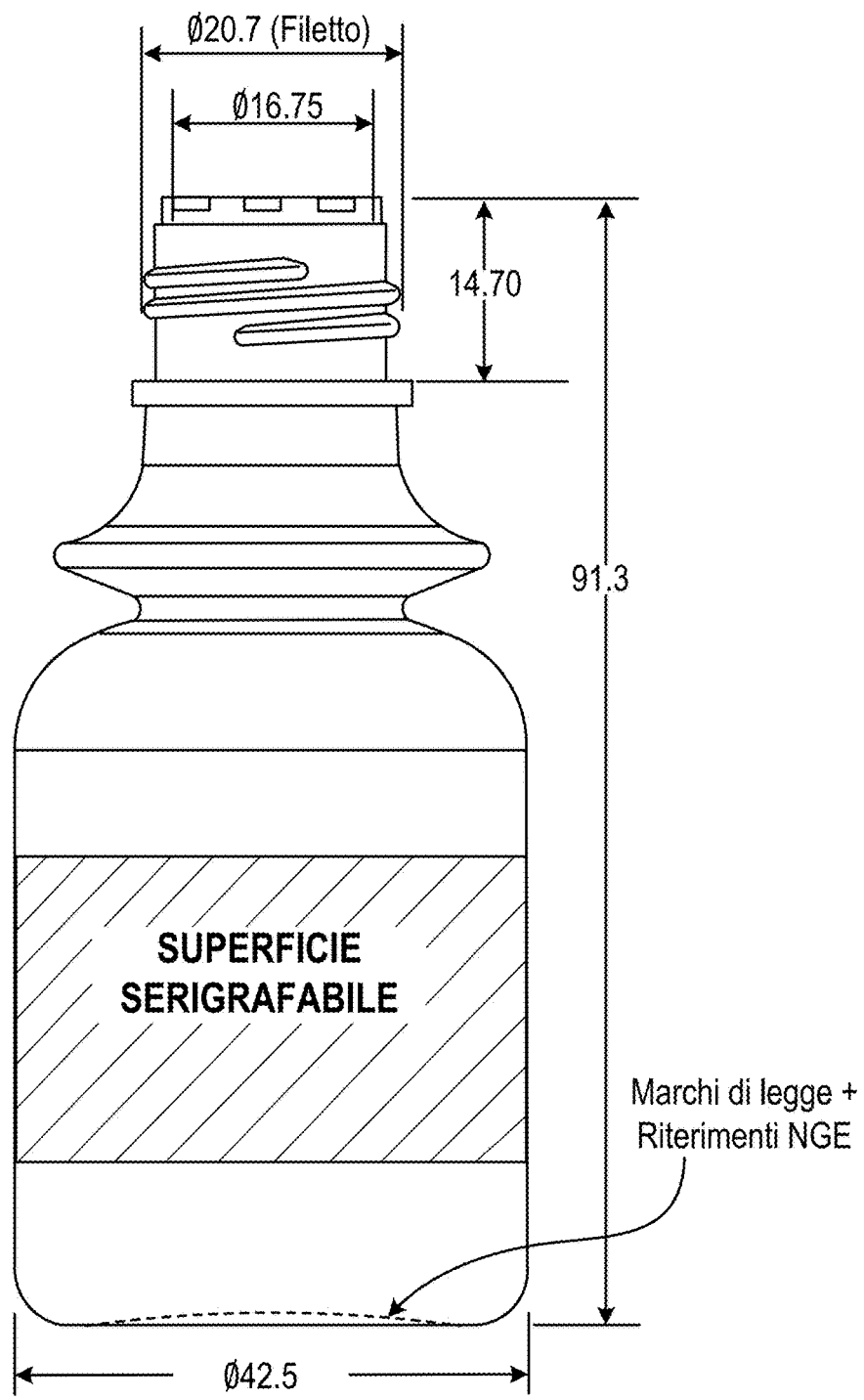
FIGS. 3A-3C show the components of a representative enema delivery device (FIG. 3A shows the bottle, FIG. 3B shows the breakable capsule, and FIG. 3C shows the rectal cannula (upper arrow) and single flow pack (lower arrow).
Figure 3B:
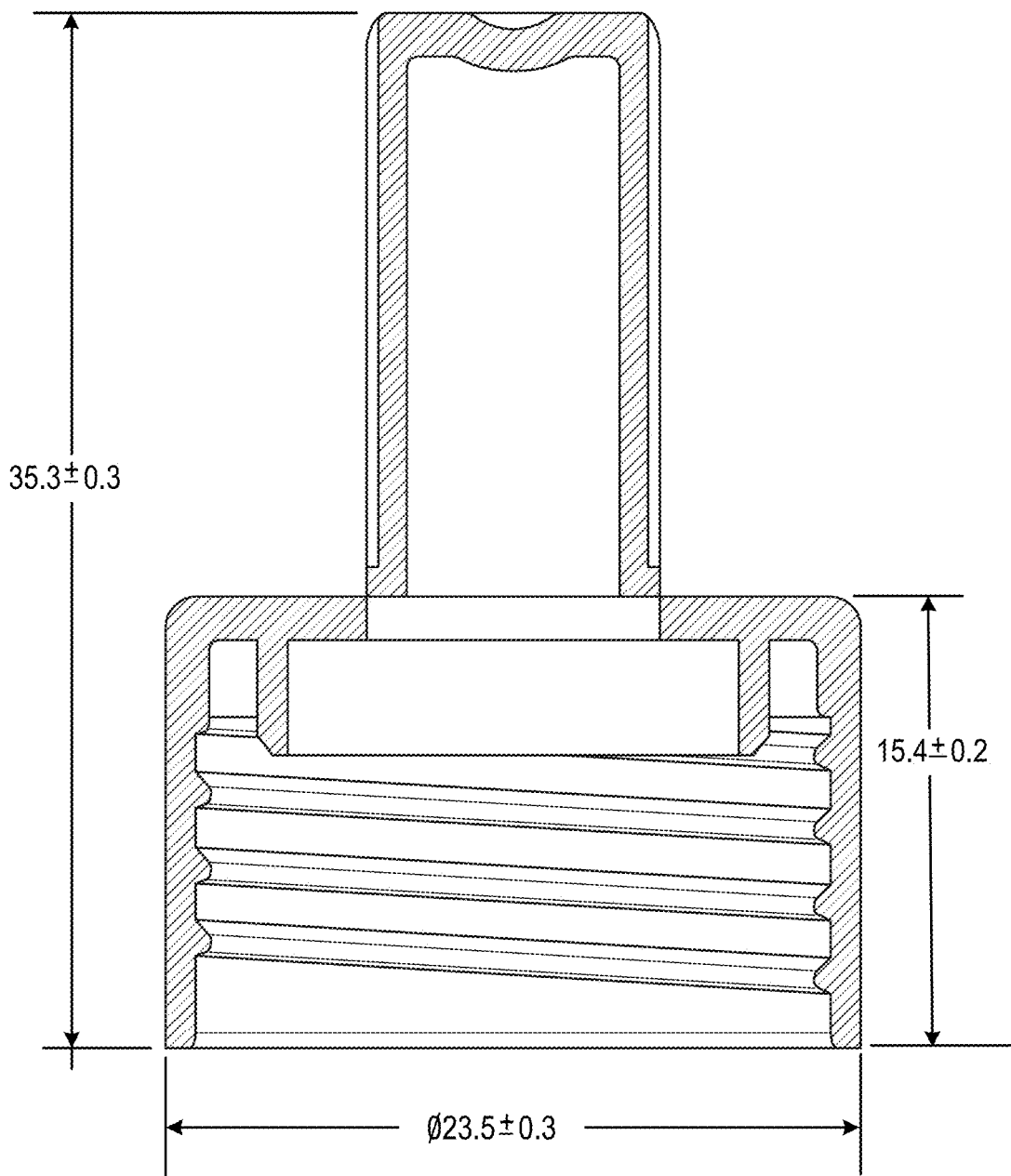
Figure 3C:
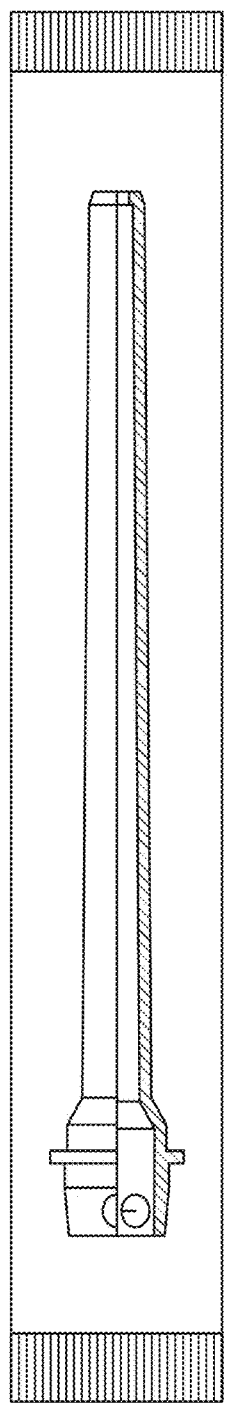

In some embodiments, the enema formulation (e.g., suspension) is poured into a bottle for delivery after it has been prepared in a separate container. In certain embodiments, the bottle is a plastic bottle (e.g., flexible to allow for delivery by squeezing the bottle), which can be a polyethylene bottle (e.g., white in color). In some embodiments, the bottle is a single chamber bottle, which contains the suspension or solution. In other embodiments, the bottle is a multichamber bottle, where each chamber contains a separate mixture or solution. In still other embodiments, the bottle can further include a tip or rectal cannula for direct introduction into the rectum. In some embodiments, the enema formulation can be delivered in the device shown in FIGS. 3A-3C, which includes a plastic bottle, a breakable capsule, and a rectal cannula and single flow pack.

Oral Delivery

In other embodiments, the chemical entities described herein or a pharmaceutical composition thereof are suitable for local delivery to the digestive or GI tract by way of oral administration (e.g., solid or liquid dosage forms).

Solid dosage forms for oral administration include capsules, tablets, pills, powders, and granules. In such solid dosage forms, the chemical entity is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

In one embodiment, the compositions will take the form of a unit dosage form such as a pill or tablet and thus the composition may contain, along with a chemical entity provided herein, a diluent such as lactose, sucrose, di calcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG'S, poloxamer 124 or triglycerides) is encapsulated in a capsule (gelatin or cellulose base capsule). Unit dosage forms in which one or more chemical entities provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid.

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

In certain embodiments, solid oral dosage forms can further include one or more components that chemically and/or structurally predispose the composition for delivery of the chemical entity to the stomach or the lower GI; e.g., the ascending colon and/or transverse colon and/or distal colon and/or small bowel. Exemplary formulation techniques are described in, e.g., Filipski, K. J., et al., *Current Topics in Medicinal Chemistry*, 2013, 13, 776-802, which is incorporated herein by reference in its entirety.

Examples include upper-GI targeting techniques, e.g., Accordion Pill (Intec Pharma), floating capsules, and materials capable of adhering to mucosal walls.

Other examples include lower-GI targeting techniques. For targeting various regions in the intestinal tract, several enteric/pH-responsive coatings and excipients are available. These materials are typically polymers that are designed to dissolve or erode at specific pH ranges, selected based upon the GI region of desired drug release. These materials also function to protect acid labile drugs from gastric fluid or limit exposure in cases where the active ingredient may be irritating to the upper GI (e.g., hydroxypropyl methylcellulose phthalate series, Coateric (polyvinyl acetate phthalate), cellulose acetate phthalate, hydroxypropyl methylcellulose acetate succinate, Eudragit series (methacrylic acid-methyl methacrylate copolymers), and Marcoat). Other techniques include dosage forms that respond to local flora in the GI tract, Pressure-controlled colon delivery capsule, and Pulsincap.

Liquid dosage forms for oral administration include pharmaceutically acceptable emulsions, microemulsions, solutions, suspensions, syrups and elixirs. In addition to the chemical entities described herein, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. In certain embodiments, the liquid dosage form is a mouthwash. In certain embodiments, such liquid oral dosage forms are useful for local and topical administration to the digestive or GI tract, e.g., digestive tract, e.g., oral cavity.

Other Forms of Delivery

In some embodiments, the chemical entities described herein or a pharmaceutical composition thereof are suitable for local and topical administration to the eye (e.g., eye drops). Ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

In some embodiments, the chemical entities described herein or a pharmaceutical composition thereof are suitable for local and topical administration to skin (e.g., ointments and creams). Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. As with other carriers or vehicles, an ointment base should be inert, stable, nonirritating and non-sensitizing.

Dosages

The dosages may be varied depending on the requirement of the patient, the severity of the condition being treating and the particular compound being employed. Determination of the proper dosage for a particular situation can be determined by one skilled in the medical arts. The total daily dosage may be divided and administered in portions throughout the day or by means providing continuous delivery.

In some embodiments, a chemical entity (e.g., a compound exhibiting activity as a mitochondrial uncoupling agent or a pharmaceutically acceptable salt and/or hydrate and/or cocrystal thereof; e.g., a compound, such as niclosamide or a pharmaceutically acceptable salt and/or hydrate and/or cocrystal thereof; e.g., a compound, such as a niclosamide analog, or a pharmaceutically acceptable salt and/or hydrate and/or cocrystal thereof) is administered is administered at a dosage of from about 0.01 mg/Kg to about 200 mg/Kg (e.g., from about 0.01 mg/Kg to about 150 mg/Kg; from about 0.01 mg/Kg to about 100 mg/Kg; from about 0.01 mg/Kg to about 50 mg/Kg; from about 0.01 mg/Kg to about 10 mg/Kg; from about 0.01 mg/Kg to about 5 mg/Kg; from about 0.1 mg/Kg to about 200 mg/Kg; from about 0.1 mg/Kg to about 150 mg/Kg; from about 0.1 mg/Kg to about 100 mg/Kg; from about 0.1 mg/Kg to about 50 mg/Kg; from about 0.1 mg/Kg to about 10 mg/Kg; from about 0.1 mg/Kg to about 5 mg/Kg).

In certain embodiments, the chemical entity is administered at a dosage of from about 15 mg/Kg to about 100 mg/Kg (e.g., from about 15 mg/Kg to about 90 mg/Kg, from about 20 mg/Kg to about 100 mg/Kg; from about 20 mg/Kg to about 90 mg/Kg; from about 20 mg/Kg to about 80 mg/Kg; from about 30 mg/Kg to about 90 mg/Kg; from about 30 mg/Kg to about 80 mg/Kg; from about 35 mg/Kg to about 75 mg/Kg; from about 10 mg/Kg to about 50 mg/Kg; from about 15 mg/Kg to about 45 mg/Kg; e.g., about 35 mg/Kg or about 75 mg/Kg). In other embodiments, the chemical entity is administered at a dosage of from about 0.1 mg/Kg to about 10 mg/Kg (e.g., from about 0.1 mg/Kg to about 5 mg/Kg; from about 1 mg/Kg to about 10 mg/Kg; from about 1 mg/Kg to about 5 mg/Kg).

In some embodiments, enema formulations include from about 0.5 mg to about 2500 mg (e.g., from about 0.5 mg to about 2000 mg, from about 0.5 mg to about 1000 mg, from about 0.5 mg to about 750 mg, from about 0.5 mg to about 600 mg, from about 0.5 mg to about 500 mg, from about 0.5 mg to about 400 mg, from about 0.5 mg to about 300 mg, from about 0.5 mg to about 200 mg; e.g., from about 5 mg to about 2500 mg, from about 5 mg to about 2000 mg, from about 5 mg to about 1000 mg; from about 5 mg to about 750 mg; from about 5 mg to about 600 mg; from about 5 mg to about 500 mg; from about 5 mg to about 400 mg; from about 5 mg to about 300 mg; from about 5 mg to about 200 mg; e.g., from about 50 mg to about 2000 mg, from about 50 mg to about 1000 mg, from about 50 mg to about 750 mg, from about 50 mg to about 600 mg, from about 50 mg to about 500 mg, from about 50 mg to about 400 mg, from about 50 mg to about 300 mg, from about 50 mg to about 200 mg; e.g., from about 100 mg to about 2500 mg, from about 100 mg to about 2000 mg, from about 100 mg to about 1000 mg, from about 100 mg to about 750 mg, from about 100 mg to about 700 mg, from about 100 mg to about 600 mg, from about 100 mg to about 500 mg, from about 100 mg to about 400 mg, from about 100 mg to about 300 mg, from about 100 mg to about 200 mg; e.g., from about 150 mg to about 2500 mg, from about 150 mg to about 2000 mg, from about 150 mg to about 1000 mg, from about 150 mg to about 750 mg, from about 150 mg to about 700 mg, from about 150 mg to about 600 mg, from about 150 mg to about 500 mg, from about 150 mg to about 400 mg, from about 150 mg to about 300 mg, from about 150 mg to about 200 mg; e.g., from about 150 mg to about 500 mg; e.g., from about 300 mg to about 2500 mg, from about 300 mg to about 2000 mg, from about 300 mg to about 1000 mg, from about 300 mg to about 750 mg, from about 300 mg to about 700 mg, from about 300 mg to about 600 mg; e.g., from about 400 mg to about 2500 mg, from about 400 mg to about 2000 mg, from about 400 mg to about 1000 mg, from about 400 mg to about 750 mg, from about 400 mg to about 700 mg, from about 400 mg to about 600 from about 400 mg to about 500 mg; e.g., 150 mg or 450 mg) of the chemical entity in from about 1 mL to about 3000 mL (e.g., from about 1 mL to about 2000 mL, from about 1 mL to about 1000 mL, from about 1 mL to about 500 mL, from about 1 mL to about 250 mL, from about 1 mL to about 100 mL, from about 10 mL to about 1000 mL, from about 10 mL to about 500 mL, from about 10 mL to about 250 mL, from about 10 mL to about 100 mL, from about 30 mL to about 90 mL, from about 40 mL to about 80 mL; from about 50 mL to about 70 mL; e.g., about 1 mL, about 5 mL, about 10 mL, about 15 mL, about 20 mL, about 25 mL, about 30 mL, about 35 mL, about 40 mL, about 45 mL, about 50 mL, about 55 mL, about 60 mL, about 65 mL, about 70 mL, about 75 mL, about 100 mL, about 250 mL, or about 500 mL, or about 1000 mL, or about 2000 mL, or about 3000 mL; e.g., 60 mL) of liquid carrier.

In certain embodiments, enema formulations include from about 50 mg to about 250 mg (e.g., from about 100 mg to about 200; e.g., about 150 mg) of the chemical entity in from about 10 mL to about 100 mL (e.g., from about 20 mL to about 100 mL, from about 30 mL to about 90 mL, from about 40 mL to about 80 mL; from about 50 mL to about 70 mL) of liquid carrier. In certain embodiments, enema formulations include about 150 mg of the chemical entity in about 60 mL of the liquid carrier. In certain of these embodiments, the chemical entity is niclosamide, or a pharmaceutically acceptable salt and/or hydrate and/or cocrystal thereof. For example, enema formulations can include about 150 mg of niclosamide in about 60 mL of the liquid carrier.

In certain embodiments, enema formulations include from about 350 mg to about 550 mg (e.g., from about 400 mg to about 500; e.g., about 450 mg) of the chemical entity in from about 10 mL to about 100 mL (e.g., from about 20 mL to about 100 mL, from about 30 mL to about 90 mL, from about 40 mL to about 80 mL; from about 50 mL to about 70 mL) of liquid carrier. In certain embodiments, enema formulations include about 450 mg of the chemical entity in about 60 mL of the liquid carrier. In certain of these embodiments, the chemical entity is niclosamide, or a pharmaceutically acceptable salt and/or hydrate and/or cocrystal thereof. For example, enema formulations can include about 450 mg of niclosamide in about 60 mL of the liquid carrier.

In some embodiments, enema formulations include from about from about 0.01 mg/mL to about 50 mg/mL (e.g., from about 0.01 mg/mL to about 25 mg/mL; from about 0.01 mg/mL to about 10 mg/mL; from about 0.01 mg/mL to about 5 mg/mL; from about 0.1 mg/mL to about 50 mg/mL; from about 0.01 mg/mL to about 25 mg/mL; from about 0.1 mg/mL to about 10 mg/mL; from about 0.1 mg/mL to about 5 mg/mL; from about 1 mg/mL to about 10 mg/mL; from about 1 mg/mL to about 5 mg/mL; from about 5 mg/mL to about 10 mg/mL; e.g., about 2.5 mg/mL or about 7.5 mg/mL) of the chemical entity in liquid carrier. In certain of these embodiments, the chemical entity is niclosamide, or a pharmaceutically acceptable salt and/or hydrate and/or cocrystal thereof. For example, enema formulations can include about 2.5 mg/mL or about 7.5 mg/mL of niclosamide in liquid carrier.

The foregoing dosages can be administered on a daily basis (e.g., as a single dose per day; or as two or more divided doses per day; or a two or more doses; e.g., two doses per day) or non-daily basis (e.g., every other day, every two days, every three days, once weekly, twice weeks, once every two weeks, once a month). In certain embodiments, dosages can be administered for about 1 week, about 2 weeks, about 3 weeks, about 4 weeks, about 5 weeks, about 6 weeks, about 7 weeks, about 8 weeks, about 3 months, about 6 months, about 1 year, or beyond. For example, dosages (e.g., about 2.5 mg/mL or about 7.5 mg/mL) of the chemical entity in liquid carrier can be administered twice a day on a daily basis for about 6 weeks. In certain of these embodiments, the chemical entity is niclosamide, or a pharmaceutically acceptable salt and/or hydrate and/or cocrystal thereof. For example, about 2.5 mg/mL or about 7.5 mg/mL of niclosamide in liquid carrier can be administered twice a day on a daily basis for about 6 weeks. Representative liquid carriers include, e.g., those previously described in conjunction with component (ii).

Methods of Treatment

In some embodiments, methods for inducing cell death of one or more T cells (e.g., in the digestive and/or gastrointestinal tract (GI), skin, eyes, or joints), of a subject are provided. The methods include contacting the one or more T cells with an effective amount of a chemical entity (e.g., a compound exhibiting activity as a mitochondrial uncoupling agent or a pharmaceutically acceptable salt and/or hydrate and/or cocrystal thereof; e.g., a compound, such as niclosamide or a pharmaceutically acceptable salt and/or hydrate and/or cocrystal thereof; e.g., a compound, such as a niclosamide analog, or a pharmaceutically acceptable salt and/or hydrate and/or cocrystal thereof) as defined anywhere herein. In certain embodiments, the methods consist essentially or consist of the contacting step described above in this paragraph.

In some embodiments, methods for treating a subject having a condition associated with unregulated (abnormal, elevated) recruitment and/or retention of one or more T cells (e.g., at the digestive and/or gastrointestinal tract (GI), skin, eyes, or joints) of the subject are provided. The methods include contacting the one or more T cells with an effective amount of a chemical entity (e.g., a compound exhibiting activity as a mitochondrial uncoupling agent or a pharmaceutically acceptable salt and/or hydrate and/or cocrystal thereof; e.g., a compound, such as niclosamide or a pharmaceutically acceptable salt and/or hydrate and/or cocrystal thereof; e.g., a compound, such as a niclosamide analog, or a pharmaceutically acceptable salt and/or hydrate and/or cocrystal thereof) as defined anywhere herein. In certain embodiments, the methods consist essentially of or consist of the contacting step described above in this paragraph.

In some embodiments, methods for treating a subject having a condition associated with unregulated (abnormal, elevated) activation of one or more T cells (e.g., in the digestive and/or gastrointestinal tract (GI), skin, eyes, or joints) of the subject are provided. The methods include contacting the one or more activated T cells with an effective amount of a cocrystal comprising (i) a mitochondrial uncoupling agent or a pharmaceutically acceptable salt and/or hydrate thereof; and (ii) one or more pharmaceutically acceptable coformers as defined anywhere herein. In certain embodiments, the methods consist essentially of or consist of the contacting step described above in this paragraph.

In some embodiments, inducing cell death of the one or more T cells includes one or more of the following pathways: Programmed cell death, Necroptosis, Apoptosis, Necrosis, Pyroptosis, Ferroptosis, Anoikis, Mitotic cathastrophe, Paraptosis, Pyronecrosis, Entosis, Netosis, Parthanatos, Autophagic cell death, RGD: regulated cell death, Non-apoptotic programmed cell-death, Caspase-independent programmed cell-death inducing necrosis or apoptosis of the one or more T cells, e.g., necrosis or apoptosis of the one or more T cells. In certain embodiments, the effective amount is an amount sufficient to induce cell death of at least one of the one or more T cells (e.g., by any one or more of the pathways described above, e.g., necrosis or apoptosis of the one or more T cells).

In some embodiments, the one or more T cells include one or more activated T cells, e.g., one or more activated T cells is independently selected from the group consisting of:

CD45+CD3+TCRαβ+CD62L-;
CD45+CD3+TCRαβ0+CD62L-CCR7-;
CD45+CD3+TCRαβ+CD62L-CD69+;
CD45+CD3+TCRαβ+CD62L-CD69+PD-1+;
CD45+CD3+TCRαβ+CD62L-CTLA4+;
CD45+CD3+TCRαβ+CD62L-PD-1++CTLA4+;
CD45+CD3+TCRγδ+CD62L-;
CD45+CD3+TCRγδ+CD62L-CCR7-;
CD45+CD3+TCRγδ+CD62L-CD69+;
CD45+CD3+TCRγδ+CD62L-CD69+PD-1+;
CD45+CD3+CD62L-TCRγδ+CTLA4+; and
CD45+CD3+TCRγδ+CD62L-PD-1++CTLA4+.

In certain embodiments, the effective amount is an amount sufficient to induce cell death of at least one of the one or more activated T cells (e.g., by any one or more of the pathways described above, e.g., necrosis or apoptosis of the one or more activated T cells).

In some embodiments, the one or more T cells are present within the intestinal epithelium and/or within the lamina propria and/or within the Peyer's patches (PP) and/or within the GALT (gut associated lymphoid tissue) and/or within the intestinal mucosa and/or within the intestinal submucosa and/or within the intestinal muscular layer and/or within the intestinal serosa.

In some embodiments, the one or more T cells comprise one or more gut tropic T cells. In certain embodiments, each of the one or more gut tropic T cells independently expresses one or more gut-homing receptors selected from the group consisting of:

(CD3+CCR9+;
CD3+α4+ or CD3+β7+;
CD3+α4+β7+;
CD3+β1+;
CD3+α4+β1+;
CD3+LFA1;
CD3+CCR4+; and
CD3+CCR10+.

In some embodiments, methods for treating a condition (or one or more symptoms thereof) characterized by an abnormal inflammatory response in a subject in need thereof are provided (e.g., an autoimmune disorder, e.g., an inflammatory bowel disease). The methods include administering to the subject an effective amount of a chemical entity (e.g., a compound exhibiting activity as a mitochondrial uncoupling agent or a pharmaceutically acceptable salt and/or hydrate and/or cocrystal thereof; e.g., a compound, such as niclosamide or a pharmaceutically acceptable salt and/or hydrate and/or cocrystal thereof; e.g., a compound, such as a niclosamide analog, or a pharmaceutically acceptable salt and/or hydrate and/or cocrystal thereof) as defined anywhere herein. In certain embodiments, the methods consist essentially of or consist of the administering step described above in this paragraph.

In some embodiments, methods for treating a condition (or one or more symptoms thereof) characterized by an abnormal inflammatory response in a subject in need thereof are provided (e.g., an autoimmune disorder, e.g., an inflammatory bowel disease). The methods include topically and locally administering to the subject an effective amount of a chemical entity (e.g., a compound exhibiting activity as a mitochondrial uncoupling agent or a pharmaceutically acceptable salt and/or hydrate and/or cocrystal thereof; e.g., a compound, such as niclosamide or a pharmaceutically acceptable salt and/or hydrate and/or cocrystal thereof; e.g., a compound, such as a niclosamide analog, or a pharmaceutically acceptable salt and/or hydrate and/or cocrystal thereof) as defined anywhere herein. In certain embodiments, the methods consist essentially of or consist of the administering step described above in this paragraph.

In some embodiments, methods for treating autoimmune colitis (or one or more symptoms thereof) in a subject are provided. The methods include topically and locally administering to the subject an effective amount of a chemical entity (e.g., a compound exhibiting activity as a mitochondrial uncoupling agent or a pharmaceutically acceptable salt and/or hydrate and/or cocrystal thereof; e.g., a compound, such as niclosamide or a pharmaceutically acceptable salt and/or hydrate and/or cocrystal thereof; e.g., a compound, such as a niclosamide analog, or a pharmaceutically acceptable salt and/or hydrate and/or cocrystal thereof) as defined anywhere herein. In certain embodiments, the methods consist essentially of or consist of the administering step described above in this paragraph.

In some embodiments, methods for treating a condition (or one or more symptoms thereof) selected from the group consisting of celiac disease, irritable bowel syndrome, mucositis, uveitis, collagenous colitis, lymphocytic colitis, microscopic colitis, radiation enteritis, rheumatoid arthritis, lupus, scleroderma, psoriasis, cutaneous T-cell lymphoma, acute graft vs. host disease and chronic graft vs. host disease in a subject are provided. The methods include topically and locally administering to the subject an effective amount of a chemical entity (e.g., a compound exhibiting activity as a mitochondrial uncoupling agent or a pharmaceutically acceptable salt and/or hydrate and/or cocrystal thereof; e.g., a compound, such as niclosamide or a pharmaceutically acceptable salt and/or hydrate and/or cocrystal thereof; e.g., a compound, such as a niclosamide analog, or a pharmaceutically acceptable salt and/or hydrate and/or cocrystal thereof) as defined anywhere herein. In certain embodiments, the methods consist essentially of or consist of the administering step described above in this paragraph.

In certain of these embodiments, the condition is an autoimmune disease. In certain embodiments, the condition is an inflammatory bowel disease. In certain embodiments, the condition is Crohn's disease, autoimmune colitis, iatrogenic autoimmune colitis, ulcerative colitis, colitis induced by one or more chemotherapeutic agents, colitis induced by treatment with adoptive cell therapy, colitis associated by one or more alloimmune diseases (such as graft-vs-host disease, e.g., acute graft vs. host disease and chronic graft vs. host disease), radiation enteritis, collagenous colitis, lymphocytic colitis, microscopic colitis, and radiation enteritis.

In certain of these embodiments, the condition is alloimmune disease (such as graft-vs-host disease, e.g., acute graft vs. host disease and chronic graft vs. host disease), celiac disease, irritable bowel syndrome, rheumatoid arthritis, lupus, scleroderma, psoriasis, cutaneous T-cell lymphoma, uveitis, and mucositis (e.g., oral mucositis, esophageal mucositis or intestinal mucositis).

In certain embodiments, the condition is autoimmune colitis.

In certain of these embodiments, the autoimmune colitis is induced by one or more chemotherapeutic agents, e.g., a chemotherapeutic immunomodulator, e.g., an immune checkpoint inhibitor. In certain of these embodiments, the immune checkpoint inhibitor targets an immune checkpoint receptor selected from the group consisting of CTLA-4, PD-1, PD-L1, PD-1-PD-L1, PD-1-PD-L2, interleukin-2 (IL-2), indoleamine 2,3-dioxygenase (IDO), IL-10, transforming growth factor-$\beta$ (TGF$\beta$), T cell immunoglobulin and mucin 3 (TIM3 or HAVCR2), Galectin 9-TIM3, Phosphatidylserine-TIM3, lymphocyte activation gene 3 protein (LAG3), MHC class II-LAG3, 4-1BB-4-1BB ligand, OX40-OX40 ligand, GITR, GITR ligand-GITR, CD27, CD70-CD27, TNFRSF25, TNFRSF25-TL1 A, CD40L, CD40-CD40 ligand, HVEM-LIGHT-LTA, HVEM, HVEM-BTLA, HVEM-CD 160, HVEM-LIGHT, HVEM-BTLA-CD160, CD80, CD80-PDL-1, PDL2-CD80, CD244, CD48-CD244, CD244, ICOS, ICOS-ICOS ligand, B7-H3, B7-H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, CD39, CD73 Adenosine-CD39-CD73, CXCR4-CXCL12, Phosphatidylserine, TIM3, Phosphatidylserine-TIM3, SIRPA-CD47, VEGF, Neuropilin, CD 160, CD30, and CD 155; e.g., CTLA-4 or PD1 or PD-L1). See, e.g., Postow, M. *J. Clin. Oncol.* 2015, 33, 1.

In certain of these embodiments, the immune checkpoint inhibitor is selected from the group consisting of: Urelumab, PF-05082566, MEDI6469, TRX518, Varlilumab, CP-870893, Pembrolizumab (PD1), Nivolumab (PD1), Atezolizumab (formerly MPDL3280A) (PDL1), MEDI4736 (PD-L1), Avelumab (PD-L1), PDR001 (PD1), BMS-986016, MGA271, Lirilumab, IPH2201, Emactuzumab, INCB024360, Galunisertib, Ulocuplumab, BKT140, Bavituximab, CC-90002, Bevacizumab, and MNRP1685A, and MGA271.

In certain of these embodiments, the immune checkpoint inhibitor targets CTLA-4, e.g., an antibody, e.g., ipilimumab or tremelimumab.

In certain of these embodiments, the immune checkpoint inhibitor targets PD1 or PD-L1, e.g., nivolumab, lambroizumab, or BMS-936559.

In certain embodiments, the condition is mucositis, also known as stomatitits, which can occur as a result of chemotherapy or radiation therapy, either alone or in combination as well as damage caused by exposure to radiation outside of the context of radiation therapy. Chemotherapeutic agents which may induce mucositis when used alone or in combination include, but are not limited to, platinum, cisplatin, carboplatin, oxaliplatin, mechlorethamine, cyclophosphamide, chlorambucil, azathioprine, mercaptopurine, vincristine, vinblastine, vinorelbine, vindesine, etoposide and teniposide, paclitaxel, docetaxel, irinotecan, topotecan, amsacrine, etoposide, etoposide phosphate, teniposide, 5-fluorouracil, leucovorin, methotrexate, gemcitabine, taxane, leucovorin, mitomycin C, tegafur-uracil, idarubicin, fludarabine, mitoxantrone, ifosfamide and doxorubicin. Additional agents include inhibitors of mTOR (mammalian target of rapamycin), including but not limited to rapamycin, everolimus, temsirolimus and deforolimus.

In certain embodiments, the condition is uveitis, which is inflammation of the uvea (e.g., anterior uveitis, e.g., iridocyclitis or iritis; intermediate uveitis (also known as pars planitis); posterior uveitis; or chorioretinitis, e.g., panuveitis).

This disclosure contemplates both monotherapy regimens as well as combination therapy regimens.

In some embodiments, monotherapy includes administering (e.g., topically and locally) to a subject an effective amount of a chemical entity (e.g., a compound exhibiting activity as a mitochondrial uncoupling agent or a pharmaceutically acceptable salt and/or hydrate and/or cocrystal thereof; e.g., a compound, such as niclosamide or a pharmaceutically acceptable salt and/or hydrate and/or cocrystal thereof; e.g., a compound, such as a niclosamide analog, or a pharmaceutically acceptable salt and/or hydrate and/or cocrystal thereof) as defined anywhere herein, but excludes the administration of other therapeutic agents (e.g., the active compounds, e.g., peptides, disclosed in U.S. Pat. No. 8,148,328, which is incorporated herein by reference in its entirety).

In some embodiments, the methods described herein can further include administering a second therapeutic agent or regimen.

In certain embodiments, the second therapeutic agent or regimen is administered to the subject prior to contacting with or administering the chemical entity (e.g., about one hour prior, or about 6 hours prior, or about 12 hours prior, or about 24 hours prior, or about 48 hours prior, or about 1 week prior, or about 1 month prior).

In other embodiments, the second therapeutic agent or regimen is administered to the subject at about the same time as contacting with or administering the chemical entity. By way of example, the second therapeutic agent or regimen and the chemical entity are provided to the subject simultaneously in the same dosage form. As another example, the second therapeutic agent or regimen and the chemical entity are provided to the subject concurrently in separate dosage forms.

In still other embodiments, the second therapeutic agent is administered to the subject after contacting with or administering the chemical entity (e.g., about one hour after, or about 6 hours after, or about 12 hours after, or about 24 hours after, or about 48 hours after, or about 1 week after, or about 1 month after).

In certain embodiments, the second therapeutic agent is a chemotherapeutic immunomodulator, e.g., an immune checkpoint inhibitor, which can be as defined anywhere herein. In other embodiments, the second therapeutic agent or regimen is one or more anti-inflammatory agents or immunomodulator acting locally in the GI tract. In other embodiments, the second therapeutic agent or regimen is 5-ASA (and associated delivery systems), anti-SMAD7 antisense, orally formulated anti-INFs, anti-integrins, sulfasalazine, balsalazide, steroids, azathioprine, and methotrexate. In further embodiments, the second therapeutic agent or regimen is radiation or surgery.

In certain embodiments, the second therapeutic agent is platinum, cisplatin, carboplatin, oxaliplatin, mechlorethamine, cyclophosphamide, chlorambucil, azathioprine, mercaptopurine, vincristine, vinblastine, vinorelbine, vindesine, etoposide and teniposide, paclitaxel, docetaxel, irinotecan, topotecan, amsacrine, etoposide, etoposide phosphate, teniposide, 5-fluorouracil, leucovorin, methotrexate, gemcitabine, taxane, leucovorin, mitomycin C, tegafur-uracil, idarubicin, fludarabine, mitoxantrone, ifosfamide and doxorubicin. Additional agents include inhibitors of mTOR (mammalian target of rapamycin), including but not limited to rapamycin, everolimus, temsirolimus and deforolimus.

In still other embodiments, the second therapeutic agent can be selected from those delineated above (see U.S. Pat. No. 7,927,613, which is incorporated herein by reference in its entirety).

In some embodiments, the methods described herein further include the step of identifying a subject (e.g., a patient) in need of such treatment (e.g., by way of biopsy, endoscopy, or other conventional method known in the art).

In some embodiments, the chemical entities, methods, and compositions described herein can be administered to certain treatment-resistant patient populations, e.g., one that is nonresponsive or resistant to treatment with an anti-TNFalpha therapy (e.g., Humira, Enbrel, Remicade, Cimzia, Simponi, Enbrel, xanthine derivatives, e.g., pentoxifylline and Bupropion; (R)-DOI, TCB-2, LSD and LA-SS-Az). In certain embodiments, the patient is undergoing and/or has undergone treatment with an anti-TNFalpha therapy (e.g., Humira, Enbrel, Remicade, Cimzia, Simponi, Enbrel, xanthine derivatives, e.g., pentoxifylline and Bupropion; (R)-DOI, TCB-2, LSD and LA-SS-Az).

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

EXAMPLES

Example 1: Niclosamide Uncouples Mitochondrial Respiration from Oxidative Phosphorylation Jurkat T Cells Objective. To measure the dose-response effect of niclosamide on mitochondrial transmembrane potential in Jurkat T cells using the lipophilic cationic dye, tetramethylrhodamine, methyl ester (TMRM).

Model. The Jurkat T cell model is commonly used to study the potential effects of compounds on T cells in vitro. This cell line allows investigation of stimuli and mechanisms that regulate T cell mitochondrial function and survival. As T cells, Jurkats have a lymphocyte appearance and replicate in culture in suspension. They contain respiring mitochondria and as such response to mitochondrial uncouplers such as niclosamide may be assessed. Uncoupling is identified and quantified by a detecting a drop in the electrochemical gradient across the mitochondrial inner membrane ($\Delta\Psi m$) that is not associated with a corresponding increase in oxidative phosphorylation. Experiments to detect changes in $\Delta\Psi m$ were performed by including conditions in which a concentration of oligomycin was added to irreversibly inhibit the $F_1F_0$-ATPase and block oxidative phosphorylation to demonstrate that the fall in $\Delta\Psi m$ represents uncoupling since it occurred independent of an increase in mitochondrial oxidative phosphorylation.

Cell culture. Jurkat T cells were purchased from the American Type Culture Collection (Manassas, Va.) and sub-cultured according to instructions from the supplier. Prior to experiments, cells were cultured in RPMI 1640 containing 10% FBS-HI, 50 units penicillin/mL and 50 μg streptomycin/mL, and maintained in log phase prior to experimental setup. Cells were grown in a 5% $CO_2$ humidified incubator at 37° C. Growth medium was made by adding 50 mL of heat inactivated FBS and 5 mL of penicillin/streptomycin to 500 mL DMEM. This medium was stored at 4° C. Before use, the medium was warmed to 37° C. in a water bath. Jurkat cells were seeded at an initial density of $5 \times 10^4$ cells/mL in 24-well plates. The cells were allowed to grow for 18 hours prior to treatment being added.

Treatment with niclosamide. Niclosamide was dissolved in dimethyl sulfoxide (DMSO) and added to the culture medium to achieve concentrations of 500, 100, 50, 10, 5 or 1 μM. Oligomycin was dissolved in DMSO then added to test wells in 10 μL to achieve a final concentration of 1 μL Samples were incubated for 60 minutes at 37° C. TMRM dissolved in DMSO then added to the test wells in 10 μL to achieve a final concentration of 5 μM and allowed to incubate at 37° C. for an additional 30 min. A vehicle only control (in place of niclosamide) was run concurrently with each experiment A flow cytometer providing excitation at 560 nm and detection at 590 nm emission was used for quantification of TMRM fluorescence.

Measuring mitochondrial membrane potential changes ($\Delta\Psi m$). TMRM has advantages over other cationic dyes in that it can selectively enter into mitochondria and reversibly accumulate as the membrane potential increases. The accumulation of TMRM in mitochondria has been shown to be driven by their membrane potential Moreover, because of reduced hydrophobic character, this probe exhibits potential-independent binding to cells that is 10 to 20 times lower than that seen with other probes. TMRM has been described as one of the best fluorescent dyes for dynamic and in situ quantitative measurements because it is rapidly and reversibly taken up by live cells and mitochondria.

Calculation of relative decrease in mitochondrial membrane potential. Median fluorescence intensity was computed for all concentrations of niclosamide relative to vehicle-only negative controls in the presence of oligomycin. Ratios of the fluorescence intensity of each treated sample to the control sample mean were then calculated as a measure of relative decrease in $\Delta\Psi m$. For statistical comparisons, 95% confidence intervals were computed and graphed with the mean values of this ratio. By utilizing the 95% confidence intervals, the probability of a type I error was set at the nominal 5% level.

Results Niclosamide exhibits a dose-related decrease in $\Delta\Psi m$ in Jurkat cells with concentrations of niclosamide of 5 μM and above significantly decreased ($p<0.05$) relative to negative controls.

Example 2: Niclosamide Uncouples Mitochondrial Respiration from Oxidative Phosphorylation in T Cells Isolated from the Lamina Propria of Human Intestine Objective. The objective of this experiment is to determine if niclosamide can directly reduce the mitochondrial transmembrane potential in T cells isolated from human intestine lamina propria in a manner similar to effects observed in Jurkat T cells.

Model. Lamina propria mononuclear cells (LPMC) in the human intestine are comprised in part by T cells, which mediate physiological and pathological processes including inflammatory bowel disease. LPMCs can be isolated from human tissue biopsies. After isolation LPMCs T cells remain viable ex vivo under appropriate culture conditions for periods of time that allow ex vivo experiments. These cells can be used to investigate mechanisms that regulate their mitochondrial function and survival. They contain respiring mitochondria and as such their response to mitochondrial uncouplers such as niclosamide may be assessed. This cellular model is used in conjunction with oligomycin that blocks oxidative phosphorylation and TMRM to monitor $\Delta\Psi m$ as described in Example 1.

Cell isolation and culture. Cells are obtained from biopsy specimens of the small or large intestine or rectum of humans from areas of normal gastrointestinal tissue or with moderate to severe Crohn's disease (CD), ulcerative colitis (UC), or celiac disease. For the isolation of lamina propria mononuclear cells (LPMCs), the specimens are initially washed in Hank's balanced salt solution (HBSS) then are cut into 0.5-cm pieces, and are incubated with stirring in pre-warmed HBSS containing 1 mM DTT at 37° C. for 15 minutes. The supernatant is removed and the sample is washed with stirring with HBSS for 5 minutes twice. Samples are incubated with stirring in pre-warmed HBSS containing 5 mM EDTA for 30 minutes. The supernatant is removed and the sample is washed with stirring with HBSS for 5 minutes three times. The tissue is then digested further in RPMI 1640 containing 2 mg/mL Liberase and 0.01 μg/mL DNase I for 1 hour at 37° C. with stirring. After digestion, the mononuclear cells in suspension are collected and are centrifuged at 400 g for 10 minutes. After two washings in HBS, the pellet is resuspended in a 40% Percoll solution and is layered on the top of a Percoll solution (100%, 60%, 40%, and 30% Percoll in HBSS). The tube is centrifuged at 400 g for 25 minutes, and LPMCs at the 60%-40% Percoll layer interface are ollected. The isolated cells are counted and checked for viability using 0.1% trypan blue (viability ranges from 86% to 94%). Cells are washed out of Percoll with HBSS and are resuspended in RPMI 1640 supplemented with 10% heat inactivated FBS, 1% L-glutamine, 100 U/mL penicillin, and 100 mg/mL streptomycin at a concentration of $1 \times 10^6$ cells/mL and are plated in 96-well culture plates (200000 cells/well) (Nat Protoc. 2007; 2(10): 2307-11).

Treatment with test material. The protocol as noted in Example 1 is followed. In addition, anti-CD3 monoclonal antibody conjugated to FITC (excitation at 494 nm with emission detected at 521 nm) is additionally added during incubation with TMRM at 37° C. for 30 minutes.

Measurement of and calculation of change of $\Delta\Psi m$ in T cells. In order to specifically distinguish T cells from other cells in LPMCs, anti-CD3 monoclonal antibody labeled with FITC is used. This antibody specifically binds human CD3 antigen that is selectively expressed on T cells. LPMC T cells are first defined by their fluorescence emission at 521 nm resulting from labeling with FITC-anti-CD3 antibody. The n fluorescence intensity of TMRM detected at 590 nm in the T cell population is measured. Median fluorescence intensity of the TMRM signal are computed. Ratios of the median fluorescence intensity of each treated sample to the control sample mean are then calculated as a measure of relative decrease in $\Delta\Psi m$. For statistical comparisons, 95% confidence intervals are computed and graphed with the mean values of this ratio.

Results. Niclosamide induces a dose-related decrease in $\Delta\Psi m$ in human LPMCs T cells with concentrations of niclosamide of 5 μM and above ($p<0.05$) relative to negative controls.

Example 3: Niclosamide Induces Death of LPMC T Cells at Concentrations that Cause Mitochondrial Uncoupling Objective. The objective of this experiment was to determine if concentrations of niclosamide that uncouple mitochondria in LPMC induce cell death.

Model. The human LPMC model as described in Example 2 was used.

Cell isolation and culture. Cell isolation and culture procedures were as detailed in Example 2.

Treatment with Niclosamide. Niclosamide was dissolved in dimethyl sulfoxide (DMSO) and added to the culture medium to achieve concentrations of 500, 100, 50, 10, 5 or 1 µM. Samples were incubated for 60 minutes at 37° C. Cultured cells were incubated with DMSO (negative control), or stimulated with a human monoclonal anti-FAS-activating antibody (positive control, final concentration, 1 µg/mL), or concentrations of niclosamide at 37° C. for 24 hours. After treatment cells were exposed to 1 µM 7AAD then incubated a further 60 minutes at 37° C. Live cells and dead cells were enumerated by flow cytometer using a FACS Verse cytometer set to excite and measure emitted fluorescence of 7-AAD at appropriate wavelengths.

Detecting viable and dead cells. 7-AAD is excluded from live cells but free to enter dead cells where it undergoes a spectral shift after interacting with cellular DNA. Thus dead cells are selectively labeled with 7-AAD resulting in their detection with an emission maxima of 647 nm. Use of this reagent allows viable cells and dead cells to be simultaneously enumerated. In order to specifically distinguish T cells from other cells in LPMCs, anti-CD3 monoclonal antibody labeled with FITC (excitation at 494 nm with emission detected at 521 nm) will be used. This antibody specifically binds human CD3 antigen that is selectively expressed on T cells. Cell viability and death was determined specifically in T cells by measuring 7-AAD fluorescence in cells labeled by anti-CD3 FITC.

Calculation of T cell death. The fluorescence intensity of 7-AAD detected at 647 nm was measured specifically T the cell population that was first defined as described in Example 2 by FITC-anti-CD3 antibody fluorescence. In each experiment the 7-AAD fluorescence intensity value below which >95% of untreated control (live) T cells were detected was used as a cut point to calculate viability. Using this cut-point, the fraction of dead cells in a sample of >10,000 individual cells was calculated for each condition and expressed as mean values. For statistical comparisons, 95% confidence intervals were computed and graphed with the mean values.

Results. Niclosamide exhibits a dose-related increase in LPMC T cell death. Concentrations of niclosamide of 5 µM and above significantly increase death (p<0.05) relative to negative controls with vehicle alone. Concentrations below 5 µM fail to induce T cell death. The dose-response relationships of niclosamide-associated T cell death and niclosamide associated uncoupling in LPMCs were compared. The overlapping nature of these dose relationships indicates an association between niclosamide induced mitochondrial uncoupling and cell death.

Example 4: Niclosamide is an Effective Treatment for Inflammatory Bowel Disease in Mice Objective. The objective of this experiment is to determine if niclosamide is an effective treatment in a rodent model of colits.

Model. The TNBS-induced colitis is a commonly used experimental model for Inflammatory Bowel Disease (IBD). TNBS (trinitrobenzenesulfonic acid) is a chemical administered rectally in the form of an enema to mice or rats in combination with ethanol, which disrupts the mucous barrier, and induces colitis by haptenating proteins within the gut, causing them to become preferential targets for immune cells. The severity of TNBS-induced colitis depends largely on the dosage applied and the strain of animal used. In chronic, relapsing form of the model, animals are sensitized by escalating, intracolonic doses of TNBS. Disease is monitored in-life by weight loss. Histology of colon specimens is used to determine disease severity at study termination (Gastroenterology. 2003 December; 125(6). 1750-61; Inflamm Bowel Dis. 2006 October; 12(10):995-9.)

Mouse strain and housing. C57BL/6J female mice (9-weeks old) are purchased by Jackson and are housed at a temperature ranging from 68 to 74° F. with a diurnal 12 hour light cycle in a specific pathogen-free facility in ventilated cages. Food and water is provided ad libitum. Animals are acclimated to local microbiota for 7 days before the beginning of the experiment. Cell isolation and culture procedures are as noted in Example 2.

Conditioning to induce colitis. To perform the studies of relapsing hapten-induced colitis 4 escalating doses of TNBS in 50% ethanol are administered at weekly intervals to lightly anesthetized mice through a 3.5Fr catheter inserted into the rectum. The catheter tip is inserted 4 cm proximal to the anal verge, and 150 µL of fluid is slowly instilled into the colon, after which the mouse is held in a vertical position for 30 seconds per rectum at weekly intervals. The first and second doses are 0.5 mg TNBS, whereas the third and fourth doses are 0.75 and 1 mg TNBS. A control group is administered every week with 50% ethanol using the same procedure. Animal niclosamide is dissolved in water and is administered at 1, 3, 10, 30, 100 mg/kg at daily intervals to lightly anesthetized mice through a 3.5Fr catheter inserted into the rectum. Control mice are administered with water using the same procedure.

Clinical assessment of disease. For the clinical assessment of colitis, animal weight, diarrhea (0=absent; 1=present), rectal prolapse (0=absent; 1=present) and presence of blood in the stool (0=absent; 1=present) is recorded daily.

Histological assessment of disease. For histologic analysis, tissues are fixed in OCT, are cut into sections, and are stained with H&E. Histology scoring for individual mice is performed by a pathologist blinded to the samples, and the degree of inflammation on microscopic cross-sections of the colon is graded semiquantitatively from 0 to 4. Tissues that are removed from mice at indicated times of death are fixed in 10% formalin solution, are embedded in paraffin, are cut into tissue sections and are stained with hematossiline and cosine. Stained sections are examined for evidence of colitis using different criteria such as the presence of lymphocyte infiltration, elongation and/or distortion of crypts, frank ulceration and thickening of the bowel wall. The degree of inflammation on microscopic cross-sections of the colon is graded from 0 to 4 as follows: 0: no evidence of inflammation; 1: low level of lymphocyte infiltration with infiltration seen in a <10% high-power field (hpf=high power field), no structural changes observed; 2: moderate lymphocyte infiltration with infiltration seen in <10-25% hpf, crypt elongation, bowel wall thickening which does not extend beyond mucosal layer, 3: high level of lymphocyte infiltration with infiltration seen in <25-50% hpf, thickening of bowel wall which extends beyond mucosal layer; 4: marked degree of lymphocyte infiltration with infiltration seen in >50% hpf, high vascular density, crypt elongation with distortion, transmural bowel wall-thickening with ulceration (J Exp Med. 1995 Nov. 1,182(5): 1281-90, Current Protocol Immunology 15.19 DOI. 10.1002/0471142735.im1519s49).

Calculation of therapeutic effects. For statistical comparisons, two-way Anova test with Bonferroni correction is calculated with GaphPrism software.

Results. Niclosamide exhibits a dose-related decrease in colitis clinical scores and histologic scores. Therapeutic doses of niclosamide of 3 mg/kg and above significantly reduce both clinical and histologic scores (p<0.05) relative to vehicle control.

Example 5: Therapeutic Doses of Niclosamide in Mice are Associated with a Colon to Plasma Exposure Ratio that Exceeds 10:1

Objective. The objective of this experiment is to determine plasma and colon concentration and calculate colon to plasma exposure in mice dosed rectally with niclosamide.

Model. Mice are used as an effective model to correlate therapeutic responses with the drug concentrations that can be measured in the blood (serum or plasma fraction) and in tissues to determine the effectiveness of a treatment strategy designed to provide colon topical administration as opposed to systemic absorption. By measuring test agent concentrations in the strain of mice in which therapeutic responses to colitis are observed, conclusions can be reached as to whether topical colonic delivery produces a high colon: plasma ratio of drug exposure and sufficient colon concentrations of the test agent to account for therapeutic effects that are independent of absorption and systemic exposure to the test agent.

Mice. Nine week old C57BL/6J female mice are purchased by Jackson and are housed at a temperature ranging from 68 to 74° F. with a diurnal 12 hour light cycle in a specific pathogen-free facility in ventilated cages. Food and water is provided ad libitum. Animals are acclimated to local microbiota for 7 days before the beginning of the experiment.

Niclosamide administration. Niclosamide is dissolved in water and a single dose administered at 3 mg/kg to lightly anesthetized mice through a 3.5Fr catheter inserted into the rectum.

Pharmacokinetic study design. At 0.25, 0.5, 1, 2, 4, 8 16 hours after niclosamide administration, plasma and colon specimens are collected from 3 mice per time point and high-performance liquid chromatography is used to measure the tissue concentrations niclosamide and its metabolites.

Calculation of plasma and colon ratio. The mean concentration of niclosamide colon concentration (mg/mg) and niclosamide plasma concentration (mg/mL) is plotted and the ratio is calculated.

Results. Niclosamide exhibits a colon to plasma exposure ratio that exceeds 10:1.

Example 6: Doses of Niclosamide that are Therapeutic Against Colitis Result in Colonic Exposure Levels in Mice that are Associated with Mitochondrial Uncoupling Objective. To determine if niclosamide colonic exposure is associated with niclosamide concentrations that induce mitochondrial uncoupling.

Model. Results from Examples 2 and 5 are used together. Example 2 is used to define a dose-response relationship between Niclosamide concentration and mitochondrial uncoupling. Using the pharmacokinetic data from Example 5, the maximum Niclosamide concentration in colon is determined. This concentration is directly compared to the dose-response data to determine if efficacious exposure is sufficient to induce mitochondrial uncoupling in colon.

Niclosamide administration. Niclosamide is dissolved in water and a single dose is administered at 1 or 3 mg/kg to lightly anesthetized mice through a 3.5Fr catheter inserted into the rectum.

Pharmacokinetic study design. At 0.25, 0.5, 1, 2, 4, 8, and 16 hours after niclosamide administration, colon specimens are collected from 3 mice per time point per group and high-pressure liquid chromatography is used to measure the tissue concentrations of niclosamide and its metabolites.

Calculation of target coverage. The average area under the colon concentration versus time curve (AUC) and the peak concentration is calculated and is plotted and is graphed. Y axis represents niclosamide concentration in µM while X axis represents time. To estimate target coverage, the graph includes a horizontal line at the level in which niclosamide induces mitochondrial uncoupling in lamina propria T cell.

Results. At doses below maximal efficacy (e.g. 1 mg/kg), niclosamide does not reach 5 µM concentration in the colon. At therapeutic dosage of 3 mg/kg Niclosamide reaches a colon peak concentration >5 µM. Since 5 µM is the niclosamide concentration able to induce mitochondrial uncoupling more than 50% of in lamina propria T cell, this data indicate that efficacious exposures result in colon concentration of niclosamide that are associated with mitochondrial uncoupling and demonstrate that the therapeutic mechanism is associated with mitochondrial uncoupling.

FIG. 1. Niclosamide induces cell death in lamina propria T cell from active IBD. LPMC (lamina propria mononuclear cells) from IBD subjects were isolated from macroscopically inflamed intestinal area and treated with DMSO or niclosamide (10 µM) for 16 hours. Cell death in lamina propria T cell (CD3+) was determined by measuring 7-AAD staining by flow cytometry.

Figure 2:
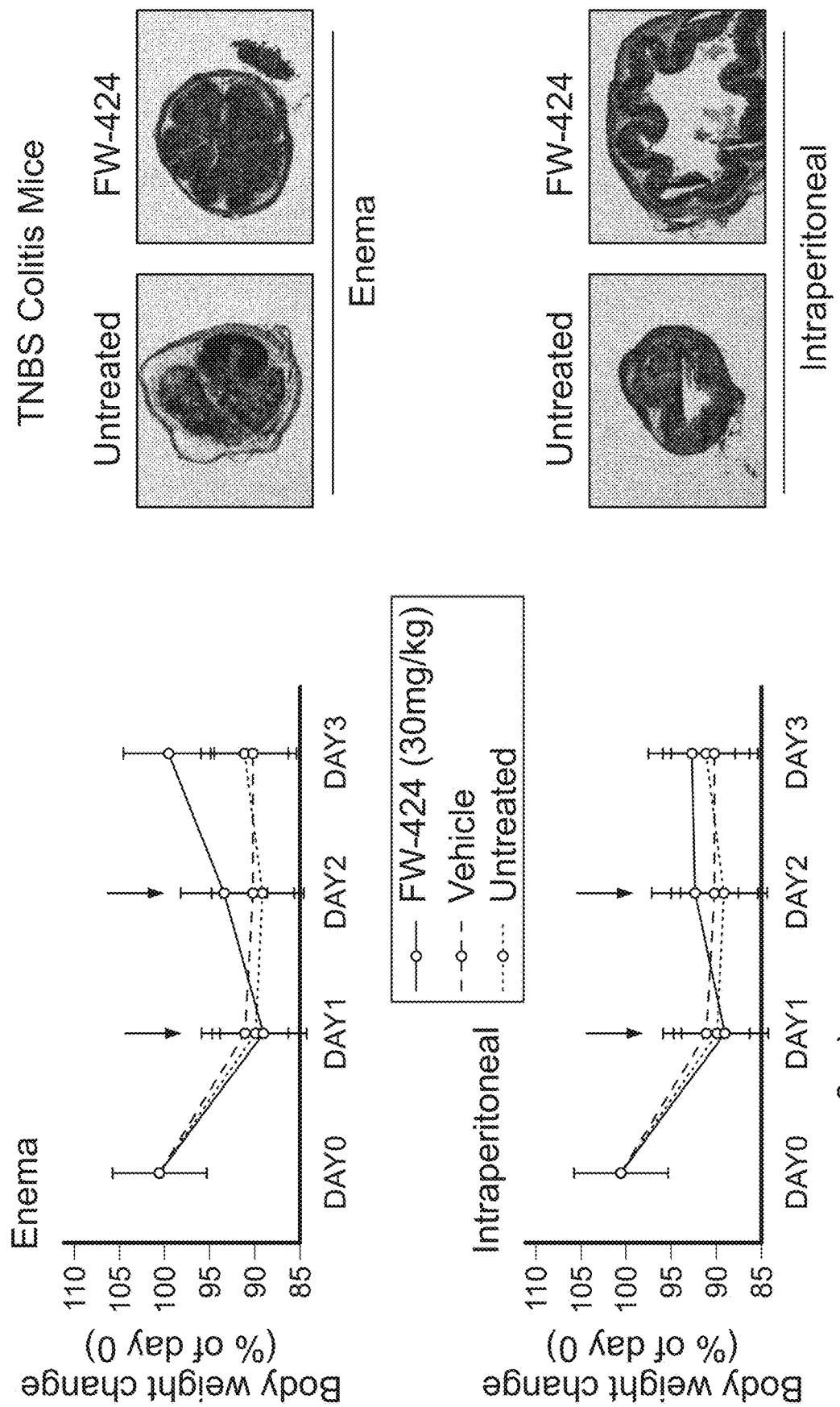
FIG. 2 includes graphs and images showing that niclosamide exhibits robust efficacy in murine TNBS model of ulcerative colitis when administered rectally (locally), but not by intraperitoneal injection (systemically).

FIG. 2 includes graphs and images showing that niclosamide exhibits robust efficacy in murine TNBS model of ulcerative colitis when administered rectally (locally), but not by intraperitoneal injection (systemically).

Example 7: Synthesis of Co-Crystals

A) L-Proline (35.2 mg) and niclosamide (100 mg) are combined in a steel vessel containing a steel ball. To this mixture is added 5 drops of ethanol. The sample is milled for 15 minutes after which time conversion to co-crystal is substantially complete.

The above example is meant to illustrate but not limit the invention. Other methods for achieving the described invention include grinding with a mortar and pestle, co-milling, slurry conversion, and concentration of a solution of both components.

It is understood by those skilled in the art that a similar co-crystal can be produced from D-proline and from mixtures of L- and D-proline such as a racemic mixture thereof.

B) L-Proline (35.2 mg) and niclosamide (100 mg) are combined in a steel vessel containing a steel ball. To this mixture is added 5 drops of propylene glycol. The sample is milled for 15 minutes after which time conversion to cocrystal is substantially complete.

C) Imidazole (20.8 mg) and niclosamide (100 mg) are combined in a steel vessel containing a steel ball. To this mixture is added 5 drops of ethanol. The sample is milled for 15 minutes after which time conversion to co-crystal is substantially complete.

The above example is meant to illustrate but not limit the invention. Other methods for achieving the described invention include grinding with a mortar and pestle, co-milling, slurry conversion, and concentration of a solution of both components.

Example 8: Preparation of Enema Formulation Components

The liquid carrier shown in Table 11 below were prepared according to the following procedure, propyl 4-hydroxybenzoate and methyl 4-hydroxybenzoate were dissolved in hot water. The solution was allowed to cool to room temperature, and additional water was added to compensate water loss due to evaporation that occurred in the prior step. The sodium salts were added and dissolved under stirring for 10 minutes (pH: 6.5-7.5). Methylcellulose and povidone were dispersed using a turbomixer (9000 rpm, 30′). The preparation was allowed to stand for several hours to let foam decant. Typically, the preparation of the liquid carrier was not stored and used immediately. However, when stored, the liquid carriers were stored in 500 mL polyethylene bottles. The liquid carrier exhibited the properties shown in Table 11.

TABLE 11

| Components | Quantity (%) |
|---|---|
| Methyl cellulose (Methocel A15C premium) | 1.40 |
| Povidone (Kollidon K30) | 1.00 |
| Propyl parahydroxybenzoate | 0.02 |
| Methyl parahydroxybenzoate | 0.20 |
| Disodium phosphate dodecahydrate | 0.15 |
| Sodium dihydrogen phosphate dihydrate | 0.05 |
| Water purified | Up to 100 |
| Technological characterization (as IPC) | |
| Appearance | Clear to opalescent colloidal dispersion |
| Dynamic viscosity * | 41 mPas s |
| pH | 7.023 |
| Density | 1.0075 g/mL |

The wet granulation preparations shown in Table 12 were prepared according to the following procedure. The internal phase ingredients are combined and mixed in a high-shear granulator. A granulating solution was prepared from water and the indicated agents. This solution is added to the mixture of the inner phase resulting in the formation of granules. Once the granulation was formed and dried, the external phase ingredients were added to the dry granulation. The resultant wet granulation preparations can be suspended in the above-described liquid carriers using conventional procedures.

TABLE 12

| | | Niclosamide Strength | | | | | |
|---|---|---|---|---|---|---|---|
| | | 450 mg | | | | | 450 mg |
| | | Component (%) | | | | | |
| Inner phase | Niclosamide | 100 | 98.5 | 77 | 66 | 50 | 61.64 |
| | Colloidal silicon dioxide (Aerosil 200) | — | 1.0 | | | | — |
| | Magnesium stearate | — | 0.5 | | | | |
| | Cellulose microcrystalline (Avicel PH101) | — | — | 23 | 34 | 50 | — |
| | Crospovidone (Kollidon CL) | — | — | — | — | — | 1.92 |
| | Lactose monohydrate (Pharmatose 200 M) | — | — | — | — | — | 30.82 |
| Granulating solution | Povidone (Kollidon K30) | — | — | — | — | — | 2.74 |
| | Sodium lauryl sulfate | — | — | — | — | — | 0.68 |
| | Purified water | — | — | — | — | — | * |
| External phase | Talc | — | — | — | — | — | 1.92 |
| | Magnesium stearate | — | — | — | — | — | 0.27 |
| Theoretical weight (mg) | | 450 | 456.9 | 593.4 | 692.3 | 913.8 | 730.0 |

*quantity used: 123 mg/units, removed during the process

| Process Parameter | | |
|---|---|---|
| 1) Calibration step raw materials | Manual calibration | |
| 1.1) Calibration sieve | Size 1.0 mm | |
| 2) Mixing step | Turbula, glass container | — |
| 2.1) Mixing time - rotation speed | 5′-34 rmp | — |
| 3) Granulation step | — | Manual granulation |
| 3.1) wet granulate sieve | | 1.0 mm |

TABLE 12-continued

| Technological Characterization | | | | |
|---|---|---|---|---|
| | | Granulate | | |
| Loss on drying (105° C. for 10') | | — | | 1.4% |
| | | Final mix | | |
| Flowability* | 10, 0 | It did not pass | | It did not pass |
| Flow throw an orifice of Ø (mm): | 15, 0 | It did not pass | | 6.1 g/sec |
| | 25, 0 | It did not pass | | 17.8 g/sec |
| Suspendability | | Not homogeneous suspendability and very poor mixture wettability | | Rapid and Homogeneous pH 6.9 |

*100 g of granulate have to pass through an orifice of increasing size 10 or 15 or 25 (etc.) mm diameter and the size of the orifice is increased if the powder is not passing through. When it passes the time is taken so that the smaller the diameter of the orifice and higher the amount/second the better it is for the flow properties of the granulate.

| Analytical test | | |
|---|---|---|
| Niclosamide assay (%) | — | 58.84% |

Example 9. Niclosamide Suspension Administered Rectally as an Enema has Efficacy in a Mouse Model of Ulcerative Colitis Objective: The objective of this experiment was to determine if niclosamide suspension administered rectally as an enema to mice with colitis reduces disease activity.

Model: Intra-rectal administration of trinitrobenzene sulfonic acid (TNBS) to mice results in colitis. TNBS elicits cell-mediated immune responses and induces transmural inflammation in the gut with morphological and histopathological features similar to those of human inflammatory bowel disease. TNBS induces diffuse colonic inflammation, characterized by increased leukocyte infiltration, edema, and ulceration. It is very well reported that administration of TNBS is associated with predominant activation of Th1-mediated immune response manifested by increased cytokines such as interferon-γ (IFN-γ), tumor necrosis factor-α (TNF-α) and interleukin-17A (IL-17A) as well as dense infiltration of CD4+ T cells. Disease activity in the TNBS model can be determined by loss of body weight, histopathological evaluation of the colon showing evidence of inflammatory damage and evidence of pro-inflammatory cytokines detected in colon tissue.

Animals and Treatments: Studies of TNBS colitis were performed in 8- to 12-week-old male Balb/c mice (Jackson Laboratories, stock number 000651). For induction of colitis, 2.5 mg of TNBS (Sigma-Aldrich, Milan, Italy) in 50% ethanol was administered to lightly anesthetized mice through a 3.5F catheter inserted into the rectum. The catheter tip was inserted 4 cm proximal to the anal verge, and 150 µL of fluid was slowly instilled into the colon, after which the mouse was held in a vertical position for 30 seconds. Mice were exposed to TNBS or 50% ethanol vehicle (EtOH) on Day 0. TNBS or EtOH exposed mice were subsequently dosed rectally with either nothing, vehicle used for niclosamide (phosphate buffered saline) or niclosamide enema suspension (0.03; 3; 30 mg/kg as indicated) by administering a 150 µl volume of niclosamide suspension prepared as a 4; 0.4; 0.04 mg/ml suspension of niclosamide (Sigma-Aldrich) in phosphate buffered saline. Niclosamide or vehicle only were administered on day 1 and day 2. Weight changes were recorded daily and tissues were collected for histologic study and RNA analysis at the end of the study.

Histopathology; For histologic analysis, tissues were fixed in 10% neutral buffered formalin solution, embedded in paraffin, cut into tissue sections, and stained with hemaotoxylin & eosin (H&E). For TNBS-induced colitis, stained sections were examined for evidence of colitis and assigned a colitis score (0-5) by considering the presence of acute and chronic inflammatory infiltrates, elongation and/or distortion of crypts, frank ulceration, and thickening of the bowel wall.

RNA Extraction, cDNA Preparation, and Real-Time PCR for Cytokine Detection:

RNA was extracted from fresh mucosal samples of treated mice using Trizol reagent according to the manufacturer's instructions (Invitrogen, Carlsbad, Calif.). A constant amount of RNA (1 mg per sample) was reverse-transcribed into cDNA, and this was amplified using a sybergreen-based PCR (Bio-Rad, Hercules, Calif.) using PCR conditions and primer sequences appropriate for specific detection of IL-17A, IFN-γ and TNF-α β-actin was used as a housekeeping gene to determine relative expression. Gene expression was calculated using the $\Delta\Delta Ct$ algorithm.

Figure 4A:
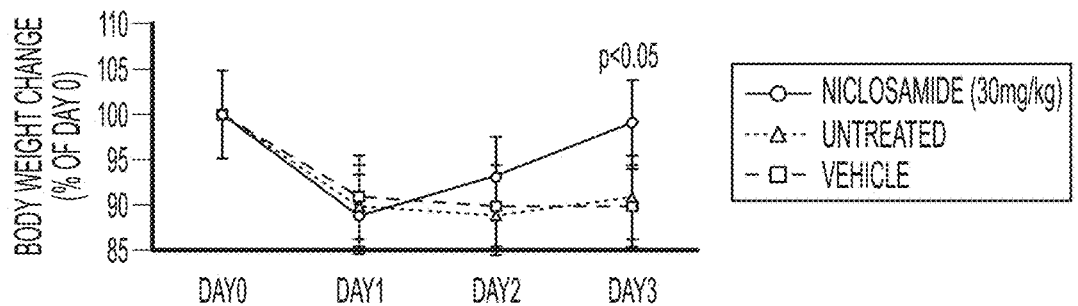
FIG. 4A is a graph showing that niclosamide suspension administered rectally at a dose of 30 mg/kg on days 1 and 2 results in recovery of body weight initially last due to TNBS-induced colitis. There is no recovery of weight in untreated or vehicle control treated mice.

Results and Conclusions—As shown in FIG. 4A, niclosamide suspension administered rectally at a dose of 30 mg/kg on days 1 and 2 results in recovery of body weight initially last due to TNBS-induced colitis. There is no recovery of weight in untreated or vehicle control treated mice.

Figure 4B:
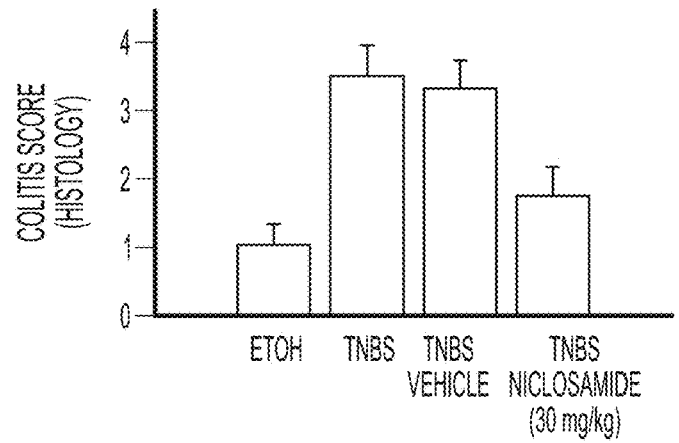
FIG. 4B is a graph showing that niclosamide suspension administered rectally at a dose of 30 mg/kg on days 1 and 2 results in a significantly lower colitis score compared to vehicle control treated mice or mice that received TNBS and no other treatment, based on H&E analysis of colon biopsies.

As shown in FIG. 4B, niclosamide suspension administered rectally at a dose of 30 mg/kg on days 1 and 2 results in a significantly lower colitis score compared to vehicle control treated mice or mice that received TNBS and no other treatment, based on H&E analysis of colon biopsies.

Figure 4C:
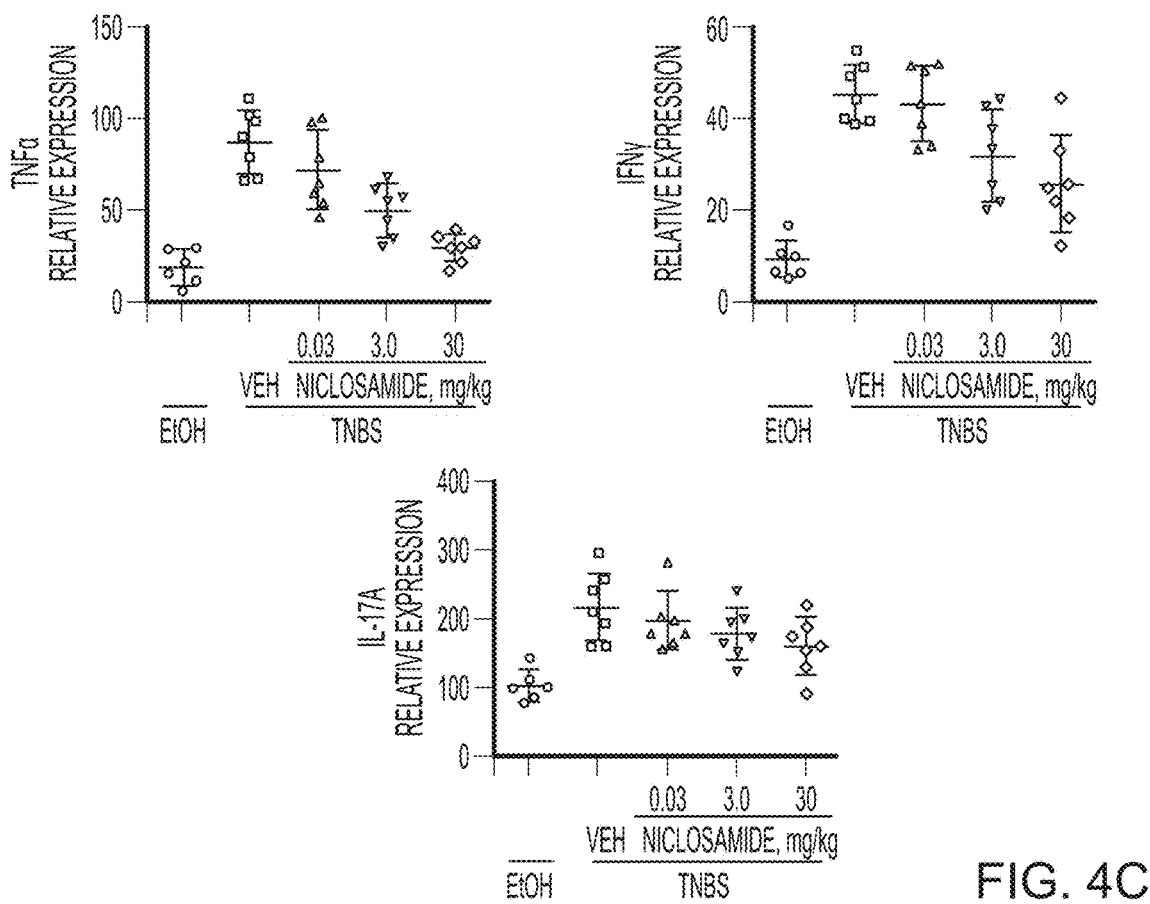
FIG. 4C includes graphs that demonstrate expression of inflammatory cytokines in intestinal biopsied tissue detected by real-time PCR. TNBS exposure in presence of vehicle increases expression of TNFa, IFNy and IL-17A compared to EtOH control animals that receive no TNBS. Niclosamide administered rectally at 0.03, 3.0 and 30 mg per kg body weight dose-dependently reduces the level of RNA of each cytokine relative to expression of RNA for β-actin, used as a housekeeping gene for normalization.

FIG. 4C demonstrates expression of inflammatory cytokines in intestinal biopsied tissue detected by real-time PCR. TNBS exposure in presence of vehicle increases expression of TNFa, IFNy and IL-17A compared to EtOH control animals that receive no TNBS. Niclosamide administered rectally at 0.03, 3.0 and 30 mg per kg body weight dose-dependently reduces the level of RNA of each cytokine relative to expression of RNA for β-actin, used as a housekeeping gene for normalization.

The results support the conclusions that rectally administered niclosamide suspension treats colitis in a mouse model of human inflammatory bowel disease that recapitulates features of human disease including colon infiltration by T cells and increased expression of pro-inflammatory cytokines. The treatment response to niclosamide suspension administered rectally includes dose-dependent modulation of pro-inflammatory cytokine gene expression. Collectively, these results exemplify the claim that rectal administration of niclosamide suspension is a treatment for inflammatory diseases of the colon.

Example 10. Niclosamide Reduces the Pro-Inflammatory Potential of T Cells Isolated from the Lamina Propria of Human Intestine Objective: The objective of this experiment was to determine if niclosamide directly reduces the proinflammatory potential of human T cells isolated from the lamina propria sampled as a biopsy from a person with ulcerative colitis (DC).

Model: Lamina propria mononuclear cells (LPMC) in the human intestine are comprised in part by T cells which mediate pathological processes including inflammatory bowel disease. LPMCs can be isolated from human intestine tissue biopsies. After isolation LPMCs T cells remain viable ex vivo under appropriate culture conditions for periods of time that allow ex vivo experiments. These cells can be used to investigate if test agents affect their production of pro-inflammatory cytokines including interferon-gamma (IFN), tumor necrosis factor-alpha (TNF) and interleukin 17A (IL-17A), to determine if a test agent affects the pro-inflammatory cytokines that mediate inflammatory bowel disease, including UC.

Cell Isolation and Culture: Cells were obtained from colon biopsy specimens of a human from areas with moderate to severe UC. For the isolation of lamina propria mononuclear cells (LPMCs), the specimens were initially washed in Hank's balanced salt solution (HBSS) then cut into 0.5-cm pieces, and incubated with stirring in pre-warmed HBSS containing 1 mM DTT at 37° C. for 15 minutes. The supernatant was removed and the sample washed with stirring with HBSS for 5 minutes twice. Samples were incubated with stirring in pre-warmed HBSS containing 5 mM EDTA for 30 minutes. The supernatant was removed and the sample washed with stirring with HBSS for 5 minutes three times. The tissue was then digested further in RPMI 1640 containing 2 mg/ml Liberase and 0.01 ug/ml DNase I for 1 hours at 37° C. with stirring. After digestion, the mononuclear cells in suspension were collected and centrifuged at 400 g for 10 minutes. After two washings in HBS, the pellet was resuspended in a 40% Percoll solution and layered on the top of a Percoll solution (100%, 60%, 40%, and 30% Percoll in HBSS). The tube was centrifuged at 400 g for 25 minutes, and LPMCs at the 60%-40% Percoll layer interface were collected. The isolated cells were counted and checked for viability using 0.1% trypan blue (viability ranged from 86% to 94%). Cells were washed out of Percoll with HBSS and resuspended in RPMI 1640 supplemented with 10% heat inactivated FBS, 1% L-glutamine, 100 U/mL penicillin, and 100 mg/mL streptomycin at a concentration of $1\times10^6$ cells/mL and plated in 96-well culture plates (200000 cells/well) (Nat Protoc. 2007; 2(10): 2307-11)

Treatment with Test Material Niclosamide—Niclosamide (purchased from Sigma) was dissolved in dimethyl sulfoxide (DMSO) and added to the culture medium to achieve a concentration of 5 µM. Samples were incubated for 24 h at 37° C. A vehicle only control (in place of niclosamide) was run concurrently.

Measuring pro-inflammatory cytokines. After treatment with either niclosamide or vehicle control as described above, LPMC were stimulated with PMA (10 ng/mL), ionomycin (1 µg/mL), and brefeldinA (10 µg/mL; eBioscience, San Diego, Calif.) After 5 h, cells were stained with the following Abs: anti-CD3-PerCP (1:50, final dilution, BD Biosciences, San Jose, Calif.) and fixed with 1% formaldehyde for 20'. Subsequently cells were permeabilized with 0.5% saponin in 1% BSA FACS buffer and stained with the following Abs: anti-IFN-γ-PE (1:50, final dilution; clone XMG1.2, BD Biosciences), anti-IL-17A-APC (1:50, final dilution, clone eBiol7B7 Affymetrix eBioscience), Anti-TNF-PEcy7 (1:50 final dilution, clone MP6-XT22 Affymetrix). Appropriate isotype-matched controls from BD Biosciences were included in all of the experiments. A flow cytometer FACSVerse flow cytometer and FACSSuite software [BD Biosciences] was used for to analyze results.

Figure 5:
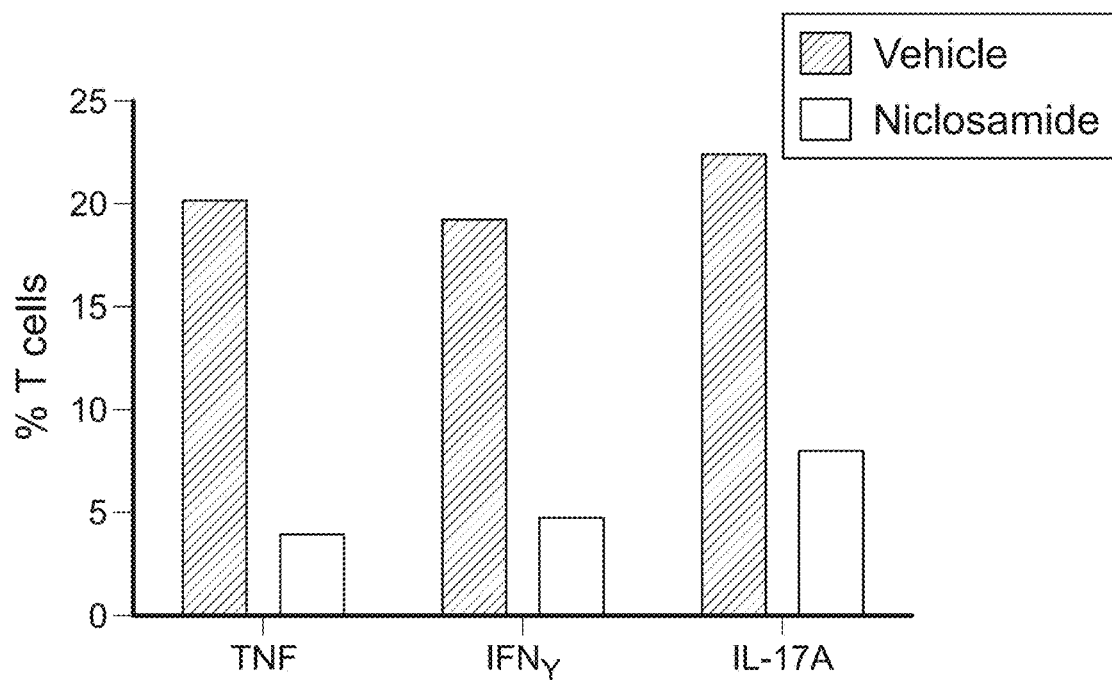
FIG. 5 is a graph showing that niclosamide at 5 µM causes a decrease in human LPMCs T cells that produce pro-inflammatory cytokines including TNF, IFN, and IL-17A relative to vehicle only negative control

Results and Conclusion—Niclosamide at 5 µM causes a decrease in human LPMCs T cells that produce pro-inflammatory cytokines including TNF, IFN, and IL-17A relative to vehicle only negative control (FIG. 5).

Example 11. Administration of Niclosamide Using a Formulation that Results in a Concentration of Niclosamide in the Rectal Mucosa that is Both Detectable and Significantly Greater than the Corresponding Plasma Niclosamide Concentration Rabbits (New Zealand White KBL Rabbit (SPF: Specific Pathogen Free), naïve to any experimental procedures, Charles River Laboratories S.p.A. Italia.—only males will be used) were treated with a single dose of niclosamide suspensions containing magnesium stearate and colloidal silica (98.5% Niclosamide, 1% Silica, colloidal hydrated, and 0.5% Magnesium stearate—manually crushed with mortar and pestle then sieved through 60 mesh (250 um) and then suspended in the liquid carrier described in Example 8) at the dose levels specified. Following dosing, blood samples and rectal mucosa was obtained at indicated time points. See Tables 13 and 14.

TABLE 13

Niclosamide Plasma Concentrations (ng/mL)
Treatment B 7.5
(Study Niclosamide: Evaluation of the Pharmacokinetics following a Single Rectal Administration to NZW Rabbits)

| Time Hours | Subject 666 | Subject 667 | Subject 668 | Subject 669 | Subject 670 | Mean ng/ml | Std dev |
|---|---|---|---|---|---|---|---|
| 0 | BLQ | BLQ | BLQ | BLQ | BLQ | NA | NA |
| 1 | 5.79 | 2.98 | 2.81 | 4.13 | BLQ | 3.9275 | 1.3731321 |
| 2 | 5.19 | 3.26 | 50.7 | | | 19.716667 | 25.849701 |
| 4 | BLQ | 21.7 | 2.21 | | | 11.955 | 13.781511 |

TABLE 13-continued

Niclosamide Plasma Concentrations (ng/mL)
Treatment B 7.5
(Study Niclosamide: Evaluation of the Pharmacokinetics following a Single Rectal Administration to NZW Rabbits)

| Time Hours | Subject 666 | Subject 667 | Subject 668 | Subject 669 | Subject 670 | Mean ng/ml | Std dev |
|---|---|---|---|---|---|---|---|
| 8 | 4.73 | 4.63 | BLQ | | | 4.68 | 0.0707107 |
| 24 | BLQ | 1.07 | BLQ | | | 1.07 | NA |

TABLE 14

Niclosamide Rectal Concentration (ng/ml) after 1 hour

| Subject 669 | Subject 670 | Mean | Std dev |
|---|---|---|---|
| 12.3 | 32.8 | 22.55 | 14.4957 |

Rectal administration of niclosamide (7.5 mg) results in mean rectal niclosamide concentration of 22.55 ng/ml (stdev 14.49) compared to a plasma concentration of 3.93 ng/ml (stdev 1.37) 1 hour following dosing. This difference means that the rectal concentration of niclosamide is more than 5-times the plasma concentration at 1 hr.

Example 12. Niclosamide Reduces Mitochondrial Membrane Potential in T Cells Isolated from the Lamina Propria of Human Intestine Objective—The objective of this experiment was to determine if niclosamide can directly reduce the mitochondrial transmembrane potential in T cells isolated from human intestine lamina propria.

The Model—Lamina propria mononuclear cells (LPMC) in the human intestine are comprised in part by T cells which mediate physiological and pathological processes including inflammatory bowel disease. LPMCs can be isolated from human tissue biopsies. After isolation LPMCs T cells remain viable ex vivo under appropriate culture conditions for periods of time that allow ex vivo experiments. These cells can be used to investigate mechanisms that regulate their mitochondrial function and survival They contain respiring mitochondria and as such their response to test agents may be assessed. Uncoupling is identified and quantified by a detecting a drop in the electrochemical gradient across the mitochondrial inner membrane ($\Delta\Psi m$).

Cell Isolation and Culture—Cells were obtained from biopsy specimens of the small or large intestine or rectum of humans from areas of gastrointestinal tissue with moderate to severe Crohn's disease (CD). For the isolation of lamina propria mononuclear cells (LPMCs), the specimens were initially washed in Hank's balanced salt solution (HBSS) then cut into 0.5-cm pieces, and incubated with stirring in pre-warmed HBSS containing 1 mM DTT at 37° C. for 15 minutes. The supernatant was removed and the sample washed with stirring with HBSS for 5 minutes twice. Samples were incubated with stirring in pre-warmed HBSS containing 5 mM EDTA for 30 minutes. The supernatant was removed and the sample washed with stirring with HBSS for 5 minutes three times. The tissue was then digested further in RPMI 1640 containing 2 mg/ml Liberase and 0.01 ug/ml DNase I for 1 hours at 37° C. with stirring. After digestion, the mononuclear cells in suspension were collected and centrifuged at 400 g for 10 minutes. After two washings in HBS, the pellet was resuspended in a 40% Percoll solution and layered on the top of a Percoll solution (100%, 60%, 40%, and 30% Percoll in HBSS). The tube was centrifuged at 400 g for 25 minutes, and LPMCs at the 60%-40% Percoll layer interface were collected. The isolated cells were counted and checked for viability using 0.1% trypan blue (viability ranged from 86% to 94%). Cells were washed out of Percoll with HBSS and resuspended in RPMI 1640 supplemented with 10% heat inactivated FBS, 1% L-glutamine, 100 U/mL penicillin, and 100 mg/mL streptomycin at a concentration of $1\times10^6$ cells/mL and plated in 96-well culture plates (200000 cells/well) (Nat Protoc. 2007; 2(10): 2307-11)

Treatment with Test Material Niclosamide—Niclosamide (purchased from Sigma) was dissolved in dimethyl sulfoxide (DMSO) and added to the culture medium to achieve a concentration of 5 µM. Samples were incubated for 60 min at 37° C. JC-1 was purchased from Thermo Fisher Scientific, dissolved in DMSO then added to the test wells to achieve a final concentration of 10 µg/ml and allowed to incubate at 37° C. for an additional 30 min. A vehicle only control (in place of niclosamide) was run concurrently. A flow cytometer FACSVerse flow cytometer and FACSSuite software [BD Biosciences] was used for quantification of JC-1 fluorescence in CD45+CD3+ cells.

Measuring mitochondrial membrane potential changes ($\Delta\Psi m$). JC-1 is a widely used indicator of mitochondrial membrane potential. JC-1 has advantages over other cationic dyes in that it exhibits potential-dependent accumulation in mitochondria indicated by a fluorescence emission shift from green (~525 nm) to red (~590 nm). Consequently, mitochondrial depolarization is indicated by a decrease in the red/green fluorescence intensity ratio. The potential-sensitive color shift is due to concentration dependent formation of red fluorescent J-aggregates.

Measurement of and Calculation of Change of $\Delta\Psi m$ in T cells—In order to specifically distinguish T cells from other cells in LPMCs, LPMC were stained with anti-CD45 and anti-CD3 antibodies. Anti-CD45 monoclonal antibody labeled with PerCP-Cyanine5.5 (Ex488 Em695) was purchased from Ebioscience (clone 2D1); anti-CD3 monoclonal antibody labeled with eFluor® 450 (Ex405 Em455) was purchased from Ebioscience (clone OKT3). The anti-CD45 antibody binds human CD45 antigen, that is expressed in by all hematopoietic cells excluding circulating erythrocytes and platelets. The anti-CD3 antibody specifically binds human CD3 antigen that is selectively expressed on T cells. LPMC CD45+CD3+ T cells were first defined by their fluorescence emission from labeling with eFluor® 450-anti-CD3 antibody and PerCP-Cyanine5.5-anti-CD3 antibody. The fluorescence intensity of JC-1 detected at ~525 nm and ~590 nm in the CD45+CD3+ T cell population was then measured.

Figure 6:
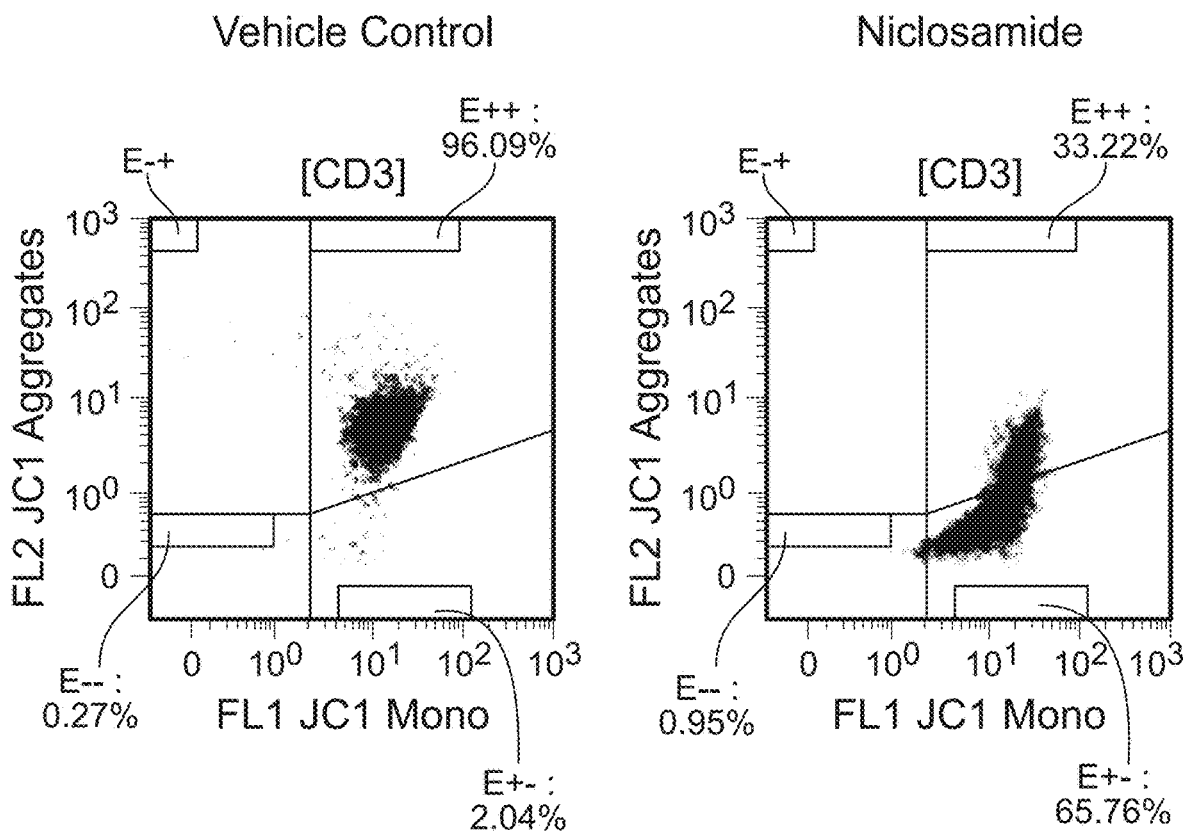
FIG. 6 is a graph showing that niclosamide at 5 µM causes a decrease in ΔΨm in human LPMCs T cells relative to negative control.

Results and Conclusion—Niclosamide at 5 µM causes a decrease in $\Delta\Psi m$ in human LPMCs T cells relative to negative control (see FIG. 6).

A number of embodiments of the invention have been described. Nevertheless, it will be understood that various modifications may be made without departing from the spirit and scope of the invention. Accordingly, other embodiments are within the scope of the following claims.

What is claimed is:

1. A method for treating gastrointestinal tissue damage in a subject in need thereof, the method comprising administering an effective amount of niclosamide, or a pharmaceutically acceptable salt thereof, wherein the gastrointestinal tissue damage is associated with unregulated recruitment and/or retention and/or activation of an immune cell in the subject.

2. The method of claim 1, wherein the method comprises locally administering an effective amount of niclosamide, or a pharmaceutically acceptable salt thereof, to the subject.

3. The method of claim 1, wherein the method comprises locally administering an effective amount of niclosamide, or a pharmaceutically acceptable salt thereof, to the gastrointestinal tract of the subject.

4. The method of claim 1, wherein the niclosamide, or a pharmaceutically acceptable salt thereof, is administered by oral administration.

5. The method of claim 3, wherein the niclosamide, or a pharmaceutically acceptable salt thereof, is administered by tablet or pill.

6. The method of claim 1, wherein upon administration, the concentration of niclosamide in the GI tract is higher than the concentration of niclosamide in the plasma compartment.

7. The method of claim 1, wherein the niclosamide, or a pharmaceutically acceptable salt thereof, is administered by inhalation.

8. The method of claim 1, wherein the subject is a human.

9. The method of claim 1, wherein the immune cell is a T-cell.

10. The method of claim 9, wherein the T cell is a gut tropic T cells.

11. The method of claim 10, wherein the gut tropic T cell expresses one or more gut-homing receptors selected from the group consisting of:
CD3+CCR9+;
CD3+α4+ or CD3+β7+;
CD3+α4+β7+;
CD3+β1+;
CD3+α4+β1+;
CD3+LFA1;
CD3+CCR4+; and
CD3+CCR10+.

12. The method of claim 1, wherein the gastrointestinal tissue damage is associated with unregulated recruitment and/or retention and/or activation of an immune cell in the gastrointestinal tract of the subject.

13. The method of claim 12, wherein the gastrointestinal tissue damage is associated with unregulated recruitment and/or retention and/or activation of an immune cell at the intestinal epithelium of the subject.

14. The method of claim 12, wherein the gastrointestinal tissue damage is associated with unregulated recruitment and/or retention and/or activation of an immune cell within the intestinal mucosa of the subject.

15. The method of claim 12, wherein the gastrointestinal tissue damage is associated with unregulated recruitment and/or retention and/or activation of an immune cell within the lamina propria of the subject.

16. The method of claim 12, wherein the gastrointestinal tissue damage is associated with unregulated recruitment and/or retention and/or activation of an immune cell within the Peyer's patches of the subject.

17. The method of claim 12, wherein the gastrointestinal tissue damage is associated with unregulated recruitment and/or retention and/or activation of an immune cell within the GALT (gut associated lymphoid tissue) of the subject.

18. The method of claim 12, wherein the gastrointestinal tissue damage is associated with unregulated recruitment and/or retention and/or activation of an immune cell within the intestinal submucosa of the subject.

19. The method of claim 12, wherein the gastrointestinal tissue damage is associated with unregulated recruitment and/or retention and/or activation of an immune cell within the intestinal muscular layer of the subject.

20. The method of claim 12, wherein the gastrointestinal tissue damage is associated with unregulated recruitment and/or retention and/or activation of an immune cell within the intestinal serosa of the subject.

21. The method of claim 1, wherein the gastrointestinal tissue damage is associated with an autoimmune colitis.

22. The method of claim 21, wherein the autoimmune colitis is an inflammatory bowel disease.

23. The method of claim 22, wherein the inflammatory bowel disease is ulcerative colitis.

24. The method of claim 22, wherein the inflammatory bowel disease is Crohn's disease.

25. The method of claim 21, wherein the autoimmune colitis is iatrogenic autoimmune colitis.

26. The method of claim 1, wherein the method comprises administering niclosamide.

27. The method of claim 1, wherein the gastrointestinal tissue damage is associated with abnormal recruitment and/or retention and/or activation of an immune cell in the subject.

28. The method of claim 1, wherein the gastrointestinal tissue damage is associated with elevated recruitment and/or retention and/or activation of an immune cell in the subject.

* * * * *